(12) United States Patent
Shen et al.

(10) Patent No.: US 8,158,623 B2
(45) Date of Patent: Apr. 17, 2012

(54) HEPTACYCLIC COMPOUNDS AND THE PHARMACEUTICAL USES THEREOF FOR PREVENTING AND TREATING DIABETES AND METABOLIC SYNDROME

(75) Inventors: Jianhua Shen, Shanghai (CN); Ying Leng, Shanghai (CN); Hualiang Jiang, Shanghai (CN); Junhua Chen, Shanghai (CN)

(73) Assignee: Shanghai Institute of Materia Medica Chinese Academy of Sciences, Shanghai (CN)

( * ) Notice: Subject to any disclaimer, the term of this patent is extended or adjusted under 35 U.S.C. 154(b) by 0 days.

(21) Appl. No.: 12/602,083

(22) PCT Filed: May 29, 2007

(86) PCT No.: PCT/CN2007/070059
§ 371 (c)(1),
(2), (4) Date: Dec. 29, 2009

(87) PCT Pub. No.: WO2008/144982
PCT Pub. Date: Dec. 4, 2008

(65) Prior Publication Data
US 2010/0173905 A1    Jul. 8, 2010

(51) Int. Cl.
*A61K 31/5375* (2006.01)
*A61K 31/497* (2006.01)
*A61K 31/40* (2006.01)
*A61K 31/335* (2006.01)
*C07D 413/02* (2006.01)
*C07D 405/02* (2006.01)
*C07D 321/00* (2006.01)

(52) U.S. Cl. ............... 514/232.8; 514/254.11; 514/422; 514/450; 544/148; 544/378; 548/526; 549/267

(58) Field of Classification Search .............. 514/232.8, 514/254.11, 422, 450; 544/148, 178; 548/526; 549/267
See application file for complete search history.

(56) References Cited

U.S. PATENT DOCUMENTS
5,350,763 A    9/1994 Feighner et al.

FOREIGN PATENT DOCUMENTS

| CN | 1780821 A | 5/2006 |
|---|---|---|
| JP | H57-002278 A | 1/1982 |
| WO | 97/22338 A1 | 6/1997 |
| WO | 98/45255 A1 | 10/1998 |
| WO | 03/080564 A1 | 10/2003 |
| WO | 2007/056388 A2 | 5/2007 |

OTHER PUBLICATIONS

Makhija, Mahindra T. QSAR of HIV-1 Integrase Inhibitors by Genetic Function Approximation Method. Bioorganic and Medicinal Chemistry. 10 (2002) 1483-1497.*
Kostova, I. Structure-Activity Relationships of Synthetic Coumarins as HIV-1 Inhibitors. Bioorganic Chemistry and Applications. Volume 2006, Mar. 12, 2005, pp. 1-9.*
The State Intellectual Property Office, the P.R. China, International Search Report, for International Application No. PCT/CN2007/070059, mailed Mar. 20, 2008.
Estela Correche et al., "Cytotoxic Screening Activity of Secondary Lichen Metabolites," Acta Farm. Bonaerense vol. 21 No. 4, pp. 273-278 (2002).

* cited by examiner

*Primary Examiner* — Rebecca Anderson
*Assistant Examiner* — Samantha Shterengarts
(74) *Attorney, Agent, or Firm* — Baker Botts L.L.P.

(57) ABSTRACT

The invention discloses a new use of a class of heptacyclic compounds in the preparation of formulations for the prevention and treatment of diabetes and metabolic syndromes; the present invention also discloses a new class of heptacyclic compounds; the present invention also discloses a process for preparing the heptacyclic compounds and a composition containing the same. The heptacyclic compounds of the present invention can be used to effectively preventing or treating diseases such as diabetes and metabolic syndromes.

(I)

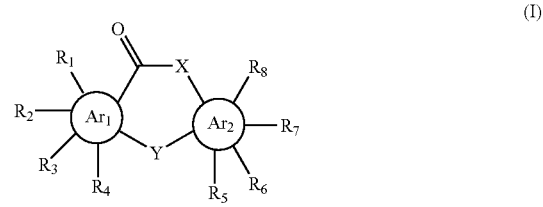

11 Claims, 2 Drawing Sheets

HEPTACYCLIC COMPOUNDS AND THE PHARMACEUTICAL USES THEREOF FOR PREVENTING AND TREATING DIABETES AND METABOLIC SYNDROME

CROSS-REFERENCE TO RELATED APPLICATION

This application is the National Stage of International Patent Application No. PCT/CN2007/070059, filed May 29, 2007, the disclosure of which is incorporated herein by reference in their entirety.

TECHNICAL FIELD

The present invention pertains to pharmaceutical field. In particular, the present invention relates to a class of new heptacyclic compounds, a pharmaceutical use thereof for preventing and treating diabetes and metabolic syndrome and compositions containing the said compounds.

BACKGROUND OF THE INVENTION

The Diabetes Mellitus (DM) is a metabolic disease caused by many etiological factors, the characteristic of which is chronic hyperglycemia, accompanied with glucose, lipid and protein metabolism disorders caused by the deficiency of insulin secretion and/or action. It is a clinical syndrome (a chronic, systematic or metabolic disease) caused by the interaction of hereditary factors and environmental factors. Most of the Diabetes Mellituses are caused by absolute or relative deficiency of insulin in human bodies and mainly characterized by hyperglycaemia. The diabetes is a lifetime disease.

Diabetes mellitus may be categorized into two subclasses: type I and type II. The type II diabetes is more dangerous and comprising over 90% of individuals suffering from diabetes. As the type II diabetes is often caused by obesity and lack of exercise, the incidence of Type II diabetes has increased rapidly in developed countries. The number of diabetes patients is expected to grow to over 200 millions in the world in 2010, and over 300 millions in 2025.

Generally, the type II diabetes is characterized by hyperglycemia, which causes metabolic disorders in vivo, and then develops into complications, referred to as metabolic syndromes, such as nervous system disease, kidney diseases, retinopathy, hypertriglyceridemia, obesity and cardiovascular disease. Diabetes is regarded as a fifth fatal disease in the world since it often causes complications in blood circulation and nervous system. On May $5^{th}$ 2004, WHO reported that currently about 3.2 millions of death is caused by the diabetes-induced complications in the world every year. In most countries, diabetes has become one of the main causes of early death.

Diabetes is a clinical syndrome caused by the interaction between hereditary factors and environmental factors such as high fat diet, lack of exercise, obesity, aging and the like. It is caused by two pathogenic factors: insulin resistance and islet β cells failure. A variety of treating molecules targeting diabetes-related features have been found, and some medicaments have been developed for clinical treatment. For example, (1) sulfonylureas, which depolarize pancreatic islet β cells by inhibiting ATP-dependent potassium channel, thus leading to the opening of calcium channels, increasing $Ca^{2+}$ influx of β cells and inducing the secretion of insulin; (2) biguanides, which may facilitate the intake of glucose by muscle tissues, accelerate anaerobic glycolysis, inhibit gluconeogenesis and reduce the output of liver sugar; (3) α-glucosidase inhibitors, which treat diabetes by inhibiting the activity of α-glucosidase in the digestive tract and delaying the digestion and absorption of carbohydrates; (4) thiazolidinediones (TZD), which may activate nuclear receptor PPARγ, regulate the differentiation of adipose cells, increase insulin sensitivity and the like. However, all of these medicaments are based on different targets and have some limitations.

At present, oral hypoglycemic drugs for treating Type II diabetes are typically combined administration of sulfonylureas and biguanides. However, sulfonylureas can be associated with primary or secondary failure during the course of treatment, and sometimes leading to hypoglycemia and obesity. Biguanides tend to induce hyper-lactic acid, nausea and diarrhea. TZD antidiabetic drugs regulate blood glucose metabolism by activating PPARγ and thus have some advantages in treating diabetes. However, many undesirable side effects of TZD drugs, such as cardiac enlargement, hemodilution and hepatotoxicity are gradually emerging in clinical applications. A lot of malpractices in which liver damage or even death may occur due to the use of TZD drugs have been reported. Therefore, there is a need to find one safer and more effective antidiabetic drug.

Metabolic syndrome is a disease caused by pathobolism. The pathophysiology basis of metabolic syndrome is carbohydrate, lipid and protein metabolism disorders. Clinical situations of patients are mainly hypertension, hyperglycemia or insulin resistance (although the blood glucose is not high), hyperinsulinemia, hyperlipemia, microalbuminuria, obesity—especially central obesity. The patients may also suffer from fatty liver, gallstone, hyperuricacidemia, arthrolithiasis, osteoporosis, artherosclerosis and the like because of the above three kinds of pathobolisms. Although metabolic syndrome will not threat life directly, it will result in other serious life-threatening diseases, such as cerebral apoplexy and coronary heart disease. Therefore, it is a disease which can not be neglected. The main indexes for the diagnosis of the metabolic syndrome are blood glucose, triglyceride, total cholesterol (TC), unsaturated free fatty acid (NFFA), and uric acid. If the above indexes exceed the normal level, one can be diagnosed of metabolic syndrome.

Metabolic syndrome is closely correlated to Type II diabetes, and can be considered as one important form of pre-diabetes. Metabolic syndrome mainly includes insulin resistance, hyperinsulinemia, impaired glucose tolerance, obesity, hypercholesteremia, abnormal metabolism of lipid, angiosclerosis, coronary artery disease, hypertension, hyperuricacidemia and arthrolithiasis, the clinical situations of which are mainly abdominal fat, scleratheroma dyslipidemia, hypertension, insulin resistance (accompanied with or without abnormal glucose tolerance), embolism, and inflammation. The development of metabolic syndrome is closely correlated to the occurance of cardiovascular disease and Type II diabetes, seriously threatening people's health. The therapy scheme of metabolic syndrome in most cases is that appropriate medicaments are selected according to the clinical symptoms, for example, lipidase inhibitors and serotonin reuptake inhibitors (SSRIs) may be used to reduce weight; fibrates and nicotinamides may be used to reduce lipid; biguanides, thiazolidinediones, α-glucosidase inhibitors may be used to improve insulin resistance or abnormal glucose tolerance; ACE inhibitors and α1 receptor blocker may be used to treat hypertension. However, since metabolic syndrome is usually associated with several clinical situations, a medicament having hypoglycemic, hypolipidemic effects as well as improving insulin resistance will show significant therapeutic effects for metabolic syndrome.

In summary, it is urgent to develop a new drug which has good effects in the prevention and treatment of diabetes or metabolic syndrome, and therefore improve the quality of life for various patients.

DETAILED DESCRIPTION OF THE INVENTION

One object of the present invention is to provide a use of heptacyclic compounds in the prevention and treatment of diabetes and metabolic syndrome.

Another object of the present invention is to provide a new class of heptacyclic compounds.

Another object of the present invention is to provide a pharmaceutical composition, a health product or a food composition containing the heptacyclic compounds.

Another object of the present invention is to provide a process for preparing the heptacyclic compounds.

Another object of the present invention is to provide a method for preventing and treating diabetes and metabolic syndrome.

In the first aspect of the present invention, it is provided a use of a compound having the structure of Formula I:

Formula I

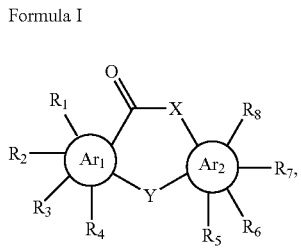

(I)

or isomers, racemates, pharmaceutically acceptable salts thereof and their mixtures in the preparation of a medicament for preventing and treating diabetes and metabolic syndrome, wherein $Ar_1$ and $Ar_2$ are selected from benzene or heterocycle; X and Y are selected from O, N, S or $SO_2$;

$R_1$, $R_2$, $R_3$, $R_4$, $R_5$, $R_6$, $R_7$ and $R_8$ are independently selected from hydrogen, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, halo, —COOR', —NR'R", —OR', —COR', —CONR'R", =O, —SR', —$SO_3$R', —$SO_2$NR'R", —SOR', —$SO_2$R', —$NO_2$ or —CN;

wherein R' and R" are independently selected from hydrogen, unsubstituted or substituted phenyl, unsubstituted or substituted benzyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, or R' and R" are taken together to form a 4- to 7-membered ring. R' and R" can be the same group or different groups.

In another preferred example, $R_3$ is —OR'; more preferably, $R_3$ is —OH.

In another preferred example, $R_1$, $R_2$, $R_7$ and $R_8$ are independently selected from the group consisting of hydrogen, unsubstituted or substituted $C_1$-$C_{10}$ alkyl, unsubstitued or substituted $C_2$-$C_{10}$ alkenyl, unsubstituted or substituted $C_2$-$C_{10}$ alkynyl, and halo; $R_3$, $R_4$, $R_5$ and $R_6$ are independently selected from hydrogen, —COOR', —NR'R", —OR', —COR', —CONR'R", =O, —SR', —$SO_3$R', —$SO_2$NR'R", —SOR', —$SO_2$R', —$NO_2$ or —CN.

In another preferred example, the substituents are 1-3 groups selected from the group consisting of: $C_1$-$C_{10}$ alkyl, $C_2$-$C_{10}$ alkenyl, $C_2$-$C_{10}$ alkynyl, halo, —$COOR_a$, —$NR_aR_b$, —$OR_a$, —$COR_a$, —$CONR_aR_b$, =O, —$SR_a$, —$SO_3R_a$, —$SO_2NR_aR_b$, —$SOR_a$, —$SO_2R_a$, —$NO_2$ or —CN; wherein $R_a$ and $R_b$ independently can be selected from hydrogen, $C_1$-$C_{10}$ alkyl, $C_2$-$C_{10}$ alkenyl, or $C_2$-$C_{10}$ alkynyl.

In another preferred example, $R_2$ is H; $R_3$ is —OH; $R_4$ is —CHO; $R_5$ is selected from H, methyl or carboxy; $R_6$ is selected from H or carboxy; $R_7$ is H, —OH or —$OCH_3$; $R_1$ and $R_8$ are selected from H, methyl or —$CH_2OC_2H_5$, alkoxyl.

In another preferred example, the mammal is human.

In another preferred example, the isomers include, but are not limited to, geometric isomers, enantiomers, and diastereoisomers.

In another preferred example, $Ar_1$ and/or $Ar_2$ is benzene.

In another preferred example, the metabolic syndromes include, but are not limited to, insulin resistance, hyperinsulinemia, abnormal glucose tolerance, obesity, adiposis hepatica, hyperuricacidemia, arthrolithiasis, hyperlipemia, hypercholesteremia, artherosclerosis or hypertension.

In the second aspect of the present invention, it is provided a compound having the structure of Formula I:

Formula I

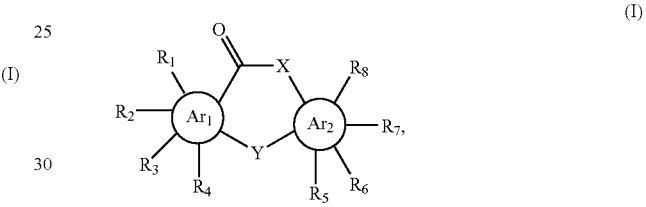

(I)

or isomers, racemates, or pharmaceutically acceptable salts thereof, wherein, $Ar_1$ and $Ar_2$ are selected from benzene or heterocycle; X and Y are selected from O, N, S or $SO_2$; $R_3$ is —OR';

$R_1$, $R_2$, $R_4$, $R_5$, $R_6$, $R_7$ and $R_8$ are independently selected from hydrogen, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, halo, —COOR', —NR'R", —OR', —COR', —CONR'R", =O, —SR', —$SO_3$R', —$SO_2$NR'R", —SOR', —$SO_2$R', —$NO_2$ or —CN;

wherein R' and R" are independently selected from hydrogen, unsubstituted or substituted phenyl, unsubstituted or substituted benzyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, or R' and R" are taken together to form a 4- to 7-membered ring.

In another preferred example, $R_1$, $R_2$, $R_7$ and $R_8$ are independently selected from the group consisting of hydrogen, unsubstituted or substituted $C_1$-$C_{10}$ alkyl, unsubstitued or substituted $C_2$-$C_{10}$ alkenyl, unsubstituted or substituted $C_2$-$C_{10}$ alkynyl, and halo; $R_4$, $R_5$, $R_6$ are independently selected from the group consisting of hydrogen, —COOR', —NR'R", —OR', —COR', —CONR'R", =O, —SR', —$SO_3$R', —$SO_2$NR'R", —SOR', —$SO_2$R', —$NO_2$ and —CN.

In another preferred example, the substituents are 1-3 groups selected from the group consisting of: $C_1$-$C_{10}$ alkyl, $C_2$-$C_{10}$ alkenyl, $C_2$-$C_{10}$ alkynyl, halo, —$COOR_a$, —$NR_aR_b$, —$OR_a$, —$COR_a$, —$CONR_aR_b$, =O, —$SR_a$, —$SO_3R_a$, —$SO_2NR_aR_b$, —$SOR_a$, —$SO_2R_a$, —$NO_2$ or —CN; wherein $R_a$ and $R_b$ independently are hydrogen, $C_1$-$C_{10}$ alkyl, $C_2$-$C_{10}$ alkenyl, $C_2$-$C_{10}$ alkynyl.

In another preferred example, $Ar_1$ and/or $Ar_2$ is benzene.

In another preferred example, one of X and Y is not O.

In another preferred example, when one of X and Y is not O, $R_4$ is —$CH_2NR_9R_{10}$ or —$CH=NR_9$;

wherein $R_9$ and $R_{10}$ independently are hydrogen, unsubstituted or substituted phenyl, unsubstituted or substituted benzyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, —$COR_c$, —$CONR_cR_d$; or $R_9$ and $R_{10}$ are taken together with an adjacent nitrogen atom to form a 4- to 7-membered ring;

wherein $R_c$ and $R_d$ independently are hydrogen, unsubstituted or substituted $C_1$-$C_{10}$ alkyl, unsubstituted or substituted $C_2$-$C_{10}$ alkenyl, unsubstituted or substituted $C_2$-$C_{10}$ alkynyl; or $R_c$ and $R_d$ are taken together to form a 4- to 7-membered ring.

In another preferred example, the compound has the structure of Formula (II):

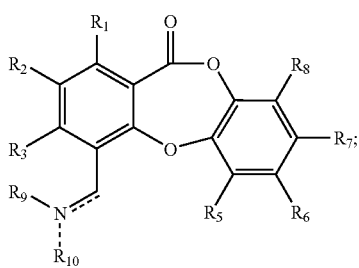

Wherein, $R_1$, $R_2$, $R_3$, $R_5$, $R_6$, $R_7$, $R_8$ are the same as defined above;

$R_9$ and $R_{10}$ independently are hydrogen, unsubstituted or substituted phenyl, unsubstituted or substituted benzyl, unsubstituted or substituted $C_1$-$C_{10}$ alkyl, unsubstitued or substituted $C_2$-$C_{10}$ alkenyl, unsubstituted or substituted $C_2$-$C_{10}$ alkynyl, unsubstituted or substituted amino, —$COR_c$, —$CONR_cR_d$; or $R_9$ and $R_{10}$ are taken together with an adjacent nitrogen atom to form a 4- to 7-membered ring;

wherein $R_c$ and $R_d$ independently are hydrogen, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, or $R_c$ and $R_d$ are taken together to form a 4- to 7-membered ring.

In another preferred example, when

is

, $R_{10}$ is absent; when

is

, $R_9$ and $R_{10}$ are both present.

In another preferred example, the compound is selected from:
4-Formyl-3-hydroxy-8-methoxy-1,9-dimethyl-11-oxo-11H-dibenzo[b,e][1,4]dioxepine-6-carboxylic acid ethyl ester (A2);
4-Formyl-3-hydroxy-8-methoxy-1,9-dimethyl-11-oxo-11H-dibenzo[b,e][1,4]dioxepine-6-carboxylic acid propyl ester (A4);
3-Hydroxy-8-methoxy-1,9-dimethyl-11-oxo-4-phenylaminomethyl-11H-dibenzo[b,e][1,4]dioxepine-6-carboxylic acid (B9);
3-Hydroxy-8-methoxy-1,9-dimethyl-11-oxo-4-[(2-pyrrol-1-yl-ethylamino)-methyl]-11H-dibenzo[b,e][1,4]dioxepine-6-carboxylic acid (C1);
3-Hydroxy-8-methoxy-1,9-dimethyl-11-oxo-4-[(4-sulfamoylphenyl)-aminomethyl]-11H-dibenzo[b,e][1,4]dioxepine-6-carboxylic acid (C3);
3-Hydroxy-8-methoxy-1,9-dimethyl-11-oxo-4-[(2-morpholin-4-yl-ethylamino)-methyl]-11H-dibenzo[b,e][1,4]dioxepine-6-carboxylic acid (C7);
3-Hydroxy-8-methoxy-1,9-dimethyl-11-oxo-4-(piperazin-1-ylmethyl)-11H-dibenzo[b,e][1,4]dioxepine-6-carboxylic acid (D1);
4-(tert-Butylamino-methyl)-3-hydroxy-8-methoxy-1,9-dimethyl-11-oxo-11H-dibenzo[b,e][1,4]dioxepine-6-carboxylic acid (D3);
4-(4-Benzyl-piperazin-1-ylmethyl)-3-hydroxy-8-methoxy-1,9-dimethyl-11-oxo-11H-dibenzo[b,e][1,4]dioxepine-6-carboxylic acid (D4);
4-[(4-Acetylamino-phenyl)aminomethyl]-3-hydroxy-8-methoxy-1,9-dimethyl-11-oxo-11H-dibenzo[b,e][1,4]dioxepine-6-carboxylic acid (D8);
3-Hydroxy-4-hydroxymethyl-8-methoxy-1,9-dimethyl-11-oxo-11H-dibenzo[b,e][1,4]dioxepine-6-carboxylic acid (E9);
Dibenzo[b,e][1,4]dioxepin-11-one (AA0);
4-[(4-Fluoro-phenylamino)-methyl]-3-hydroxy-8-methoxy-1,9-dimethyl-11-oxo-11H-dibenzo[b,e][1,4]dioxepine-6-carboxylic acid (AA7);
4-Formyl-3-hydroxy-8-methoxy-1,9-dimethyl-11-oxo-11H-dibenzo[b,e][1,4]dioxepine-6-carboxylic acid methylamide (AB2);
4-Formyl-3-hydroxy-8-methoxy-1,9-dimethyl-11-oxo-11H-dibenzo[b,e][1,4]dioxepine-6-carboxylic acid ethylamide (AB4);
4-Formyl-3-hydroxy-8-methoxy-1,9-dimethyl-11-oxo-11H-dibenzo[b,e][1,4]dioxepine-6-carboxylic acid diethylamide (AB5);
4-(Benzylimino-methyl)-3-hydroxy-8-methoxy-1,9-dimethyl-11-oxo-11H-dibenzo[b,e][1,4]dioxepine-6-carboxylic acid benzylamide (AB6);
3-Hydroxy-8-methoxy-1,9-dimethyl-11-oxo-4-[(4-sulfamoyl-phenyl)-imino-methyl]-11H-dibenzo[b,e][1,4]dioxepine-6-[carboxy-(4-sulfamoyl)-phenylamide] (AB9);
2-Chloro-3-hydroxy-8-methoxy-5,10-dihydro-dibenzo[b,e][1,4]diazepin-11-one (BT5);
9-Hydroxy-3-methoxy-6-oxo-6,11-dihydro-5H-benzo[e]pyrido[3,2-b][1,4]diazepine-10-carbaldehyde (BU0);

4-Formyl-3-hydroxy-8-methoxy-1,9-dimethyl-11-oxo-11H-dibenzo[b,e][1,4]dioxepine-6-carboxylic acid butyl ester (A6);

4-Formyl-3-hydroxy-8-methoxy-1,9-dimethyl-11-oxo-11H-dibenzo[b,e][1,4]dioxepine-6-carboxylic acid pentyl ester (A8);

8-Methyl-5-oxo-6,11-dihydro-5H-benzo[b]pyrido[2,3-e][1,4]diazepine-10-carboxylic acid (BT7)

3-Hydroxy-8-methoxy-1,9-dimethyl-11-oxo-4-[(4-sulfamoylphenyl)-amino-methyl]-11H-dibenzo[b,e][1,4]dioxepine-6-carboxylic acid propyl ester (AA5);

3-Hydroxy-8-methoxy-1,9-dimethyl-11-oxo-4-[(2-morpholin-4-yl-ethylamino)-methyl]-11H-dibenzo[b,e][1,4]dioxepine-6-carboxylic acid propyl ester (AA6);

4-[(4-Fluoro-phenylamino)-methyl]-3-hydroxy-8-methoxy-1,9-dimethyl-11-oxo-11H-dibenzo[b,e][1,4]dioxepine-6-carboxylic acid (AA7);

More preferably, the compound is selected from the group consisting of A0, A2, C1, C3, C7, D1, D8, AB5, G0, BT5, BU0, and F7. Still more preferably, the compound is selected from the group consisting of A2, C1, C3, C7, D1, D8, AB5, G0, and BT5.

In the third aspect of the present invention, it is provided a composition comprising:

(a) an effective amount of a compound of Formula I, isomers, racemates, pharmaceutically acceptable salts thereof or their mixtures.

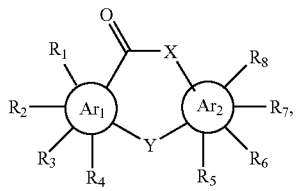

(I)

wherein $Ar_1, Ar_2, X, Y, R_1, R_2, R_3, R_4, R_5, R_6, R_7, R_8$ are the same as defined above;

(b) a bromatologically or pharmaceutically acceptable carrier or excipient.

In a preferred example, the composition further comprises:

(c) one or more medicaments selected from the group consisting of antidiabetic drugs, hypolipidemic drugs, weight-reducing aids, antihypertensive drugs, and antithrombotic drugs.

In another preferred example, 1 g of the composition contains 10-200 mg of component (a).

In another preferred example, 1 g of the composition contains 1-500 mg of component (c).

In another preferred example, the antidiabetic drugs are selected from Biguanides, Sulfonylureas, Glinides, α-glucosidase inhibitors, Euglycemic agents (such as thiazolidinedione drugs), aP2 inhibitors, DPPIV inhibitors, SGLT2 inhibitors, Insulin, Glucagon-like peptide-1 (GLP-1) or its analogue; or the hypolipidemic drugs are selected from MTP inhibitors, HMG-CoA Reductase inhibitors, squalene synthetase inhibitors, fibrates, acyl CoA-cholesterol acyltransferase (ACAT) inhibitors, lipoxygenase inhibitors, cholesterol absorption inhibitors, cholic acid/sodium cholate Cotransporter inhibitors, low density lipoprotein receptor activity up-regulators, cholic acid sequestrants, Nicotinic Acid or their derivatives; or the weight-reducing aids are selected from β3 adrenergic agonists, lipidase inhibitors, serotonin reuptake inhibitors, aP2 inhibitors, thyroid receptor agonists, cannabis receptor CB-1 antagonist or their derivatives; or the antihypertensive drugs are selected from ACE inhibitors, angiotensin II receptor antagonist, calcium channel blocking agents, beta-adrenergic blockers, or diuretics; or the anticoagulant drugs are selected from Platelet Aggregation Inhibitors.

In another preferred example, the dosage forms of the composition are selected from tablets, capsules, powders, granules, syrups, solutions, suspensions or aerosols.

In the fourth aspect of the present invention, it is provided a process for preparing the compound of Formula I:

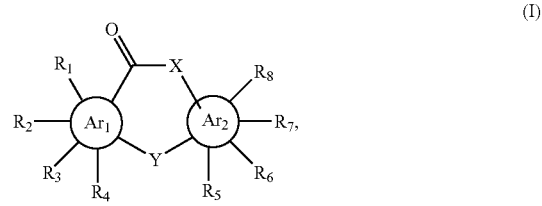

(I)

wherein $Ar_1, Ar_2, X, Y, R_1, R_2, R_3, R_4, R_5, R_6, R_7, R_8$ are the same as defined above;

The process comprises the following steps:

(a) condensing a compound of formula (IV) with a compound of formula (V) to form a compound of formula (VI):

(IV)

(V)

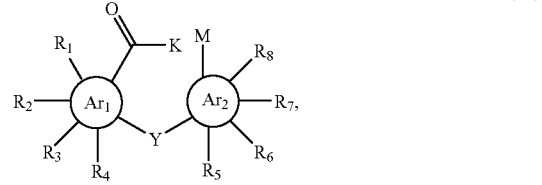

(VI)

wherein, K is selected from $C_{3-6}$ alkoxy, amino, unsubstituted or substituted aryloxy or unsubstituted or substituted benzyloxy; L is selected from halogen, $C_{3-6}$ alkoxy, amino, unsubstituted or substituted aryloxy or unsubstituted or substituted benzyloxy, thiol group;

M is selected from $C_{3-6}$ alkoxy, amino, unsubstituted or substituted aryloxy or unsubstituted or substituted benzyloxy, thiol group; Z is selected from halogen, $C_{3-6}$ alkoxy, amino, unsubstituted or substituted aryloxy or unsubstituted or substituted benzyloxy, thiol group;

(b) deprotecting and/or dehydrating compounds of formula (VI) to form the desired compounds through intramolecular cyclization.

In another preferred example, the protecting groups include, but are not limited to, methyl, isopropyl, benzyl, tetrahydropyranyl, acetyl, methoxymethyl, t-butyloxymethyl, trimethylsilyl.

In the fifth aspect of the present invention, it is provided a method for the prevention or treatment of diabetes and metabolic syndromes in mammals, which comprises administering to the mammal in need thereof an effective amount of the compound of Formula I, or isomers, racemates, pharmaceutically acceptable salts thereof or their mixtures.

In another preferred example, the effective amount is in the range of 10-1000 mg/day/person.

In another preferred example, the metabolic syndromes include, but are not limited to, insulin resistance, hyperinsulinemia, abnormal glucose tolerance, obesity, adiposis hepatica, hyperuricacidemia, arthrolithiasis, hyperlipemia, hypercholesteremia, artherosclerosis or hypertension.

The other aspects of the present invention will be obvious to those skilled in the art from the disclosure of the present application.

MODES FOR CARRYING OUT THE INVENTION

Figure 1:
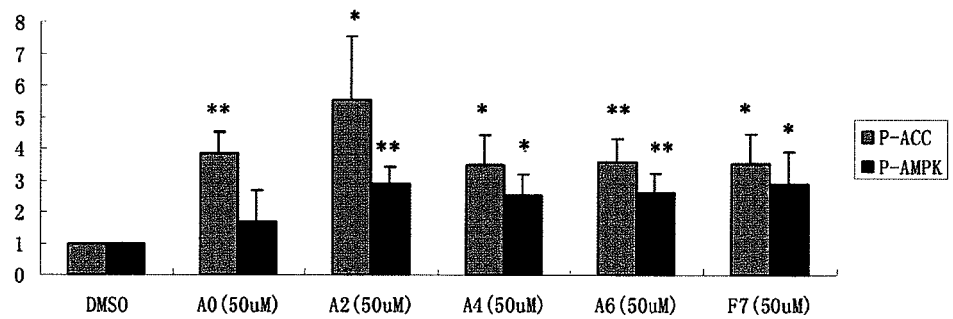
FIG. 1 shows the effect of some heptacyclic compounds on ACC, AMPK protein phosphorylation in HepG2 cell, **P<0.01; *P<0.05, versus DMSO.

After intensive and extensive studies and experiments, the inventors unexpectedly found a new class of heptacyclic compounds which have excellent effects for the prevention and treatment of diabetes and metabolic syndrome. Based on this research, the present invention is completed.

As used herein, the term "alkyl group" includes straight or branched saturated aliphatic hydrocarbon groups containing 1 to 10 carbon atoms (preferably, 1 to 8 carbon atoms; more preferably, 1 to 6 carbon atoms). For example, alkyl groups include, but are not limited to, methyl, ethyl, n-propyl, isopropyl, n-butyl, isobutyl, tert-butyl. The term "Alkoxyl group" refers to alkyl group containing an oxygen atom.

As used herein, the term "alkenyl group" includes straight or branched hydrocarbon groups comprising at least one carbon-carbon double bond and 2 to 10 carbon atoms (preferably, 2 to 8 carbon atoms; more preferably, 2 to 6 carbon atoms).

As used herein, the term "alkynyl group" includes straight or branched hydrocarbon groups comprising at least one carbon-carbon triple bond and 2 to 10 carbon atoms (preferably, 2 to 8 carbon atoms; more preferably, 2 to 6 carbon atoms).

As used herein, the term "heterocycle" refers to a stable 4 to 7 membered monocycle or a stable polycyclic heterocycle (preferably, it is a monocycle), wherein the heterocycle may be saturated, partially unsaturated or unsaturated and comprises carbon atoms and 1-4 heteroatoms selected form the group consisting of nitrogen, oxygen and sulphur. Nitrogen and sulphur atom could be oxidized. The heterocycle may also include any polycycle having any of the heterocycle condensed with an aryl ring.

As used herein, the term "halogen" or "halo" means F, Cl, Br or I.

As used herein, alkyl, alkenyl, alkynyl, phenyl, heterocycle, alkoxyl may or may not have substituents. For example, they can be substituted by 1 to 6 (preferably 1 to 3) substituents selected from, but are not limited to, $C_1$-$C_{10}$ alkyl, $C_2$-$C_{10}$ alkenyl, $C_2$-$C_{10}$ alkynyl, halo, —COOR$_a$, —NR$_a$, R$_b$—OR$_a$, —COR$_a$, —CONR$_a$R$_b$, =O, —SR$_a$, —SO$_3$R$_a$, —SO$_2$NR$_a$R$_b$, —SOR$_a$, —SO$_2$R$_a$, —NO$_2$ or —CN; wherein R$_a$ and R$_b$ independently are hydrogen, $C_1$-$C_{10}$ alkyl, $C_2$-$C_{10}$ alkenyl, $C_2$-$C_{10}$ alkynyl. It should be understood by the skilled in the art that the alkyl, alkenyl, alkynyl, alkoxyl, phenyl may be further substituted.

As used herein, the term "isomers" include, but are not limited to, geometric isomers, enantiomers, diastereoisomers (such as cis- and trans-isomers, conformational isomers).

As used herein, "$\rule{0.5cm}{0.1mm}$" represents that the chemical bond at this position may be a single bond or a double bond; "$\cdots$" represents that the chemical bond or group at this position is present or absent.

Compounds

Firstly, the present invention provides a compound of Formula I.

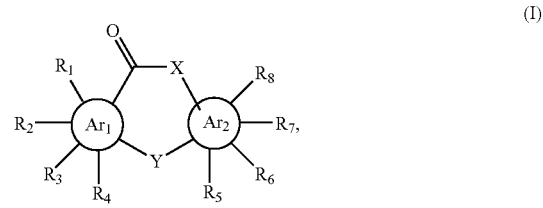

(I)

wherein: Ar$_1$ and Ar$_2$ can be selected from phenyl or heterocycle; X and Y can be selected from O, N, S or SO$_2$;

R$_1$, R$_2$, R$_3$, R$_4$, R$_5$, R$_6$, R$_7$ and R$_8$ are independently selected from hydrogen, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, halo, —COOR', —NR'R", —OR', —COR', —CONR'R", =O, —SR', —SO$_3$R', —SO$_2$NR'R", —SOR', —SO$_2$R', —NO$_2$ or —CN;

wherein R' and R" are independently selected from hydrogen, unsubstituted or substituted phenyl, unsubstituted or substituted benzyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, or R' and R" are taken together to form a 4- to 7-membered ring.

As a preferred embodiment of the compound of formula (I), R$_1$, R$_2$, R$_7$ and R$_8$ are independently selected from the group consisting of hydrogen, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, and halo; R$_3$, R$_4$, $R_5$, $R_6$ are independently selected from the group consisting of hydrogen, —COOR', —NR'R", —OR', —COR', —CONR'R", =O, —SR', —SO$_3$R', —SO$_2$NR'R", —SOR', —SO$_2$R', —NO$_2$ or —CN.

As a preferred embodiment of the compound of formula (I), $Ar_1$ and/or $Ar_2$ is a benzene ring.

As a preferred embodiment of the compound of formula (I), $R_3$ is —OR'; more preferably, $R_3$ is —OH.

As a preferred embodiment of the compound of formula (I), one of X and Y is not O. For example, when X is N, Y is O; when X is N, Y is N; when X is N, Y is S; when X is O, Y is S; when X is O, Y is N.

More preferably, when one of X and Y is not O, $R_4$ is —CH$_2$NR$_9$R$_{10}$ or —CH=NR$_9$; wherein $R_9$ and $R_{10}$ independently are hydrogen, unsubstituted or substituted phenyl, unsubstituted or substituted benzyl, unsubstituted or substituted C$_1$-C$_{10}$ alkyl, unsubstitued or substituted C$_2$-C$_{10}$ alkenyl, unsubstituted or substituted C$_2$-C$_{10}$ alkynyl, COR$_c$, —CONR$_c$R$_d$; or $R_9$ and $R_{10}$ are taken together with an adjacent N to form a 4- to 7-membered ring; wherein $R_c$ and $R_d$ are independently selected from hydrogen, unsubstituted or substituted C$_1$-C$_{10}$ alkyl, unsubstituted or substituted C$_2$-C$_{10}$ alkenyl, unsubstituted or substituted C$_2$-C$_{10}$ alkynyl; or $R_c$ and $R_d$ are taken together to form a 4- to 7-membered ring.

As a preferred embodiment of the compound of formula (I), when both X and Y are oxygen atoms, the compound has the structure of Formula (II):

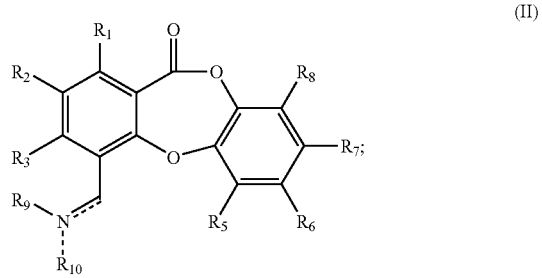

(II)

wherein:

$R_9$ and $R_{10}$ are the same as defined above; wherein when

is

, $R_{10}$ is absent; when

is

, $R_9$ and $R_{10}$ are both present;

As a most preferred embodiment of the present invention, $R_2$ is H; $R_3$ is —OH; $R_4$ is —CHO; $R_5$ is H, methyl or carboxy; $R_6$ is H or carboxy; $R_7$ is H, —OH or —OCH$_3$; $R_1$ and $R_8$ are selected from H, methyl or —CH$_2$OC$_2$H$_5$, alkoxyl.

The present invention also relates to isomers, racemates and pharmaceutically acceptable salts, solvates and prodrugs of the above compound. "Pharmaceutically acceptable salt" refers to a salt formed by the heptacyclic compound and inorganic acid, organic acid, alkali metal or alkaline earth metal. The salts include, but are not limited to: (1) a salt formed with inorganic acids including hydrochloric acid, sulfuric acid, nitric acid, phosphoric acid; (2) a salt formed with organic acids including acetic acid, oxalic acid, butanedioic acid, tartaric acid, methanesulfonic acid, maleic acid or arginine. Other salts include the salt formed with alkali metal or alkaline earth metal (such as sodium, potassium, calcium, or magnesium), existing in the form of esters, carbamates, or other conventional "prodrug" forms. Since the compounds contain one or more asymmetric centers, they may be present in the form of a racemic mixture, a single enantiomer, a single diastereoisomer, cis or trans-isomer.

"Prodrug" of the compound means a compound which can transform to a compound of formula (I) or a salt or solution comprised of a compound of formula (I) by metabolism or chemical reactions in vivo when it is administered properly.

In a preferred embodiment of the present invention, the pharmaceutically acceptable salt of the heptacyclic compound is an arginine salt of the heptacyclic compound, which could be synthesized from Arginine and the heptacyclic compounds.

It should be understood that after the disclosure of the structure of compounds according to the present invention, the compounds of the present invention could be obtained by a variety of methods well known in the art utilizing conventional source materials, for example, the methods of chemical synthesis or extraction from plant, all of which are included in the present invention.

As a preferred embodiment of the present invention, it is provided a process for preparing the heptacyclic compounds. The process comprises condensation, dehydration, intramolecular cyclization and the like. The compound may be prepared as follows: a compound of formula (IV) and a compound of formula (V) are condensed to form a compound of formula (VI), then the compound of formula (VI) is deprotected (for example, the protecting group may selected from the group consisting of methyl, isopropyl, benzyl, tetrahydrofuryl, acetyl, methoxymethyl, t-butyloxymethyl, and trimethylsilyl), dehydrated and intramolecularly cyclized to give the desired compound.

(IV)

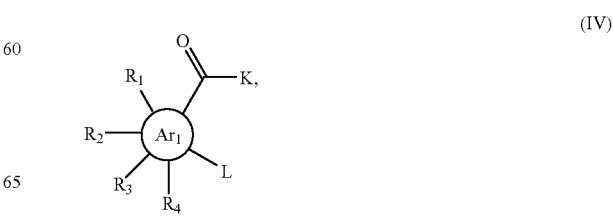

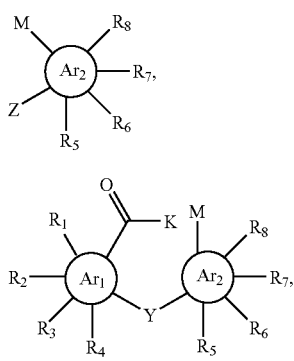

(V)

(VI)

wherein, $Ar_1$, $Ar_2$, X, Y, $R_1$, $R_2$, $R_3$, $R_4$, $R_5$, $R_6$, $R_7$, $R_8$ and Y are the same as defined above; K can be selected from $C_{3-6}$ alkoxy, amino, unsubstituted or substituted aryloxy, unsubstituted or substituted benzyloxy; L can be selected from halogen, $C_{3-6}$ alkoxy, amino, unsubstituted or substituted aryloxy, or unsubstituted or substituted benzyloxy, thiol group; M can be selected from $C_{3-6}$ alkoxy, amino, unsubstituted or substituted aryloxy, unsubstituted or substituted benzyloxy, thiol group; Z can be selected from halogen, $C_{3-6}$ alkoxy, amino, unsubstituted or substituted aryloxy, unsubstituted or substituted benzyloxy, thiol group.

As a preferred embodiment of the present invention, the compound has a structure of Formula (IVa). Preferably, $R_1'$ and $R_8'$ are methyl, $R_3'$ is hydroxyl, $R_4'$ is an aldehyde group, $R_5'$ is carboxyl, $R_7'$ is methoxy. The chemical name is 4-Formyl-3-hydroxy-8-methoxy-1,9-dimethyl-11-oxo-11H-dibenzo[b,e][1,4]dioxepine-6-carboxylic acid (Psoromic acid, F7); wherein $R_1'$, $R_3'$, $R_4'$, $R_5'$, $R_7'$ and $R_8'$ could be converted into other functional groups by methods well known in the art.

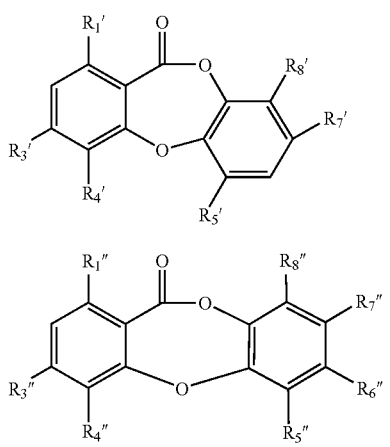

(IVa)

(Va)

Alternatively, the compound has a structure of Formula (Va), wherein $R_1''$ and $R_5''$ are methyl, $R_3''$ and $R_7''$ are hydroxyl, $R_4''$ is an aldehyde group, $R_6''$ is carboxyl, $R_8''$ is ethoxymethyl. The chemical name is 9-ethoxymethyl-4-formyl-3,8-dimethoxy-1,6-dimethyl-11-oxo-11H-dibenzo[b,e][1,4]dioxepine-7-carboxylic acid (G0); wherein $R_1''$, $R_3''$, $R_4''$, $R_5''$, $R_7''$ and $R_8''$ could be converted into other functional groups by methods well known in the art.

The compound of Formula (IVa) or (Va) could be used as starting materials and converted into other functional groups by reactions such as alkylation, acylation, substitution, addition, elimination, rearrangement, oxidation, reduction, and free radical reaction. The compound could also be reacted with a compound of Formula (IX), (X) or (XI):

R-D  (IX), wherein, R is the same as defined in above $R_1$-$R_8$ group except for H, D is a leaving group, such as Cl, Br, I, —$SO_2$—$CH_3$ or —$SO_2$—$(C_6H_5)$-p-$CH_3$;

NHR'R''  (X), wherein, R' and R'' are the same substituents as defined above except for H, R' and R'' could be same or different groups;

R—Mg—Br  (XI), wherein, R has the same meaning as defined in above $R_1$-$R_8$ group except for H.

All of the synthesized compounds could be further purified by column chromatography, HPLC or recrystallisation.

The methology for synthetic chemical transformations and protection of functional groups (protection and deprotection) are helpful for synthesis and use of the compounds and are well known in the prior art, for example as published in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994) and L. Paquette, ed., *Encyclopedia of Reagents for Organic Synthesis*, John Wiley and Sons (1995).

Some of the heptacyclic compounds may also be extracted, isolated and purified from plants. The plants include, but are not limited to, Parmeliaceae, Cladoniaceae, Lecanoraceae, Funariaceae, Stereocaulaceae, Usneaceae and the like. Preferably, the heptacyclic compounds are isolated from *Thamnoia ver-micularis* (Ach.) Asahina or *Lethariella cladonioides*.

As a preferred embodiment of the present invention, the compound of the present invention is psoromic acid, F7, a white needle crystal, which is odorless, faintly bitter, with melting point of 265-266° C. It is slightly soluble in water, acidic with a pH of 3-4, and soluble in organic solvents such as DMSO, ethanol, acetone and ethyl acetate. The compound is stable at room temperature and hydrophilous in air.

A special synthetic method for psoromic acid is shown below:

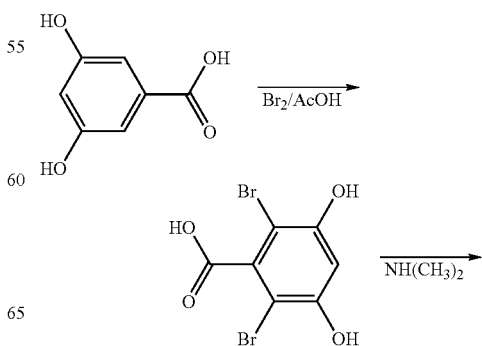

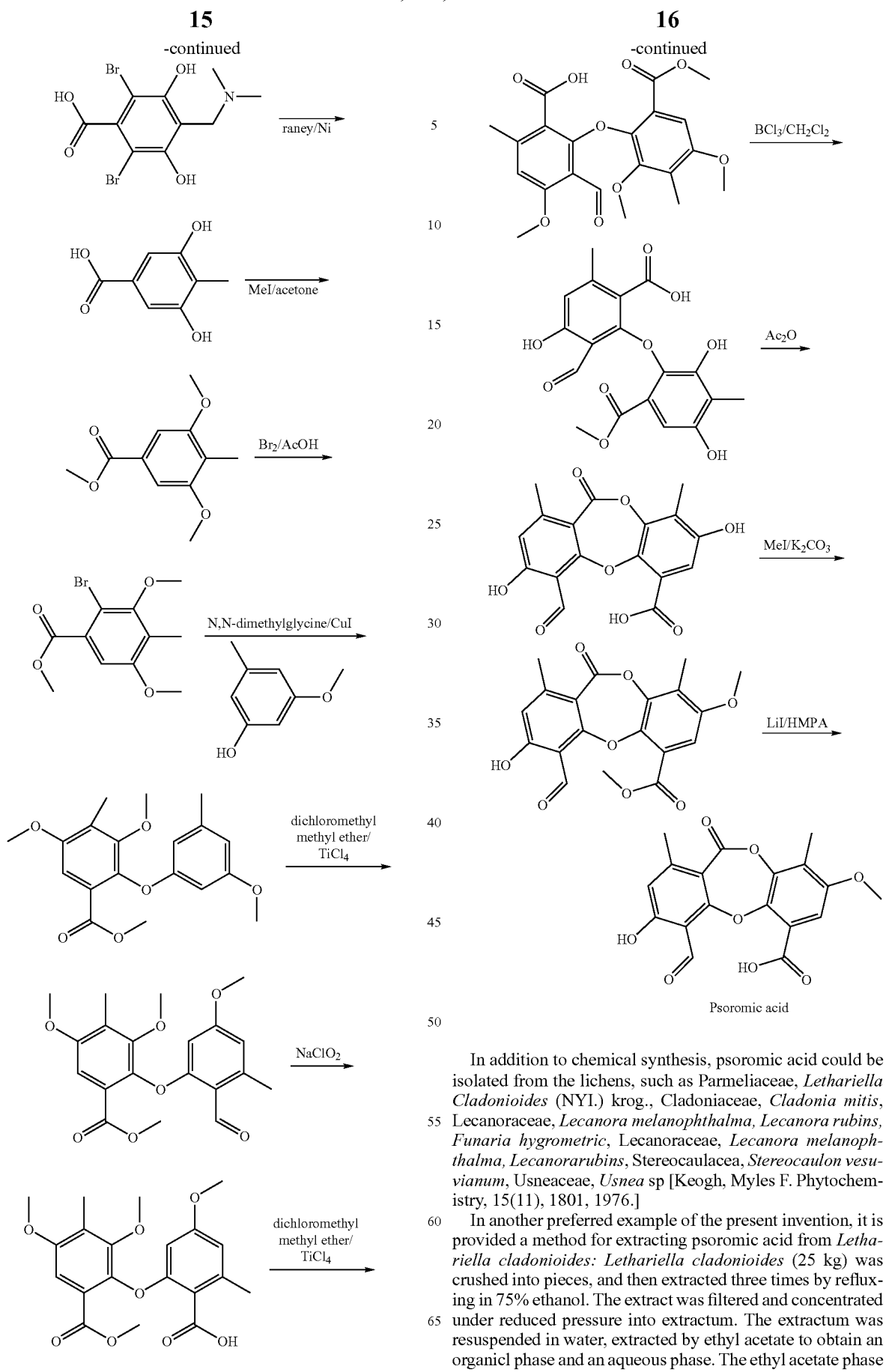

In addition to chemical synthesis, psoromic acid could be isolated from the lichens, such as Parmeliaceae, *Lethariella Cladonioides* (NYI.) krog., Cladoniaceae, *Cladonia mitis*, Lecanoraceae, *Lecanora melanophthalma, Lecanora rubins, Funaria hygrometric*, Lecanoraceae, *Lecanora melanophthalma, Lecanorarubins*, Stereocaulacea, *Stereocaulon vesuvianum*, Usneaceae, *Usnea* sp [Keogh, Myles F. Phytochemistry, 15(11), 1801, 1976.]

In another preferred example of the present invention, it is provided a method for extracting psoromic acid from *Lethariella cladonioides*: *Lethariella cladonioides* (25 kg) was crushed into pieces, and then extracted three times by refluxing in 75% ethanol. The extract was filtered and concentrated under reduced pressure into extractum. The extractum was resuspended in water, extracted by ethyl acetate to obtain an organicl phase and an aqueous phase. The ethyl acetate phase was dissolved in an organic solvent and mixed thoroughly with silica gel (200 to 300 mesh), and then concentrated under reduced pressure to dryness. The silica gel and CH$_2$Cl$_2$ were packed into a column by a wet method and eluted by CH$_2$Cl$_2$, CH$_2$Cl$_2$/MeOH successively. The eluate was condensed under reduced pressure to dryness and then dissolved in methanol and filtered repeatedly. The filtrates was recrystallized from CH$_2$Cl$_2$/EtOH to obtain the purified compound, which was characterized by spectrum to be psoromic acid.

In another preferred example of the present invention, it is provided a method for preparing the heptacyclic compounds and their pharmaceutically acceptable salts from the strafing material psoromic acid F7 or G0. The preparation example is as follows:

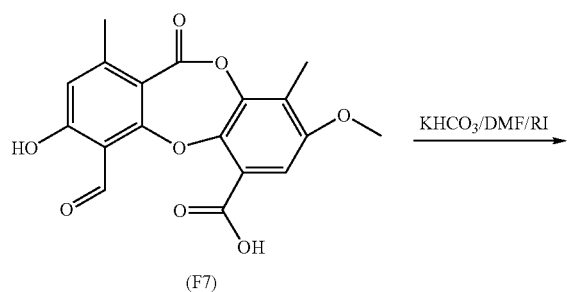

(1)

(F7)

The psoromic acid (1 mmol) was dissolved in anhydrous DMF (10 mL), KHCO$_3$ (2.4 mmol) was added and stirred for several minutes at room temperature. Then, RI or RBr (1.2 mmol) was added. The reaction mixture was kept at 40° C. and monitored by TLC. Upon completion, the reaction mixture was poured into 50 mL of water and extracted with ethyl acetate. The organic layer was subsequently washed with saturated NaHCO$_3$ solution and saturated brine, dried over anhydrous MgSO$_4$, evaporated by a rotary evaporater, and then purified by column chromatography to give a white solid.

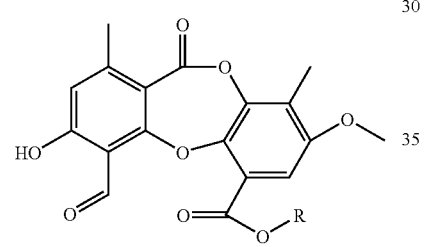

(2)

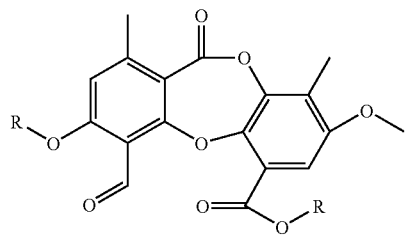

The psoromic acid (1 mmol) was dissolved in anhydrous DMF (10 mL), K$_2$CO$_3$ (2.4 mmol) was added and stirred for several minutes at room temperature. Then, RI or RBr (2.4 mmol) was added. The reaction mixture was kept at 40° C. and monitored by TLC. Upon completion, the reaction mixture was poured into 50 mL of water and extracted with ethyl acetate. The organic layer was subsequently washed with saturated NaHCO$_3$ solution and saturated brine, dried over anhydrous MgSO$_4$, evaporated by a rotary evaporater, and then purified by column chromatography to give a white solid.

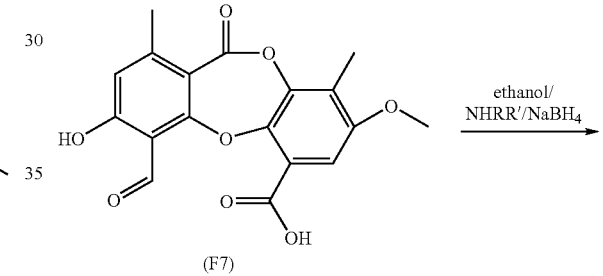

(3)

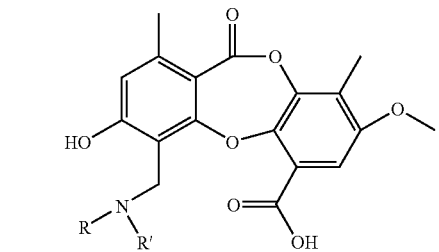

(F7)

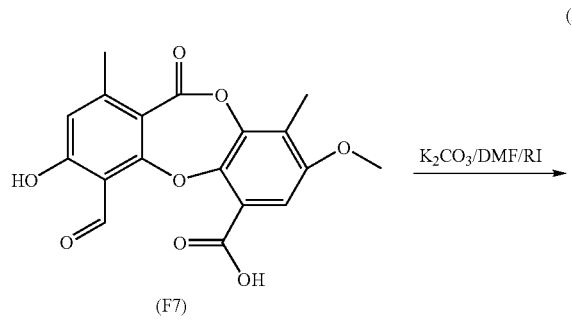

The psoromic acid (1 mmol) was dissolved in ethanol (25 mL), NHRR' (1 mmol) was added and the reaction mixture was stirred for half an hour. Sodium borohydride (4 mmol) was added under ice bath and the mixture was stirred under ice bath for an additional 15 min and then stirred overnight at room temperature. Water (3 mL) was added and the mixture was acidified with diluted HCl to a pH of 6. All of the solvent was removed by rotary evaporation. The residue was redissolved in ethanol, dried over anhydrous magnesium sulfate, filtered, evaporated by a rotary evaporater, and purified by column chromatography to give the product.

(4)

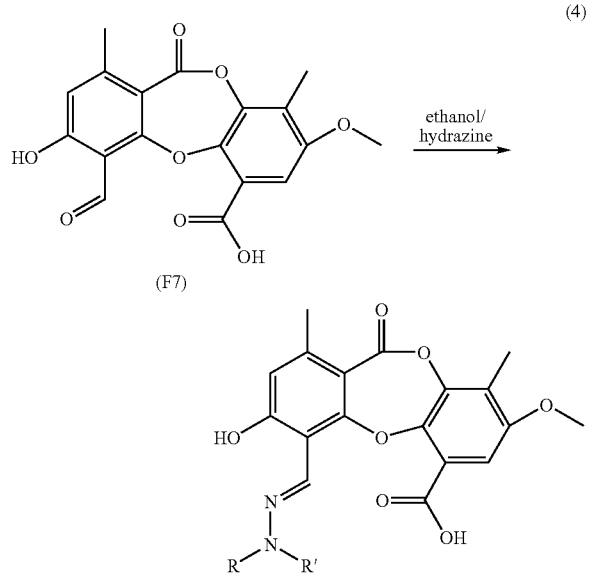

(F7)

ethanol/
hydrazine
→

(5)

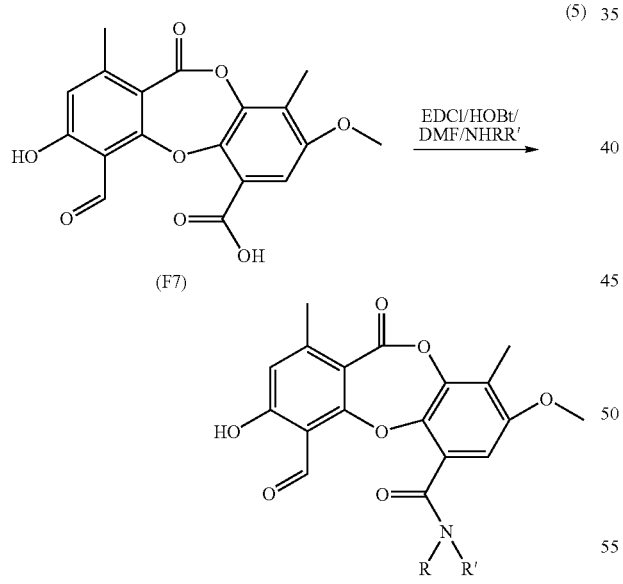

(F7)

EDCI/HOBt/
DMF/NHRR'
→

The psoromic acid (1 mmol) was dissolved in ethanol (25 mL), NH$_2$—NRR' (1 mmol) was added and the reaction mixture was stirred for half an hour. Reaction was monitored by TLC. Upon completion, all of the solvent was removed by rotary evaporation. The residue was redissolved in ethanol, dried over anhydrous magnesium sulfate, filtered, evaporated by a rotary evaporater to give the product.

The psoromic acid (1 mmol), EDCI (1.5 mmol) and HOBt (1.5 mmol) were dissolved in DMF (5 ml) in an ice bath and the solution was stirred for half an hour. A solution of NHRR' (1 mmol) and triethylamine (1 mmol) in anhydrous DMF (3 ml) was added dropwise into the above solution. The reaction was monitored by TLC. Upon completion, the reaction mixture was poured into 60 mL of water and extracted with ethyl acetate. The organic layer was washed with saturated NaHCO$_3$ solution and saturated brine respectively, dried over anhydrous MgSO$_4$, filtered, evaporated by a rotary evaporator, and purified by column chromatography to give the product.

(6)

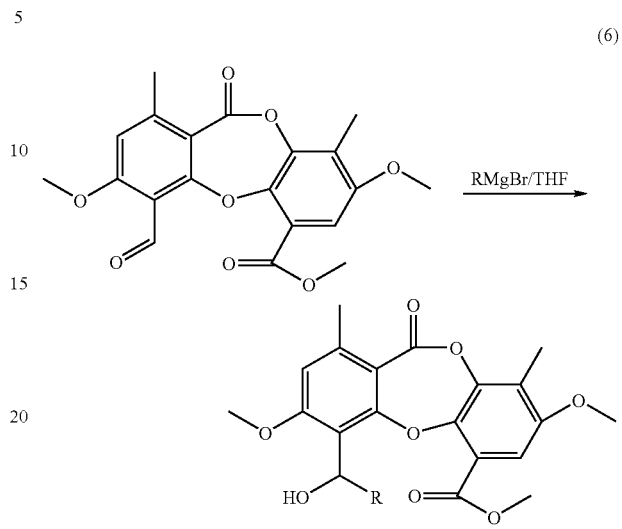

RMgBr/THF
→

The psoromic acid dimethyl ester (0.15 mmol) was dissolved in anhydrous tetrahydrofuran. 2M Grignard reagent (0.7 ml, 1.4 mmol) in tetrahydrofuran was added under ice bath and the mixture was stirred at room temperature for 1 h. Upon completion, 2 ml of 1N hydrochloric acid was added to the reaction mixture and the mixture was extracted with methylene chloride. The organic layer was washed with water and saturated brine, dried over anhydrous MgSO$_4$, filtered and evaporated by a rotary evaporator, and purified by column chromatography to give the product.

(7)

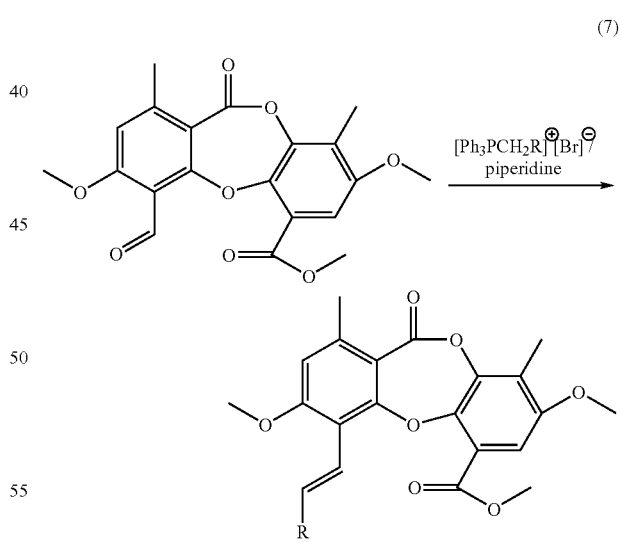

[Ph$_3$PCH$_2$R]$^{\oplus}$[Br]$^{\ominus}$/
piperidine
→

The psoromic acid dimethyl ester (0.24 mmol) and phosphorus ylide (0.48 mmol) were dissolved in 3 ml of toluene. The reaction mixture was heated at 80° C. for 14 hours under nitrogen atmosphere. Upon completion, the reaction mixture was cooled to room temperature and methylene chloride was added. The reaction mixture was washed with 0.1N diluted hydrochloric acid, dried over anhydrous MgSO$_4$, filtered, evaporated by a rotary evaporator, and purified by column chromatography to give the product.

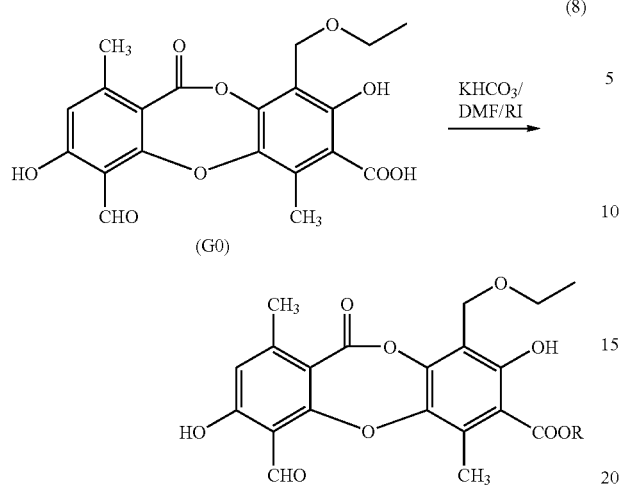

(G0)

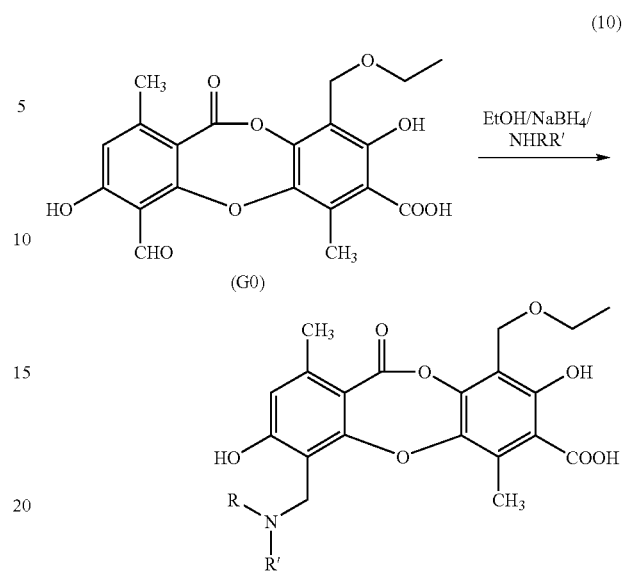

(G0)

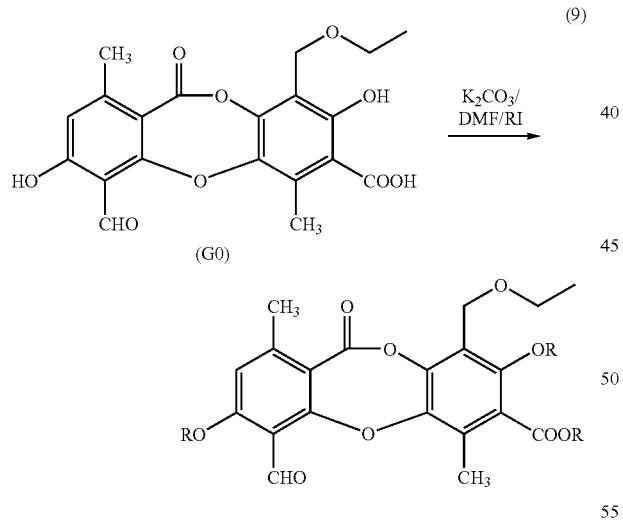

(G0)

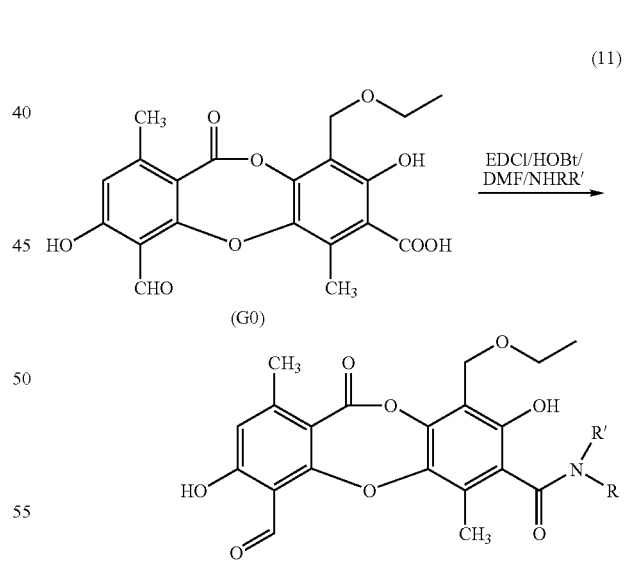

(G0)

G0 (1 mmol) was dissolved in anhydrous DMF (10 mL), KHCO$_3$ (2.4 mmol) was added and the mixture was stirred for several minutes at room temperature. Then, RI or RBr (1.2 mmol) was added. The reaction mixture was kept at 40° C. and monitored by TLC. Upon completion, the reaction mixture was poured into 50 mL of water and extracted with ethyl acetate. The organic layer was subsequently washed with saturated NaHCO$_3$ solution and saturated brine, dried over anhydrous MgSO$_4$, evaporated by a rotary evaporator and purified by column chromatography to give a white solid.

G0 (1 mmol) was dissolved in ethanol (25 mL), NHRR' (1 mmol) was added and the reaction mixture was stirred for half an hour. Sodium borohydride (4 mmol) was added under ice bath; the mixture was stirred in an ice bath for an additional 15 min and then stirred overnight at room temperature. Water (3 mL) was added, and the mixture was acidified with diluted HCl until pH 6. All of the solvent was removed by rotary evaporation. The residue was redissolved in ethanol, dried over magnesium sulfate, filtered, evaporated by a rotary evaporater, purified by column chromatography to give the product.

G0 (1 mmol) was dissolved in DMF (10 mL), K$_2$CO$_3$ (2.4 mmol) was added and the mixture was stirred for several minutes at room temperature. Then, RI or RBr (2.4 mmol) was added. The reaction mixture was kept at 40° C. and monitored by TLC. Upon completion, the reaction mixture was poured into 50 mL of water and extracted with ethyl acetate. The organic layer was subsequently washed with saturated NaHCO$_3$ solution and saturated brine, dried over anhydrous MgSO$_4$, evaporated by a rotary evaporator and purified by column chromatography to give a white solid.

G0 (1 mmol), EDCI (1.5 mmol) and HOBt (1.5 mmol) were dissolved in DMF (5 ml) in an ice bath and the solution was stirred for half an hour. A solution of NHRR' (1 mmol) and triethylamine (1 mmol) in anhydrous DMF (3 ml) was added dropwise to the above solution. The reaction was monitored by TLC. Upon completion, the reaction mixture was poured into 60 mL of water and extracted with ethyl acetate. The organic layer was washed with saturated NaHCO$_3$ solution and saturated brine respectively, dried over anhydrous MgSO$_4$, filtered and evaporated by a rotary evaporator, and purified by column chromatography to give the product.

In another preferred embodiment of the present invention, it is provided a process for preparing the heptacyclic compounds and their pharmaceutically acceptable salts from corresponding bromides and phenols through Ullmann reaction and intramolecular cyclization reaction.

Usage

Based on the new discovery of the present inventors, the invention provides a use of the compound of Formula I, or isomers, racemates, pharmaceutically acceptable salts thereof in the manufacture of a medicament for preventing and treating diabetes or metabolic syndrome in mammals. The metabolic syndrome include, but are not limited to, diabetes, insulin resistance, hyperinsulinemia, abnormal glucose tolerance, obesity, adiposis hepatica, hyperuricacidemia, arthrolithiasis, hyperlipemia, hypercholesteremia, artherosclerosis or hypertension. The common characteristic of these diseases is the metabolism disorder of glucose, lipid and protein.

Compositions

As used herein, the term "the present compositions" include (be not limited to): pharmaceutical compositions, food replenishers or health products containing heptacyclic compounds of the present invention as active ingredients for preventing and treating diabetes and metabolic syndrome.

The present invention also provides a composition comprising (a) an effective amount of a compound of Formula I, or isomers, racemates, pharmaceutically acceptable salts thereof or their mixtures; and (b) a bromatologically or pharmaceutically acceptable carrier or excipient.

As used herein, the term "contain" or "comprise" means that each component can be combined together in the mixture or composition of the present invention. Thus, the term "be mainly consisted of" and "be consisted of" is included in the term "contain" or "comprise".

The term "pharmaceutically acceptable" means a substance which can be applied to humans and/or animals without undue side effects such as toxicity, irritation, allergic response, and the like, commensurate with a reasonable benefit/risk ratio.

As use herein, "pharmaceutically acceptable carrier" or "bromatologically acceptable carrier" refers to a pharmaceutically or bromatologically acceptable solvent, suspending agent or excipient that can deliver the heptacyclic compound of the present invention, or isomers, racemates, pharmaceutically acceptable salts thereof or their mixtures to animals or humans. The carrier could be a liquid or a solid.

The composition according to the present invention comprises 1-200 parts by weight of the compound of Formula (I) or the pharmaceutically acceptable salts thereof; and 10-5000 parts by weight of pharmaceutically acceptable carriers or excipients. Preferably, the composition comprises 5-150 parts by weight of the compound of Formula I or pharmaceutically acceptable salts thereof; and 30-2000 parts by weight of pharmaceutically acceptable carriers or excipients.

The composition of the present invention can be used in combination with one or more other substances which are effective for diabetes or metabolic syndrome. Therefore, the composition may further comprise (c) one or more drugs selected from the group consisting of antidiabetic drugs, hypolipidemic drugs, weight-reducing aid, antihypertensive drug, and antithrombotic drug. When two or more drugs are administered in combination, the effect is generally better than that of a single drug.

In a preferred embodiment of the present invention, the antidiabetic drugs can be selected from Biguanides, Sulfonylureas, Glinides, α-glucosidase inhibitors, Euglycemic agents (such as thiazolidinediones), aP2 inhibitors, DPPIV inhibitors, SGLT2 inhibitors, Insulin, Glucagon-like peptide-1 (GLP-1) or their analogues; or the hypolipidemic drugs can be selected from MTP inhibitors, HMG-CoA Reductase inhibitors, squalene synthetase inhibitors, fibrates, acyl CoA-cholesterol acyltransferase (ACAT) inhibitors, lipoxygenase inhibitors, cholesterol absorption inhibitor, cholic acid/sodium cholate Cotransporter inhibitors, low density lipoprotein receptor activity up-regulators, cholic acid sequestrant, Nicotinic Acid or their derivatives; or the weight-reducing aids can be selected from β3-adrenergic agonists, lipidase inhibitors, serotonin reuptake inhibitors, aP2 inhibitors, thyroid receptor agonists, cannabis receptor CB-1 antagonist or their derivatives; or the antihypertensive drugs can be selected from ACE inhibitors, angiotensin II receptor antagonist, calcium channel blocking agents, beta-adrenergic blockers or diuretics; or the anticoagulant drugs can be selected from Platelet Aggregation Inhibitors.

When the composition comprises two or more active ingredients, it may comprise 1-200 parts by weight of the compound of Formula (I), or isomers, racemates, pharmaceutically acceptable salts thereof or their mixtures; 1-500 parts by weight of one or more drugs selected from antidiabetic drugs, hypolipidemic drugs, weight-reducing aids, antihypertensive drugs, antithrombotic drugs; and 10-5000 parts by weight of pharmaceutically acceptable carriers or excipients. Preferably, the composition comprises 5-150 parts by weight of the compound of Formula (I), or pharmaceutically acceptable salts thereof; 5-250 parts by weight of one or more drugs selected from antidiabetic drugs, hypolipidemic drugs, weight-reducing aids, antihypertensive drugs, antithrombotic drugs; and 30-2000 parts by weight of pharmaceutically acceptable carriers or excipients.

The pharmaceutical composition of the present invention could be in a variety of dosage forms, as long as they can effectively deliver the active ingredients into mammals. The dosage form can be selected from tablets, capsules, powders, granules, syrups, solutions, suspensions or aerosols. The heptacyclic compounds could exist in suitable carriers or dilutions, and the carriers or dilutions can be solids or liquids.

From the standpoint of ease of preparation and administration, the preferred pharmaceutical composition is a solid composition, especially tablets and solid- or liquid-filled capsules. Oral administration of the pharmaceutical composition is preferred.

The heptacyclic compound and its composition can also be stored in sterile appliances suitable for injection or infusion. In the pharmaceutical composition of the present invention, the active ingredients typically constitute 1-50% (preferably 2-40%, more preferably 3-30%) based on the total weight of the composition, the remainders of which are pharmaceutically acceptable carriers or other additives.

When the compound or composition is used for the above purposes, they may be mixed with one or more pharmaceutically acceptable carriers or excipients, such as solvents, diluents or the like, and may be orally administered in the form of tablets, capsules, dispersible powders, granules or suspensions (containing, for example, 0.05-5% of suspending agent), syrups (containing, for example, 10-50% of sugar), elixirs (containing, for example, 20-50% of ethanol), or may be parenteral administered in the form of sterile injectable solutions or suspensions (containing about 0.05-5% of suspending agent in an isotonic medium). For example, the pharmaceutical formulations may comprise 1-50% by weight, typically 2-40% by weight of active ingredient admixed with carriers.

The effective amount of the active ingredient may vary with the particular compound used, administration mode and the severity of the disease to be treated. However, satisfactory effect may be obtained when the compound of the present invention is administered at a dosage of about 0.1 to about 1000 milligrams per kilogram of animal body weight per day. Preferably, the compound of the present invention is administered in separate dosages 1-3 times per day or administered in sustained-release formulation. For most of the large mammals, a total daily dosage is about 5 to 6000 mg, preferably, about 10 to 1000 mg. Dosage forms suitable for internal use contain about 1 to 200 mg of active compound intimately admixed with solid or liquid carriers. This dosage regimen can be adjusted to provide best treatment responses. For example, according to the urgent requirement of the conditions being treated, the dosage may be divided into several separate parts for daily administration, or the dosage may be reduced proportionally.

The compound or its pharmaceutically acceptable salts, as well as compositions containing the same can be administered orally, intravenously, intramuscularly, subcutaneously and the like. Oral administration is preferred. Solid carriers include starch, lactose, bicalcium phosphate, microcrystalline cellulose, sucrose and bolus alba, while liquid carriers include sterile water, polyethylene glycol, nonionic surfactant and edible oil (such as corn oil, arachis oil and benne oil), as long as they are suitable for properties of the active ingredients and the particular administration mode as desired. Adjuvants typically used in the preparation of a pharmaceutical composition could also be advantageously included, for example, flavoring agent, pigment, antiseptic and antioxidant such as vitamin E, vitamin C, BHT and BHA.

The active compound or its pharmaceutically acceptable salts as well as compositions containing the same can also be administered parenterally or intraperitoneally. Solutions or suspensions of these active compounds (as a free base or a pharmaceutically acceptable salt) can also be prepared in water mixed with suitable surfactants (such as hydroxypropyl cellulose). Dispersions can also be prepared in glycerin, liquid, polyethylene glycol, and a mixture of polyethylene glycol in oil. Under ordinary conditions of storage and use, these preparations contain preservatives to prevent the growth of microorganisms.

The pharmaceutical forms suitable for injection include sterile aqueous solutions or dispersions and sterile powders (for the extemporaneous preparation of sterile injectable solutions or dispersions). In all cases, the forms must be sterile and must be fluid for the ease of syringes to discharge contents. It must be stable under the conditions of manufacture and storage and must be preserved against any contamination of microorganisms such as bacteria and fungi. The carrier can be a solvent or dispersion medium containing, for example, water, alcohol (e.g. glycerol, propylene glycol and liquid polyethylene glycol), suitable mixtures thereof, and vegetable oils.

The main advantages of the invention are as follows: the present inventors found for the first time a new use of the compound of Formula (I) in the treatment of diabetes or metabolic syndrome, wherein the compound not only has strong pharmacologic actions, showing good hypoglycemic, hypolipidemic effect, as well as antiobesity actions, but also can remarkably improve fatty liver and arthrolithiasis, thus having an excellent pharmaceutical prospect.

The invention is further illustrated in conjunction with the following examples. It is appreciated that these examples are only intended to illustrate the invention, but not to limit the scope of the invention. For the experimental methods in the following examples, they are performed under routine conditions, or as instructed by the manufacturers, unless otherwise specified.

Example 1

4-Formyl-3-hydroxy-8-methoxy-1,9-dimethyl-11-oxo-11H-dibenzo[b,e][1,4]dioxepine-6-carboxylic acid (psoromic acid) (Compound No: F7)

1 mmol of 2,4-dihydroxybenzoic acid was taken in 2 ml of chloroform, and a solution of 2 mmol of bromine in 0.5 ml of chloroform was added from a pressure-equalizing dropping funnel at room temperature over a period of 1.5 h. A NaOH trap system was provided on top of the addition funnel. The mixture was then stirred for 5 h and filtered. The filter cake was washed with chloroform and then with water. The precipitate was 2,6-Dibromo-3,5-dihydroxybenzoic Acid (97%): $^1$H NMR (DMSO-$d_6$) δ 6.69 (s, 1H).

To a stirred mixture of 37% of aqueous formaldehyde solution (2 mmol), absolute ethanol (0.4 mL), and glacial acetic acid (0.8 mL) was added 40% of aqueous dimethylamine (2 mmol) solution under ice bath (25° C.). The ice bath was removed and 2,6-Dibromo-3,5-dihydroxybenzoic Acid (1 mmol) was added over a period of 2 min. The mixture became darkened, and after 5 min a white solid began to appear. The mixture was stirred at 25° C. for 24 h and then at 0° C. for 2 h to allow complete precipitation of product. The precipitate was washed with ice-cold acetone (2×0.5 mL), dried under oil pump to give 2,6-Dibromo-3,5-dihydroxy-4[(dimethylamino) methylene]-benzoic Acid (98%): $^1$H NMR (DMSO-$d_6$) δ 3.92 (s, 2H), 2.41 (s, 6H).

To a stirred solution of 2,6-Dibromo-3,5-dihydroxy-4[(dimethylamino) methylene]-benzoic Acid (1 mmol) in 2.5 mL of 3 N NaOH under nitrogen was added 0.345 g of Raney nickel in portions over a period of 1 h. The mixture was then stirred at 25° C. for about 12 h and filtered. The filter cake was washed with water (2×5 mL), and the combined filtrates were acidified to a pH of 1 with concentrated HCl to give a pale yellow or light purple solution. The solution was extracted with ethyl acetate, and the combined organic extracts were washed with saturated NaCl solution (2×0.2 mL), dried over sodium sulphate and evaporated by a rotatory evaporator to give 3,5-Dihydroxy-4-methylbenzoic Acid (70%) as a white solid: $^1$H NMR (DMSO-$d_6$) δ 6.90 (s, 2H), 1.95 (s, 3H).

1 mmol of 3,5-Dihydroxy-4-methylbenzoic Acid was dissolved in 3 mL of acetone, and then 3.6 mmol of $K_2CO_3$ and 3.6 mmol of $CH_3I$ were added. The mixture was allowed to react at 40° C. and monitored by TLC. Upon completion, the reaction mixture was filtered to remove $K_2CO_3$, and evaporated by a rotatory evaporator to remove acetone. The mixture was then purified by column chromatography to give 3,5-Dimethoxy-4-methyl-benzoic acid methyl ester (90%): $^1$H NMR (CDCl$_3$) δ 3.97 (s, 3H), 3.79 (s, 6H), 2.32 (s, 3H).

3,5-Dimethoxy-4-methyl-benzoic acid methyl ester (1 mmol) was taken in 2 mL of dichloromethane, and a solution of bromine (1 mmol) in 0.5 mL of dichloromethane was added from a pressure-equalizing dropping funnel at room temperature over a period of 1.5 h. A NaOH trap system was provided on top of the addition funnel. The mixture was then stirred for 5 h and the solvent was evaporated off to give 2-Bromo-3,5-dimethoxy-4-methyl-benzoic acid methyl ester (95%).

1 mmol of 3,5-Dihydroxy-toluene was taken in 3 mL of acetone, and then 3 mmol of $K_2CO_3$ was added and stirred for several minutes. Then, a solution of $CH_3I$ (3 mmol) in 10 ml of acetone was added from a pressure-equalizing dropping funnel, and the reaction was monitored by TLC. Upon completion, the reaction mixture was filtered to remove $K_2CO_3$, and evaporated by a rotary evaporator to remove acetone. The mixture was then purified by column chromatography to give 5-methyl-3-methoxy-phenol (80%).

A mixture of 1 mmol of 2-Bromo-3,5-dimethoxy-4-methyl-benzoic acid methyl ester, 1.5 mmol of 3-methoxy-5-methylphenol, 2 mmol of $Cs_2CO_3$, 1 mmol of CuI, and 1 mmol of N,N-dimethylglycine was added to 4 mL of dioxane under nitrogen atmosphere, and then the mixture was heated to 90° C. and monitored by TLC. Upon completion, water was added and the mixture was extracted with ethyl acetate. The organic layer was washed with saturated brine, dried over $Na_2SO_4$, and evaporated by a rotary evaporator. The residue was purified by column chromatography to afford 3,5-Dimethoxy-2-(5-methyl-3-methoxy-phenoxy)-4-methyl-benzoic acid methyl ester (50%): $^1$H NMR (DMSO-$d_6$) δ 7.18 (s, 1H), 6.35 (s, 1H), 6.22 (t, 1H, J=2 Hz), 6.18 (bs, 1H), 3.88 (s, 3H), 3.75 (s, 6H), 3.73 (s, 3H), 2.24 (s, 3H), 2.18 (s, 3H).

A mixture of 1 mmol of 3,5-dimethoxy-2-(5-methyl-3-methoxy-phenoxy)-4-methyl-benzoic acid methyl ester and 6 mmol of dichloromethyl methyl ether was taken in 8 mL of dichloromethane. The mixture was cooled to −78° C. under stirring, and then titanium tetrachloride (6 mmol) in dichloromethane (4 ml) was added dropwise over 0.5 h. Upon completion, the reaction mixture was poured into ice-cold water and partitioned. The layers were separated, and the aqueous layer was extracted with dichloromethane. The combined organic layers were dried over $MgSO_4$, and the solvent was evaporated by a rotary evaporator. The residue was purified by column chromatography to afford 2-(3-methyl-2-Formyl-5-methoxy-phenoxy)-3,5-dimethoxy-4-methyl-benzoic acid methyl ester (60%).

A solution of 2-(3-methyl-2-Formyl-5-methoxy-phenoxy)-3,5-dimethoxy-4-methyl-benzoic acid methyl ester (1 mmol) and sulfamic acid (3 mmol) in 7 mL of $H_2O$:THF:DMSO (20:10:1) at 0° C. was treated with $NaClO_2$ (3 mmol) in 1 mL of $H_2O$. The reaction mixture was stirred for 20 min at 0° C. The reaction was diluted with EtOAc (30 mL), washed with saturated aqueous $NH_4Cl$ (2×15 mL) and saturated brine, and dried ($Na_2SO_4$). Evaporation of the solvents under reduced pressure and further purification by column chromatography gave 2-(3-methyl-2-carboxy-5-methoxy-phenoxy)-3,5-dimethoxy-4-methyl-benzoic acid methyl ester (85%).

2-(3-methyl-2-carboxy-5-methoxy-phenoxy)-3,5-dimethoxy-4-methyl-benzoic acid methyl ester (1 mmol) and dichloromethyl methyl ether (2 mmol) were taken in anhydrous dichloromethane (2 ml). The mixture was stirred and cooled to −10° C. in an ice-salt bath. Titanium tetrachloride (2.5 mmol) in dichloromethane (0.5 ml) was then added dropwise over 0.5 h. Stirring was continued for a further 1.5 h at −10° C. and then for 1.5 h at room temperature. To the reaction mixture was then added cold, dilute hydrochloric acid, and the reaction mixture was extracted with dichloromethane. The organic layer was washed with water, brine and then dried ($MgSO_4$). The solvent was evaporated by a rotary evaporator and the residue was purified by column chromatography to afford 2-(3-methyl-6-Formyl-2-carboxy-5-methoxy-phenoxy)-3,5-dimethoxy-4-methyl-benzoic acid methyl ester (63%).

A solution of boron trichloride (3 mmol) in dichloromethane (0.4 ml) was added dropwise to a stirred solution of 2-(3-methyl-6-formyl-2-carboxy-5-methoxy-phenoxy)-3,5-dimethoxy-4-methyl-benzoic acid methyl ester (1 mmol) in dichloromethane (3 ml) under ice bath. The mixture was stirred under ice bath for 20 min and then at room temperature for 2 h. Upon completion, the mixture was poured into ice water and extracted with dichloromethane, and the residue was purified by column chromatography to afford 2-(3-methyl-6-formyl-2-carboxy-5-hydroxy-phenoxy)-3,5-dihydroxy-4-methyl-benzoic acid methyl ester (87%).

Dry 2-(3-methyl-6-formyl-2-carboxy-5-hydroxy-phenoxy)-3,5-dihydroxy-4-methyl-benzoic acid methyl ester (1 mmol) was added to acetic anhydride (15 ml) and the resulting mixture was refluxed for five hours at 145° C. The excess acetic anhydride was distilled out. The residue was added with crushed ice and then extracted with ethyl acetate. The combined extracts were washed successively with saturated $NH_4Cl$ solution and water, dried over anhydrous $Na_2SO_4$, concentrated and purified by column chromatography to afford 4-formyl-3,8-dihydroxy-1,9-dimethyl-11-oxo-11H-dibenzo[b,e][1,4]dioxepine-6-carboxylic acid methyl ester (30%).

1 mmol of 4-Formyl-3,8-dihydroxy-1,9-dimethyl-11-oxo-11H-dibenzo[b,e][1,4]dioxepine-6-carboxylic acid methyl ester was dissolved in 3 mL of acetone, 1 mmol $K_2CO_3$ was added and stirred for several minutes. Then, 1 mmol of $CH_3I$ in acetone was added from a pressure-equalizing dropping funnel. The reaction mixture was monitored by TLC. Upon completion, the reaction mixture was filtered to remove $K_2CO_3$ and evaporated by a rotatory evaporator to remove acetone. The residue was purified by column chromatography to give 4-formyl-3-hydroxy-8-methoxy-1,9-dimethyl-11-oxo-11H-dibenzo[b,e][1,4]dioxepine-6-carboxylic acid methyl ester (84%).

4-Formyl-3-hydroxy-8-methoxy-1,9-dimethyl-11-oxo-11H-dibenzo[b,e][1,4]dioxepine-6-carboxylic acid methyl ester (42.0 mg) and lithium iodide (250 mg) were taken in hexamethylphosphoric triamide (5 ml). The mixture was stirred at 90° C. for 5 h and then lithium iodide (250 mg) was added again. The mixture was heated at 90° C. for 21 h. When the reaction was completed, the mixture was cooled and poured into hydrochloric acid cooled by an ice bath. The mixture was extracted with ethyl acetate. The organic extract was washed in turn with water, saturated aqueous sodium thiosulphate, and finally saturated brine, and was dried over anhydrous magnesium sulfate. The crude product was crystallized from dimethylسulphoxide to afford psoromic acid, m.p. 264-265° C., $^1$HNMR (300 MHz, $d_6$-DMSO): δ 2.20 (s, 3H), 2.46 (s, 3H), 3.83 (s, 3H), 6.83 (s, 1H), 7.08 (s, 1H), 10.46 (s, 1H).

Example 2

4-Formyl-3-hydroxy-8-methoxy-1,9-dimethyl-11-oxo-11H-dibenzo[b,e][1,4]dioxepine-6-carboxylic acid methyl ester (Compound No:A0)

Psoromic acid (1 mmol) was dissolved in DMF (10 mL), $KHCO_3$ (2.4 mmol) was added and stirred for several minutes at room temperature. Then, $CH_3I$ (1.2 mmol) was added. The reaction mixture was maintained at 40° C. and monitored by TLC. Upon completion, the reaction mixture was poured into 50 mL of water and extracted with ethyl acetate. The organic layer was subsequently washed with saturated $NaHCO_3$ solution and saturated brine, and dried over anhydrous $MgSO_4$, filtered and evaporated by a rotatory evaporator. The residue was purified by column chromatography to provide a white solid product.

$^1$HNMR (300 MHz, $d_6$-DMSO): δ 2.29 (s, 3H), 2.52 (s, 3H), 3.85 (s, 3H), 3.92 (s, 3H), 6.67 (s, 1H), 7.04 (s, 1H), 10.51 (s, 1H), 12.38 (s, 1H).

Example 3

4-Formyl-3,8-dimethoxy-1,9-dimethyl-11-oxo-11H-dibenzo[b,e][1,4]dioxepine-6-carboxylic acid methyl ester (Compound No:A1)

Psoromic acid (1 mmol) was dissolved in DMF (10 mL), $K_2CO_3$ (2.4 mmol) was added and stirred for several minutes at room temperature. Then, $CH_3I$ (2.4 mmol) were added. The reaction mixture was maintained at 40° C. and monitored by TLC. Upon completion, the reaction mixture was poured into 50 mL of water and extracted with ethyl acetate. The organic layer was subsequently washed with saturated $NaHCO_3$ solution and saturated brine, dried over anhydrous $MgSO_4$, evaporated by a rotatory evaporator and purified by column chromatography to give a white solid product.

$^1$HNMR (300 MHz, $d_6$-DMSO): δ 2.20 (s, 3H), 2.45 (s, 3H), 3.30 (s, 3H), 3.83 (s, 3H), 3.85 (s, 3H), 6.86 (s, 1H), 7.11 (s, 1H), 10.33 (s, 1H).

Example 4

4-Formyl-3-hydroxy-8-methoxy-1,9-dimethyl-11-oxo-11H-dibenzo[b,e][1,4]dioxepine-6-carboxylic acid ethyl ester (Compound No:A2)

This compound was prepared by means of a procedure similar to that used for Example 2 except replacing $CH_3I$ with $CH_3CH_2I$.

$^1$HNMR (300 MHz, $CD_3OD$): δ 1.37 (t, 3H, J=7.2 Hz), 2.28 (s, 3H), 2.51 (s, 3H), 3.85 (s, 3H), 4.38 (q, 2H, J=7.2 Hz), 6.67 (s, 1H), 7.00 (s, 1H), 10.52 (s, 1H), 12.39 (s, 1H).

Example 5

3-Ethoxy-4-formyl-8-methoxy-1,9-dimethyl-11-oxo-11H-dibenzo[b,e][1,4]dioxepine-6-carboxylic acid ethyl ester (Compound No:A3)

This compound was prepared by means of a procedure similar to that used for Example 3 except replacing $CH_3I$ with $CH_3CH_2I$.

$^1$HNMR (300 MHz, $CD_3OD$): δ 1.34~1.45 (m, 6H), 2.24 (s, 3H), 2.50 (s, 3H), 3.81 (s, 3H), 4.20 (q, 2H), 4.38 (q, 2H), 6.91 (s, 1H), 6.97 (s, 1H), 10.40 (s, 1H).

Example 6

4-Formyl-3-hydroxy-8-methoxy-1,9-dimethyl-11-oxo-11H-dibenzo[b,e][1,4]dioxepine-6-carboxylic acid propyl ester (Compound No:A4)

This compound was prepared by means of a procedure similar to that used for Example 2 except replacing $CH_3I$ with propyl iodide.

$^1$HNMR (300 MHz, $d_6$-DMSO): δ 0.97 (t, 3H, J=7.5 Hz), 1.72 (m, 2H), 2.28 (s, 3H), 2.51 (s, 3H), 3.83 (s, 3H), 4.29 (t, 2H, J=6.9 Hz), 6.67 (s, 1H), 7.00 (s, 1H), 10.51 (s, 1H), 12.40 (s, 1H).

Example 7

4-Formyl-8-methoxy-1,9-dimethyl-11-oxo-3-propoxy-11H-dibenzo[b,e][1,4]dioxepine-6-carboxylic acid propyl ester (Compound No:A5)

This compound was prepared by means of a procedure similar to that used for Example 3 except replacing $CH_3I$ with propyl iodide.

Example 8

4-Formyl-3-hydroxy-8-methoxy-1,9-dimethyl-11-oxo-11H-dibenzo[b,e][1,4]dioxepine-6-carboxylic acid butyl ester (Compound No:A6)

This compound was prepared by means of a procedure similar to that used for Example 2 except replacing $CH_3I$ with butyl iodide.

$^1$HNMR (300 MHz, $d_6$-DMSO): δ 0.97 (t, 3H, J=7.5 Hz), 1.42 (m, 2H), 1.72 (m, 2H), 2.28 (s, 3H), 2.51 (s, 3H), 3.83 (s, 3H), 4.29 (t, 2H, J=6.9 Hz), 6.67 (s, 1H), 7.00 (s, 1H), 10.51 (s, 1H), 12.40 (s, 1H).

Example 9

3-Butoxy-4-formyl-8-methoxy-1,9-dimethyl-11-oxo-11H-dibenzo[b,e][1,4]dioxepine-6-carboxylic acid butyl ester (Compound No:A7)

This compound was prepared by means of a procedure similar to that used for Example 3 except replacing $CH_3I$ with butyl iodide.

$^1$HNMR (300 MHz, $d_6$-DMSO): δ 0.87~0.92 (t, d, 6H), 1.34~1.44 (m, 4H), 1.63~1.71 (m, 4H), 2.17 (s, 3H), 2.47 (s, 3H), 3.80 (s, 3H), 4.12 (t, 2H), 4.23 (t, 2H), 6.78 (s, 1H), 7.07 (s, 1H), 10.31 (s, 1H).

Example 10

4-Formyl-3-hydroxy-8-methoxy-1,9-dimethyl-11-oxo-11H-dibenzo[b,e][1,4]dioxepine-6-carboxylic acid pentyl ester (Compound No:A8)

This compound was prepared by means of a procedure similar to that used for Example 2 except replacing $CH_3I$ with pentyl iodide.

$^1$HNMR (300 MHz, $d_6$-DMSO): δ 0.85 (t, 3H), 1.25~1.35 (m, 4H), 1.68 (t, 2H), 2.19 (s, 3H), 2.44 (s, 3H), 3.83 (s, 3H), 4.26 (t, 2H), 6.86 (s, 1H), 7.07 (s, 1H), 10.32 (s, 1H).

Example 11

4-Formyl-8-methoxy-1,9-dimethyl-11-oxo-3-pentyloxy-11H-dibenzo[b,e][1,4]dioxepine-6-carboxylic acid pentyl ester (Compound No:A9)

This compound was prepared by means of a procedure similar to that used for Example 3 except replacing $CH_3I$ with pentyl iodide.

$^1$HNMR (300 MHz, $d_6$-DMSO): δ 0.83~0.89 (m, 6H), 1.27~1.42 (m, 8H), 1.62~1.78 (m, 4H), 2.17 (s, 3H), 2.44 (s, 3H), 3.80 (s, 3H), 4.11 (t, 2H), 4.22 (t, 2H), 6.97 (s, 1H), 7.05 (s, 1H), 10.31 (s, 1H).

Example 12

4-Formyl-3-hydroxy-8-methoxy-1,9-dimethyl-11-oxo-11H-dibenzo[b,e][1,4]dioxepine-6-carboxylic acid benzyl ester (Compound No:B0)

This compound was prepared by means of a procedure similar to that used for Example 2 except replacing $CH_3I$ with benzyl bromide.

$^1$HNMR (300 MHz, $d_6$-DMSO): δ 2.19 (s, 3H), 2.44 (s, 3H), 3.81 (s, 3H), 5.34 (s, 2H), 6.84 (s, 1H), 7.11 (s, 1H), 7.20~7.51 (m, 5H), 10.29 (s, 1H).

Example 13

3-Benzyloxy-4-formyl-8-methoxy-1,9-dimethyl-11-oxo-11H-dibenzo[b,e][1,4]dioxepine-6-carboxylic acid benzyl ester (Compound No:B1)

This compound was prepared by means of a procedure similar to that used for Example 3 except replacing $CH_3I$ with benzyl bromide.

Example 14

4-Formyl-3-hydroxy-8-methoxy-1,9-dimethyl-11-oxo-11H-dibenzo[b,e][1,4]dioxepine-6-carboxy-(1-ethoxycarboxyl)-ethyl acetate (Compound No:B2)

This compound was prepared by means of a procedure similar to that used for Example 2 except replacing $CH_3I$ with ethyl 2-bromopropionate.

$^1$HNMR (300 MHz, $CD_3OD$): δ 1.22 (t, 3H), 1.51 (d, 3H), 2.22 (s, 3H), 2.45 (s, 3H), 3.84 (s, 3H), 4.18 (q, 2H), 5.21 (q, 1H), 6.85 (s, 1H), 7.13 (s, 1H), 10.25 (s, 1H).

Example 15

3-(1-Ethoxycarboxyl-ethoxy)-4-formyl-8-methoxy-1,9-dimethyl-11-oxo-11H-dibenzo[b,e][1,4]dioxepine-6-carboxy-(1-ethoxycarboxyl)-ethyl acetate (Compound No:B3)

This compound was prepared by means of a procedure similar to that used for Example 3 except replacing $CH_3I$ with ethyl 2-bromopropionate.

$^1$HNMR (300 MHz, $d_6$-DMSO): δ 1.19~1.24 (t, 6H), 1.53 (d, 6H), 2.22 (s, 3H), 2.45 (s, 3H), 3.85 (s, 3H), 4.14~4.20 (m, 4H), 5.17~5.26 (m, 2H), 6.86 (s, 1H), 7.13 (s, 1H), 10.24 (s, 1H).

Example 16

4-Formyl-3-hydroxy-8-methoxy-1,9-dimethyl-11-oxo-11H-dibenzo[b,e][1,4]dioxepine-6-carboxy-(3-ethoxycarboxyl)-ethyl propionate (Compound No:B4)

This compound was prepared by means of a procedure similar to that used for Example 2 except replacing $CH_3I$ with ethyl 4-bromobutyrate.

$^1$HNMR (300 MHz, $d_6$-DMSO): δ 1.11 (t, 3H), 1.51 (d, 3H), 1.96 (t, 3H), 2.20 (s, 3H), 2.41 (t, 2H), 2.45 (s, 3H), 3.84 (s, 3H), 4.00 (t, 2H), 4.29 (t, 2H), 6.89 (s, 1H), 7.10 (s, 1H), 10.33 (s, 1H).

Example 17

3-(3-Ethoxycarboxyl-propoxy)-4-formyl-8-methoxy-1,9-dimethyl-11-oxo-11H-dibenzo[b,e][1,4]dioxepine-6-carboxy-(3-ethoxycarboxyl)-ethyl propionate (Compound No:B5)

This compound was prepared by means of a procedure similar to that used for Example 3 except replacing $CH_3I$ with ethyl 4-bromobutyrate.

$^1$HNMR (300 MHz, $d_6$-DMSO): δ 1.12 (t, 3H), 1.17 (t, 3H), 1.96~2.06 (m, 4H), 2.19 (s, 3H), 2.38~2.44 (m, 7H), 3.53 (t, 2H), 3.83 (s, 3H), 3.96~4.03 (q, 2H), 4.03~4.09 (q, 2H), 4.28 (t, 2H), 6.85 (s, 1H), 7.09 (s, 1H), 10.32 (s, 1H).

Example 18

3-Hydroxy-4-[(2-hydroxy-ethylamino)-methyl]-8-methoxy-1,9-dimethyl-11-oxo-11H-dibenzo[b,e][1,4]dioxepine-6-carboxylic acid (Compound No:B6)

To a stirring solution of psoromic acid (1 mmol) in ethanol (25 mL) was added 2-amino-ethanol (1 mmol). The reaction was stirred for half an hour. The reaction was added with sodium borohydride (4 mmol) under ice bath, and stirred for additional 15 min under ice bath and then allowed to react overnight at room temperature. Water (3 mL) was added, the solution was acidified to a pH of 6 with dilute HCl. All of the solvent was removed by rotary evaporation. The residue was redissolved in ethanol and dried over anhydrous magnesium sulfate, filtered, and evaporated by a rotary evaporator to give a white solid product.

$^1$HNMR (300 MHz, $d_6$-DMSO): δ 2.06 (s, 3H), 2.21 (s, 3H), 2.81 (t, 2H), 3.56 (t, 2H), 3.70 (s, 3H), 4.12 (s, 2H), 4.44 (s, 2H), 6.40 (s, 1H), 6.58 (s, 1H).

Example 19

4-(Benzylamino-methyl)-3-hydroxy-8-methoxy-1,9-dimethyl-11-oxo-11H-dibenzo[b,e][1,4]dioxepine-6-carboxylic acid (Compound No:B7)

This compound was prepared by means of a procedure similar to that used for Example 18 except replacing ethanolamine with benzylamine.

$^1$HNMR (300 MHz, $CD_3OD$): δ 2.14 (s, 3H), 2.37 (s, 3H), 3.83 (s, 3H), 4.32 (s, 2H), 4.44 (s, 2H), 6.55 (s, 1H), 6.89 (s, 1H), 7.41~7.43 (m, 3H), 7.57~7.61 (m, 2H).

Example 20

4-[(2-Diethylamino-ethylamino)-methyl]-3-hydroxy-8-methoxy-1,9-dimethyl-11-oxo-11H-dibenzo[b,e][1,4]dioxepine-6-carboxylic acid (Compound No:B8)

This compound was prepared by means of a procedure similar to that used for Example 18 except replacing ethanolamine with N,N-diethyl ethylenediamine.

$^1$HNMR (300 MHz, $d_6$-DMSO): δ 1.02 (t, 6H), 2.07 (s, 3H), 2.23 (s, 3H), 2.67 (q, 4H), 2.83 (t, 2H), 3.05 (t, 2H), 3.73 (s, 3H), 4.10 (s, 2H), 6.27 (s, 1H), 6.61 (s, 1H).

EI: 458, 441, 344, 272, 116, 107, 86;

Example 21

3-Hydroxy-8-methoxy-1,9-dimethyl-11-oxo-4-phenylaminomethyl-11H-dibenzo[b,e][1,4]dioxepine-6-carboxylic acid (Compound No:B9)

This compound was prepared by means of a procedure similar to that used for Example 18 except replacing ethanolamine with aniline.

¹HNMR (300 MHz, d₆-DMSO): δ 2.06 (s, 3H), 2.13 (s, 3H), 3.74 (s, 3H), 4.41 (s, 2H), 6.39~6.43 (m, 2H), 6.57 (d, 2H), 6.77 (s, 1H), 6.96 (t, 2H).

Example 22

3-Hydroxy-8-methoxy-4-[(2-methoxy-ethylamino)-methyl]-1,9-dimethyl-11-oxo-11H-dibenzo[b,e][1,4]dioxepine-6-carboxylic acid (Compound No:C0)

This compound was prepared by means of a procedure similar to that used for Example 18 except replacing ethanolamine with 2-methoxy-ethylamine.
¹HNMR (300 MHz, d₆-DMSO): δ 2.10 (s, 3H), 2.35 (s, 3H), 3.20 (t, 2H), 3.30 (s, 3H), 3.68 (t, 2H), 3.76 (s, 3H), 4.18 (s, 2H), 6.71 (s, 1H), 6.83 (s, 1H).

Example 23

3-Hydroxy-8-methoxy-1,9-dimethyl-11-oxo-4-[(2-pyrrol-1-yl-ethylamino)-methyl]-11H-dibenzo[b,e][1,4]dioxepine-6-carboxylic acid (Compound No:C1)

This compound was prepared by means of a procedure similar to that used for Example 18 except replacing ethanolamine with 2-pyrrol-1-yl-ethylamine.
¹HNMR (300 MHz, d₆-DMSO): δ 1.96 (m, 6H), 2.17 (s, 3H), 2.39 (s, 3H), 3.22 (t, 2H), 3.40~3.68 (m, 6H), 3.61 (s, 3H), 4.37 (s, 2H), 6.87 (s, 1H), 7.10 (s, 1H).

Example 24

3-Hydroxy-8-methoxy-1,9-dimethyl-11-oxo-4-(prop-2-ynylaminomethyl)-11H-dibenzo[b,e][1,4]dioxepine-6-carboxylic acid (Compound No:C2)

This compound was prepared by means of a procedure similar to that used for Example 18 except replacing ethanolamine with propynyl-2-amine.
¹HNMR (300 MHz, d₆-DMSO): δ 2.10 (s, 3H), 2.34 (s, 3H), 3.76 (s, 3H), 3.85 (d, 2H), 4.16 (s, 2H), 6.71 (s, 1H), 6.85 (s, 1H).

Example 25

3-Hydroxy-8-methoxy-1,9-dimethyl-11-oxo-4-[(4-sulfamoyl-phenyl)-aminomethyl]-11H-dibenzo[b,e][1,4]dioxepine-6-carboxylic acid (Compound No:C3)

This compound was prepared by means of a procedure similar to that used for Example 18 except replacing ethanolamine with sulphanilic amide.
¹HNMR (300 MHz, d₆-DMSO): δ 2.05 (s, 3H), 2.17 (s, 3H), 3.73 (s, 3H), 4.46 (s, 2H), 6.47 (s, 1H), 6.63 (d, 2H), 6.78 (s, 1H), 7.40 (d, 2H).

Example 26

4-[(3,3-Dimethylamino-propylamino)-aminomethyl]-3-hydroxy-8-methoxy-1,9-dimethyl-11-oxo-11H-dibenzo[b,e][1,4]dioxepine-6-carboxylic acid (Compound No:C4)

This compound was prepared by means of a procedure similar to that used for Example 18 except replacing ethanolamine with N,N-dimethyl propylenediamine.
¹HNMR (300 MHz, d₆-DMSO): δ 1.85 (m, 2H), 2.10 (s, 3H), 2.34 (s, 3H), 2.65 (s, 6H), 2.78~2.82 (t, 2H), 3.01~3.09 (t, 2H), 3.75 (s, 3H), 4.17 (s, 2H), 6.71 (s, 1H), 6.77 (s, 1H).

Example 27

4-Cyclopropylaminomethyl-3-hydroxy-8-methoxy-1,9-dimethyl-11-oxo-11H-dibenzo[b,e][1,4]dioxepine-6-carboxylic acid (Compound No:C5)

This compound was prepared by means of a procedure similar to that used for Example 18 except replacing ethanolamine with aminocyclopropane.
¹HNMR (300 MHz, d₆-DMSO): δ 0.56~0.85 (m, 7H), 2.17 (s, 3H), 2.37 (s, 3H), 2.65 (s, 6H), 3.82 (s, 3H), 4.40 (s, 2H), 6.82 (s, 1H), 7.07 (s, 1H).

Example 28

3-Hydroxy-8-methoxy-1,9-dimethyl-11-oxo-4-[(1-phenyl-ethylamino)-methyl]-11H-dibenzo[b,e][1,4]dioxepine-6-carboxylic acid (Compound No:C6)

This compound was prepared by means of a procedure similar to that used for Example 18 except replacing ethanolamine with 2-methyl phenylethylamine.

Example 29

3-Hydroxy-8-methoxy-1,9-dimethyl-4-[(2-morpholin-4-yl-ethylamino)-methyl]-11-oxo-11H-dibenzo[b,e][1,4]dioxepine-6-carboxylic acid (Compound No:C7)

This compound was prepared by means of a procedure similar to that used for Example 18 except replacing ethanolamine with 2-morpholin-4-yl-ethylamine.
¹HNMR (300 MHz, CD₃OD): δ2.19 (s, 3H), 2.42 (s, 3H), 2.50~2.54 (m, 4H), 2.79~2.84 (t, 2H), 3.31~3.35 (t, 2H), 3.69~3.75 (m, 4H), 3.84 (s, 3H), 4.47 (s, 2H), 6.70 (s, 1H), 6.95 (s, 1H).

Example 30

3-Hydroxy-8-methoxy-1,9-dimethyl-4-methylaminomethyl-11-oxo-11H-dibenzo[b,e][1,4]dioxepine-6-carboxylic acid (Compound No:C8)

This compound was prepared by means of a procedure similar to that used for Example 18 except replacing ethanolamine with methylamine.
¹HNMR (300 MHz, d₆-DMSO): δ 2.24 (s, 3H), 2.45 (s, 3H), 2.82 (s, 3H), 3.87 (s, 3H), 4.46 (s, 2H), 6.74 (s, 1H), 7.21 (s, 1H).

Example 31

3-Hydroxy-4-(isopropylamino-methyl)-8-methoxy-1,9-dimethyl-11-oxo-11H-dibenzo[b,e][1,4]dioxepine-6-carboxylic acid (Compound No:C9)

This compound was prepared by means of a procedure similar to that used for Example 18 except replacing ethanolamine with isopropyl amine.
¹HNMR (300 MHz, d₆-DMSO): δ 1.31 (d, 6H), 2.05 (s, 3H), 2.17 (s, 3H), 2.36 (s, 1H), 3.71 (s, 3H), 4.02 (s, 2H), 5.96 (s, 1H), 6.58 (s, 1H).

Example 32

4-Ethylaminomethyl-3-hydroxy-8-methoxy-1,9-dimethyl-11-oxo-11H-dibenzo[b,e][1,4]dioxepine-6-carboxylic acid (Compound No:D0)

This compound was prepared by means of a procedure similar to that used for Example 18 except replacing ethanolamine with ethylamine.

$^1$HNMR (300 MHz, $CD_3OD$): δ 1.36 (t, 3H), 2.24 (s, 3H), 2.44 (s, 3H), 3.23 (q, 2H), 3.87 (s, 3H), 4.48 (s, 2H), 6.75 (s, 1H), 7.22 (s, 1H).

Example 33

3-Hydroxy-8-methoxy-1,9-dimethyl-11-oxo-4-(piperazin-1-ylmethyl)-11H-dibenzo[b,e][1,4]dioxepine-6-carboxylic acid (Compound No:D1)

This compound was prepared by means of a procedure similar to that used for Example 18 except replacing ethanolamine with piperazine.

$^1$HNMR (300 MHz, $CD_3OD$): δ 2.12 (s, 3H), 2.30 (s, 3H), 2.67 (m, 4H), 3.05 (m, 4H), 3.78 (s, 3H), 3.89 (s, 2H), 4.48 (s, 2H), 6.69 (s, 1H), 6.91 (s, 1H).

Example 34

4-Diethylaminomethyl-3-hydroxy-8-methoxy-1,9-dimethyl-11-oxo-11H-dibenzo[b,e][1,4]dioxepine-6-carboxylic acid (Compound No:D2)

This compound was prepared by means of a procedure similar to that used for Example 18 except replacing ethanolamine with diethylamine.

$^1$HNMR (300 MHz, $CD_3OD$): δ 1.34~1.39 (t, 6H), 2.18 (s, 3H), 2.39 (s, 3H), 3.21 (q, 4H), 3.83 (s, 3H), 4.58 (s, 2H), 6.56 (s, 1H), 6.87 (s, 1H).

Example 35

4-(tert-Butylamino-methyl)-3-hydroxy-8-methoxy-1,9-dimethyl-11-oxo-11H-dibenzo[b,e][1,4]dioxepine-6-carboxylic acid (Compound No:D3)

This compound was prepared by means of a procedure similar to that used for Example 18 except replacing ethanolamine with tert-butylamine.

$^1$HNMR (300 MHz, $d_6$-DMSO): δ 1.52 (s, 9H), 2.19 (s, 3H), 2.41 (s, 3H), 3.83 (s, 3H), 4.31 (s, 2H), 6.66 (s, 1H), 6.86 (s, 1H).

Example 36

4-(4-Benzyl-piperazin-1-ylmethyl)-3-hydroxy-8-methoxy-1,9-dimethyl-11-oxo-11H-dibenzo[b,e][1,4]dioxepine-6-carboxylic acid (Compound No:D4)

This compound was prepared by means of a procedure similar to that used for Example 18 except replacing ethanolamine with Benzyl piperazine.

$^1$HNMR (300 MHz, $d_6$-DMSO): δ 2.07 (s, 3H), 2.28 (s, 3H), 2.52 (t, 4H), 3.02 (t, 4H), 3.47 (s, 2H), 3.73 (s, 3H), 4.16 (s, 2H), 6.52 (s, 1H), 6.78 (s, 1H), 7.21~7.31 (m, 5H).

Example 37

4-[(Cyclohexyl-amino)-methyl]-3-hydroxy-8-methoxy-1,9-dimethyl-11-oxo-11H-dibenzo[b,e][1,4]dioxepine-6-carboxylic acid (Compound No:D5)

This compound was prepared by means of a procedure similar to that used for Example 18 except replacing ethanolamine with cyclohexylmethylamine.

$^1$HNMR (300 MHz, $CD_3OD$): δ 1.04~1.32 (m, 4H), 1.36~1.87 (m, 7H), 2.25 (s, 3H), 2.45 (s, 3H), 3.00 (d, 2H), 3.87 (s, 3H), 4.48 (s, 2H), 6.76 (s, 1H), 7.27 (s, 1H).

Example 38

4-[(3,4-Dimethoxy-phenylamino)-methyl]-3-hydroxy-8-methoxy-1,9-dimethyl-11-oxo-11H-dibenzo[b,e][1,4]dioxepine-6-carboxylic acid (Compound No:D6)

This compound was prepared by means of a procedure similar to that used for Example 18 except replacing ethanolamine with 3,4-dimethoxy-phenylamine.

$^1$HNMR (300 MHz, $d_6$-DMSO): δ 2.16 (s, 3H), 2.31 (s, 3H), 3.68 (s, 3H), 3.78 (s, 3H), 3.82 (s, 3H), 4.57 (s, 2H), 6.32~6.38 (d, d, 1H), 6.52 (s, 1H) 6.61 (d, 1H), 6.69~6.72 (m, 1H), 6.92 (s, 1H).

Example 39

4-[(2-Carboxy-4,5-dimethoxy-phenylamino)-methyl]-3-hydroxy-8-methoxy-1,9-dimethyl-11-oxo-11H-dibenzo[b,e][1,4]dioxepine-6-carboxylic acid (Compound No:D7)

This compound was prepared by means of a procedure similar to that used for Example 18 except replacing ethanolamine with 2-amino-4,5-dimethoxy-benzoic acid.

$^1$HNMR (300 MHz, $d_6$-DMSO): δ 2.23 (s, 3H), 2.41 (s, 3H), 3.86 (s, 3H), 3.88 (s, 3H), 3.96 (s, 3H), 5.05 (s, 2H), 6.67 (s, 1H), 7.22 (d, 1H), 7.30 (s, 1H), 7.58 (s, 1H).

Example 40

4-[(4-Acetylamino-phenylamino)-methyl]-3-hydroxy-8-methoxy-1,9-dimethyl-11-oxo-11H-dibenzo[b,e][1,4]dioxepine-6-carboxylic acid (Compound No:D8)

This compound was prepared by means of a procedure similar to that used for Example 18 except replacing ethanolamine with p-acetylamino-phenylamine.

$^1$HNMR (300 MHz, $d_6$-DMSO): δ 2.14 (s, 3H), 2.26 (s, 3H), 2.46 (s, 3H), 3.87 (s, 3H), 4.89 (s, 2H), 6.74 (s, 1H), 7.26 (s, 1H), 7.50 (d, 2H), 7.74 (d, 2H).

Example 41

4-[(3-Cyano-phenylamino)-methyl]-3-hydroxy-8-methoxy-1,9-dimethyl-11-oxo-11H-dibenzo[b,e][1,4]dioxepine-6-carboxylic acid (Compound No:D9)

This compound was prepared by means of a procedure similar to that used for Example 18 except replacing ethanolamine with 3-cyano-phenylamine.

¹HNMR (300 MHz, d₆-DMSO): δ 2.19 (s, 3H), 2.34 (s, 3H), 3.85 (s, 3H), 4.54 (s, 2H), 6.59 (s, 1H), 6.84 (d, 1H), 6.99~7.02 (m, 2H), 7.17 (m, 1H).

Example 42

4-[(5-Carboxy-2-methoxy-phenylamino)-methyl]-3-hydroxy-8-methoxy-1,9-dimethyl-11-oxo-11H-dibenzo[b,e][1,4]dioxepine-6-carboxylic acid (Compound No:E0)

This compound was prepared by means of a procedure similar to that used for Example 18 except replacing ethanolamine with 3-amino-4-methoxy-benzoic acid.
¹HNMR (300 MHz, d₆-DMSO): δ 2.24 (s, 3H), 2.42 (s, 3H), 3.86 (s, 3H), 4.01 (s, 3H), 4.93 (s, 2H), 6.68 (s, 1H), 7.19 (s, 1H), 7.24 (d, 1H), 7.97 (s, 1H), 8.04 (d, 1H).

Example 43

4-Hydrazonomethyl-3-hydroxy-8-methoxy-1,9-dimethyl-11-oxo-11H-dibenzo[b,e][1,4]dioxepine-6-carboxylic acid (Compound No:E1)

To a stirring solution of psoromic acid (1 mmol) in ethanol (25 mL) was added hydrazine hydrate (1 mmol). The reaction was stirred for half an hour and monitored by TLC. Upon completion, all of the solvent was removed by rotary evaporation. The residue was redissolved in ethanol and dried over anhydrous magnesium sulfate, filtered, and evaporated by a rotary evaporator to yield a white solid product.
¹HNMR (300 MHz, d₆-DMSO): δ 2.08 (s, 3H), 2.34 (s, 3H), 3.74 (s, 3H), 6.54 (s, 1H), 6.76 (s, 1H), 8.82 (s, 1H).

Example 44

3-Hydroxy-8-methoxy-1,9-dimethyl-11-oxo-4-(phenyl-hydrazonomethyl)-11H-dibenzo[b,e][1,4]dioxepine-6-carboxylic acid (Compound No:E2)

This compound was prepared by means of a procedure similar to that used for Example 43 except replacing hydrazine hydrate with phenyl hydrazine.
¹HNMR (300 MHz, d₆-DMSO): δ 2.19 (s, 3H), 2.40 (s, 3H), 3.82 (s, 3H), 6.80 (s, 1H), 6.85 (t, 1H), 6.93 (d, 2H), 7.05 (s, 1H), 7.30 (t, 2H), 8.69 (s, 1H).

Example 45

3-Hydroxy-4-[(4-methanesulfonyl-phenyl)-hydrazonomethyl]-8-methoxy-1,9-dimethyl-11-oxo-11H-dibenzo[b,e][1,4]dioxepine-6-carboxylic acid (Compound No:E3)

This compound was prepared by means of a procedure similar to that used for Example 43 except replacing hydrazine hydrate with p-methanesulfonyl phenyl hydrazine.
¹HNMR (300 MHz, d₆-DMSO): δ 2.19 (s, 3H), 2.42 (s, 3H), 3.11 (s, 3H), 3.82 (s, 3H), 6.84 (s, 1H), 7.10 (m, 3H), 7.80 (d, 2H), 8.76 (s, 1H).

Example 46

4-[(3-Fluoro-benzoyl)-hydrazonomethyl]-3-hydroxy-8-methoxy-1,9-dimethyl-11-oxo-11H-dibenzo[b,e][1,4]dioxepine-6-carboxylic acid (Compound No:E4)

This compound was prepared by means of a procedure similar to that used for Example 43 except replacing hydrazine hydrate with 3-fluoro benzoyl hydrazine.
¹HNMR (300 MHz, d₆-DMSO): δ 2.20 (s, 3H), 2.42 (s, 3H), 3.11 (s, 3H), 3.84 (s, 3H), 6.84 (s, 1H), 7.09 (m, 3H), 7.36~7.86 (m, 5H), 9.14 (s, 1H).

Example 47

4-[(Furan-2-carbonyl)-hydrazonomethyl]-3-hydroxy-8-methoxy-1,9-dimethyl-11-oxo-11H-dibenzo[b,e][1,4]dioxepine-6-carboxylic acid (Compound No:E5)

This compound was prepared by means of a procedure similar to that used for Example 43 except replacing hydrazine hydrate with 2-furan formyl hydrazine.
¹HNMR (300 MHz, d₆-DMSO): δ 2.19 (s, 3H), 2.42 (s, 3H), 3.82 (s, 3H), 6.73 (s, 1H), 6.81 (s, 1H), 7.06 (s, 1H), 7.38 (t, 1H), 7.97 (t, 1H), 9.12 (s, 1H).

Example 48

4-[(4-Chloro-benzoyl)-hydrazonomethyl]-3-hydroxy-8-methoxy-1,9-dimethyl-11-oxo-11H-dibenzo[b,e][1,4]dioxepine-6-carboxylic acid (Compound No:E6)

This compound was prepared by means of a procedure similar to that used for Example 43 except replacing hydrazine hydrate with p-chloro benzoyl hydrazine.
¹HNMR (300 MHz, d₆-DMSO): δ 2.20 (s, 3H), 2.42 (s, 3H), 3.83 (s, 3H), 6.80 (s, 1H), 7.07 (s, 1H), 7.55 (d, 2H), 7.98 (d, 2H), 9.12 (s, 1H).

Example 49

3-Hydroxy-8-methoxy-1,9-dimethyl-11-oxo-4-[(thiophene-2-carbonyl)-hydrazonomethyl]-11H-dibenzo[b,e][1,4]dioxepine-6-carboxylic acid (Compound No:E7)

This compound was prepared by means of a procedure similar to that used for Example 43 except replacing hydrazine hydrate with 2-thiophene formyl hydrazine.
¹HNMR (300 MHz, d₆-DMSO): δ 2.19 (s, 3H), 2.42 (s, 3H), 3.82 (s, 3H), 6.83 (s, 1H), 7.07 (s, 1H), 7.27 (t, 1H), 7.92 (d, d, 1H), 8.00 (d, d, 1H), 9.10 (s, 1H).

Example 50

3-Hydroxy-8-methoxy-1,9-dimethyl-11-oxo-4-(isonicotinyl-hydrazonomethyl)-11H-dibenzo[b,e][1,4]dioxepine-6-carboxylic acid (Compound No:E8)

This compound was prepared by means of a procedure similar to that used for Example 43 except replacing hydrazine hydrate with isoniazid.
¹HNMR (300 MHz, d₆-DMSO): δ 2.19 (s, 3H), 2.42 (s, 3H), 3.82 (s, 3H), 6.84 (s, 1H), 7.07 (s, 1H), 7.90 (d, 2H), 8.84 (d, 2H), 9.16 (s, 1H).

Example 51

3-Hydroxy-4-hydroxymethyl-8-methoxy-1,9-dimethyl-11-oxo-11H-dibenzo[b,e][1,4]dioxepine-6-carboxylic acid (Compound No:E9)

To a stirring solution of psoromic acid (1 mmol) in ethanol (25 mL) was added sodium borohydride (4 mmol). The reaction was stirred overnight at room temperature. Water (3 mL) was added to the reaction. The solution was acidified to a pH of 6 with dilute HCl. All of the solvent was removed by rotatory evaporation. The residue was redissolved in ethanol and dried over magnesium sulfate, filtered, and evaporated by a rotatory evaporator to give a white solid product.

$^1$HNMR (300 MHz, $d_6$-DMSO): δ 2.09 (s, 3H), 2.40 (s, 3H), 3.28 (s, 2H), 3.82 (s, 3H), 6.59 (s, 1H), 6.97 (s, 1H).

Example 52

2-Bromo-4-formyl-3-hydroxy-8-methoxy-1,9-dimethyl-11-oxo-11H-dibenzo[b,e][1,4]dioxepine-6-carboxylic acid (Compound No:F0)

To a solution of psoromic acid (1 mmol) in glacial acetic acid (5 ml) was dropwise added a solution of bromine (3 mmol, 0.15 ml) in glacial acetic acid (3 ml). After stirring at room temperature for several hours, the redbrown reaction mixture was poured into water (50 ml), extracted with ethyl acetate (100 ml), dried with $MgSO_4$, filtered, and evaporated by a rotatory evaporator to give a redbrown solid.

$^1$HNMR (300 MHz, $d_6$-DMSO): δ 1.90 (s, 3H), 2.20 (s, 3H), 3.83 (s, 3H), 7.12 (s, 1H).

Example 53

3-Acetyl-4-formyl-8-methoxy-1,9-dimethyl-11-oxo-11H-dibenzo[b,e][1,4]dioxepine-6-carboxylic acid Psoromic acid (1 mmol) was dissolved in pyridine (2 ml) and glacial acetic acid (1 ml). The reaction was stirred for 14 hours at room temperature. Most of the solvent was removed by rotatory evaporation. The residue was taken up in methylene chloride, washed with water and saturated brine, dried with anhydrous $MgSO_4$, evaporated by a rotatory evaporator and purified by column chromatography.

Example 54

3-Hydroxy-8-methoxy-1,9-dimethyl-11-oxo-4-[(pyrimidin-2-ylaminomethyl)-formyl]-11H-dibenzo[b,e][1,4]dioxepine-6-carboxylic acid (Compound No:AA4)

This compound was prepared by means of a procedure similar to that used for Example 18 except replacing ethanolamine with 2-amino pyridine.

$^1$HNMR (300 MHz, $d_6$-DMSO): δ 2.12 (s, 3H), 2.32 (s, 3H), 3.77 (s, 3H), 4.62 (s, 2H), 6.47 (m, 2H), 6.65 (s, 1H), 6.88 (s, 1H), 7.37 (t, d, 1H), 7.88 (d, 1H).

Example 55

3-Hydroxy-8-methoxy-1,9-dimethyl-11-oxo-4-[(4-sulfamoyl-phenylamino)-methyl]-11H-dibenzo[b,e][1,4]dioxepine-6-carboxylic acid propyl ester (Compound No:AA5)

This compound was prepared from the compound from Example 8 by means of a procedure similar to that used for Example 18 except replacing ethanolamine with sulphanilic amide.

$^1$HNMR (300 MHz, $d_6$-DMSO): δ 0.84 (t, 3H, J=7.5 Hz), 1.59 (q, 2H, J=6.9 Hz), 2.16 (s, 3H), 2.33 (s, 3H), 3.82 (s, 3H), 3.98 (t, 2H), 4.52 (s, 2H), 6.60 (d, 1H, J=8.7 Hz), 6.72 (m, 2H), 7.02 (s, 1H), 7.48 (m, 2H). ESI-MS: m/z 579 [M+Na]$^+$.

Example 56

3-Hydroxy-8-methoxy-1,9-dimethyl-4-[(2-morpholin-4-yl-ethylamino)-methyl]-11-oxo-11H-dibenzo[b,e][1,4]dioxepine-6-carboxylic acid propyl ester (Compound No:AA6)

This compound was prepared from the compound from Example 8 by means of a procedure similar to that used for Example 18 except replacing ethanolamine with 2-morpholin-4-yl-ethylamine.

$^1$HNMR (300 MHz, $d_6$-DMSO): δ 0.97 (t, 3H, J=7.5 Hz), 1.76 (q, 2H, J=6.9 Hz), 2.16 (s, 3H), 2.25 (s, 3H), 2.37 (m, 4H), 2.46 (m, 2H), 2.77 (m, 2H), 3.69 (m, 4H), 3.81 (s, 3H), 4.06 (s, 2H), 4.28 (t, 2H, J=6.6 Hz), 6.25 (s, 1H), 6.92 (s, 1H). ESI-MS: m/z 537[M+Na]$^+$.

Example 57

4-[(4-Fluoro-phenylamino)-methyl]-3-hydroxy-8-methoxy-1,9-dimethyl-11-oxo-11H-dibenzo[b,e][1,4]dioxepine-6-carboxylic acid (Compound No:AA7)

This compound was prepared by means of a procedure similar to that used for Example 18 except replacing ethanolamine with p-fluoro-phenylamine.

$^1$HNMR (300 MHz, $d_6$-DMSO): δ 2.07 (s, 3H), 2.12 (s, 3H), 3.75 (s, 3H), 4.41 (s, 2H), 6.35 (s, 1H), 6.60 (m, 2H), 6.82 (m, 3H). ESI-MS: m/z 498[M+Na]$^+$.

Example 58

4-[(4-Amino-phenylamino)-methyl]-3-hydroxy-8-methoxy-1,9-dimethyl-11-oxo-11H-dibenzo[b,e][1,4]dioxepine-6-carboxylic acid (Compound No:AA8)

This compound was prepared by means of a procedure similar to that used for Example 18 except replacing ethanolamine with p-phenylene diamine.

$^1$HNMR (300 MHz, $d_6$-DMSO): δ 2.07 (s, 3H), 2.10 (s, 3H), 3.75 (s, 3H), 4.38 (s, 2H), 6.34 (d, 2H), 6.37 (s, 1H), 6.46 (d, 2H), 6.76 (s, 1H).

Example 59

3-Hydroxy-8-methoxy-1,9-dimethyl-11-oxo-4-(pyrimidin-2-ylaminomethyl)-11H-dibenzo[b,e][1,4]dioxepine-6-carboxylic acid (Compound No:AA9)

This compound was prepared by means of a procedure similar to that used for Example 18 except replacing ethanolamine with 2-aminopyrimidine.

$^1$HNMR (300 MHz, $d_6$-DMSO): δ 2.14 (s, 3H), 2.33 (s, 3H), 3.80 (s, 3H), 4.65 (s, 2H), 6.70 (s, 1H), 6.94 (t, 1H, J=5.1 Hz), 6.99 (s, 1H), 8.57 (d, 2H, J=5.1 Hz).

Example 60

3-Hydroxy-8-methoxy-1,9-dimethyl-11-oxo-4-[(2-piperidin-1-yl-ethylamino)-methyl]-11H-dibenzo[b,e][1,4]dioxepine-6-carboxylic acid (Compound No:AB0)

This compound was prepared by means of a procedure similar to that used for Example 18 except replacing ethanolamine with 2-piperidin-1-yl-ethylamine.

ESI-MS: m/z 471 (M-H$^-$).

Example 61

4-Formyl-3-hydroxy-8-methoxy-1,9-dimethyl-11-oxo-11H-dibenzo[b,e][1,4]dioxepine-6-carboxylic acid dimethylamide (Compound No:AB3)

Psoromic acid (35 mg, 1 mmol), EDCI (20 mg, 1.5 mmol) and HOBt (23 mg, 1.5 mmol) were added into DMF (5 ml) under ice bath. The solution was stirred for half an hour, and then to the reaction mixture was added dropwise a solution of dimethyl-amine hydrochloride (8.7 mg, 1 mmol) and triethylamine (0.014 ml, 1 mmol) in anhydrous DMF (3 ml). The reaction was monitored by TLC. Upon completion, the reaction mixture was poured into 60 mL of water and extracted with ethyl acetate. The organic layer was subsequently washed with saturated NaHCO$_3$, saturated brine, dried over anhydrous MgSO$_4$, filtered, evaporated by a rotatory evaporator, and purified by column chromatography to give a white solid product.

$^1$HNMR (300 MHz, CDCl$_3$): δ 2.20 (s, 3H), 2.49 (s, 3H), 2.88 (s, 3H), 3.13 (s, 3H), 3.80 (s, 3H), 6.48 (s, 1H), 6.63 (s, 1H), 10.07 (s, 1H), 12.12 (s, 1H). ESI-MS: m/z 386 (MH$^+$).

Example 62

3-Hydroxy-8-methoxy-1,9-dimethyl-11-oxo-4-pheyliminomethyl-11H-dibenzo[b,e][1,4]dioxepine-6-carboxylic acid phenylamide (Compound No:AB1)

This compound was prepared by means of a procedure similar to that used for Example 61 except replacing dimethyl-amine hydrochloride with aniline.

$^1$HNMR (300 MHz, d$_6$-DMSO): δ 2.27 (s, 3H), 2.47 (s, 3H), 3.90 (s, 3H), 6.64 (s, 1H), 6.84 (s, 1H), 7.17 (m, 7H), 7.48 (m, 2H), 7.83 (m, 1H), 9.20 (s, 1H). ESI-MS: m/z 507 (M-H$^-$).

Example 63

4-Formyl-3-hydroxy-8-methoxy-1,9-dimethyl-11-oxo-11H-dibenzo[b,e][1,4]dioxepine-6-carboxylic acid diethylamide (Compound No:AB5)

This compound was prepared by means of a procedure similar to that used for Example 61 except replacing dimethyl-amine hydrochloride with diethyl-amine hydrochloride.

$^1$HNMR (300 MHz, CDCl$_3$): δ 1.10 (t, 3H, J=7.2 Hz), 1.22 (t, 3H, J=7.2 Hz), 2.22 (s, 3H), 2.46 (s, 3H), 3.23 (q, 2H, J=7.2 Hz), 3.48 (m, 1H), 3.79 (m, 4H), 6.45 (s, 1H), 6.64 (s, 1H), 10.14 (s, 1H), 12.17 (s, 1H). ESI-MS: m/z 436[M+Na]$^+$.

Example 64

4-Formyl-3-hydroxy-8-methoxy-1,9-dimethyl-11-oxo-11H-dibenzo[b,e][1,4]dioxepine-6-carboxylic acid ethylamide (Compound No:AB4)

This compound was prepared by means of a procedure similar to that used for Example 61 except replacing dimethyl-amine hydrochloride with ethyl-amine hydrochloride.

$^1$HNMR (300 MHz, CDCl$_3$): δ 1.26 (t, 3H, J=5.7 Hz), 2.21 (s, 3H), 2.48 (s, 3H), 3.50 (q, 2H, J=5.7 Hz), 3.80 (s, 3H), 6.48 (s, 1H), 6.67 (s, 1H), 10.32 (s, 1H), 12.22 (s, 1H). ESI-MS: m/z 408[M+Na]$^+$.

Example 65

4-Formyl-3-hydroxy-8-methoxy-1,9-dimethyl-11-oxo-11H-dibenzo[b,e][1,4]dioxepine-6-carboxylic acid methylamide (Compound No:AB2)

This compound was prepared by means of a procedure similar to that used for Example 61 except replacing dimethyl-amine hydrochloride with methyl-amine hydrochloride.

$^1$HNMR (300 MHz, CDCl$_3$): δ 2.24 (s, 3H), 2.48 (s, 3H), 3.03 (d, 2H, J=4.8 Hz), 3.80 (s, 3H), 6.66 (s, 1H), 6.69 (s, 1H), 10.29 (s, 1H), 12.21 (s, 1H). ESI-MS: m/z 372 (MH$^+$).

Example 66

4-(Benzylimino-methyl)-3-hydroxy-8-methoxy-1,9-dimethyl-11-oxo-11H-dibenzo[b,e][1,4]dioxepine-6-carboxylic acid benzylamide (Compound No:AB6)

This compound was prepared by means of a procedure similar to that used for Example 61 except replacing dimethyl-amine hydrochloride with benzyl amine.

$^1$HNMR (300 MHz, d$_6$-DMSO): δ 2.20 (s, 3H), 2.47 (s, 3H), 3.79 (s, 3H), 4.47 (s, 2H), 4.61 (d, 2H, J=5.7 Hz), 6.48 (s, 1H), 6.69 (m, 2H), 7.29 (m, 9H), 8.93 (s, 1H). ESI-MS: m/z 538 (MH$^+$).

Example 67

3-Hydroxy-8-methoxy-1,9-dimethyl-11-oxo-4-[(4-sulfamoylphenyl)-iminomethyl]-11H-dibenzo[b,e][1,4]dioxepine-6-[carboxy-(4-sulfamoyl)phenylamide] (Compound No:AB9)

This compound was prepared by means of a procedure similar to that used for Example 61 except replacing dimethyl-amine hydrochloride with sulfanilic amide.

Example 68

4-Formyl-3-hydroxy-8-methoxy-1,9-dimethyl-11-oxo-11H-dibenzo[b,e][1,4]dioxepine-6-carboxylic acid (2-morpholin-4-yl-ethyl)-amide (Compound No:AB8)

This compound was prepared by means of a procedure similar to that used for Example 61 except replacing dimethyl-amine hydrochloride with 2-morpholin-4-yl-ethylamine.

$^1$HNMR (300 MHz, CDCl$_3$): δ 2.15 (s, 3H), 2.47 (s, 3H), 2.96 (m, 2H), 3.04 (m, 2H), 3.72 (s, 3H), 3.82 (m, 8H), 6.64 (s, 1H), 8.00 (s, 1H), 10.31 (s, 1H). ESI-MS: m/z 471 (MH$^+$).

Example 69

4-Formyl-3-Hydroxy-8-methoxy-1,9-dimethyl-11-oxo-11H-dibenzo[b,e][1,4]dioxepine-6-(carboxy-methyl-piperazineamide) (Compound No:AB7)

This compound was prepared by means of a procedure similar to that used for Example 61 except replacing dimethyl-amine hydrochloride with methyl piperazine.

$^1$HNMR (300 MHz, d$_6$-DMSO): δ 2.02 (s, 3H), 2.30 (m, 5H), 2.48 (s, 3H), 2.53 (m, 2H), 3.24 (t, 2H, J=5.1 Hz), 3.80 (s, 3H), 3.86 (m, 2H), 6.48 (s, 1H), 6.66 (s, 1H), 10.19 (s, 1H). ESI-MS: m/z 441 (MH$^+$).

Example 70

4-Formyl-3-hydroxy-8-methoxy-1,9-dimethyl-11-oxo-11H-dibenzo[b,e][1,4]dioxepine-6-amide This compound was prepared by means of a procedure similar to that used for Example 61 except replacing dimethyl-amine hydrochloride with ammonium bicarbonate.

$^1$HNMR (300 MHz, $d_6$-DMSO): δ2.25 (s, 3H), 2.50 (m, 5H), 3.83 (s, 3H), 6.69 (s, 1H), 6.80 (s, 1H), 10.51 (s, 1H), 12.32 (s, 1H). ESI-MS: m/z 358 ($MH^+$).

Example 71

6-Methyl-3-formyl-4-hydroxy-2-(3-methyl-6-carboxy-2-hydroxy-4-methoxy-phenoxy)-benzoic acid (Compound No:AA3)

Psoromic acid (35 mg, 1 mmol) was dissolved in 1 mol/L of aqueous lithium hydroxide (3 ml), and the reaction is allowed to stand overnight. The solution was acidified to a pH of 4 with 1 mol/L dilute HCl, filtered, and collected to give a white solid product.

$^1$HNMR (300 MHz, $CDCl_3$): δ 2.16 (s, 3H), 2.20 (s, 3H), 3.78 (s, 3H), 6.64 (s, 1H), 7.07 (s, 1H), 10.35 (s, 1H). EI-MS: m/z 376 ($M^+$).

Example 72

4-(1-Hydroxy-propyl)-3,8-dimethoxy-1,9-dimethyl-11-oxo-11H-dibenzo[b,e][1,4]dioxepine-6-carboxylic acid methyl ester The compound from Example 3 (0.15 mmol) was dissolved in absolute tetrahydrofuran. A solution of 2M Grignard reagent (0.7 ml, 1.4 mmol) in tetrahydrofuran was added under ice bath. The mixture was stirred for 1 h. Upon completion, 2 ml of 1N hydrochloric acid was added, and the mixture was extracted with methylene chloride. The organic layer was subsequently washed with water and saturated brine, dried over anhydrous $MgSO_4$, filtered and evaporated by a rotatory evaporator. After chromatographic purification on silica, the title compound was obtained.

Example 73

4-(2-Ethoxycarboxy-methylene)-3,8-dimethoxy-1,9-dimethyl-11-oxo-11H-dibenzo[b,e][1,4]dioxepine-6-carboxylic acid methyl ester The compound from Example 3 (0.24 mmol) and the desired phosphorus ylide (168 mg, 0.48 mmol) were added into 3 ml of toluene. The solution was heated at 80° C. for 14 h under nitrogen protection. Upon completion, the reaction was cooled to room temperature. Methylene chloride was added, and the mixture was washed with 0.1N dilute hydrochloric acid, dried over anhydrous $MgSO_4$, filtered and evaporated by a rotatory evaporator. After chromatographic purification on silica, the title compound was obtained.

Example 74

Dibenzo[b,e][1,4]dioxepin-11-one (Compound No:AA0)

A solution of 2-bromo-benzoic acid (4.02 g, 20 mmol) and potassium carbonate (3.0 g, 22 mol) in acetone (50 mL) was added to benzyl bromine (3.42 g, 2.4 ml, 20 mmol). The reaction was stirred at room temperature overnight, filtered and evaporated by a rotatory evaporator to obtain a colorless oil.

To a solution of benzene-1,2-diol (2.2 g, 20 mmol) and potassium carbonate (3.0 g, 22 mol) in acetone (50 mL) was added benzyl bromine (3.42 g, 2.4 ml, 20 mmol). The reaction was stirred at room temperature overnight, filtered and evaporated by a rotatory evaporator to obtain a colorless oil.

$^1$HNMR (300 MHz, $CDCl_3$): δ 5.11 (s, 2H), 6.50 (m, 1H), 6.95 (m, 3H), 7.40 (m, 5H).

2-Benzyloxy-phenol (200 mg, 1 mmol), 2-Bromo-benzoic acid benzyl ester (291 mg, 1 mmol) and potassium carbonate (201 mg, 1.8 mmol) were charged into a three-neck round bottom flask containing 2 ml of dry pyridine. The reaction mixture was heated at 130° C. for 0.5 h under nitrogen protection. CuO (16 mg, 0.2 mmol) was added to the mixture. The temperature was raised to 150° C. and the reaction was stirred at that temperature for 20 h. Upon completion, the reaction mixture was cooled to room temperature and then it was poured into ice water, acidified to a pH of 6 with 2N HCl. The solution was extracted with ethyl acetate. The organic layer was washed with saturated brine solution, dried over anhydrous $MgSO_4$, filtered and evaporated by a rotatory evaporator. After chromatographic purification on silica, a colorless oil was obtained.

$^1$HNMR (300 MHz, $CDCl_3$): δ 5.04 (s, 2H), 5.33 (s, 2H), 6.81 (d, 1H), 7.03 (m, 7H), 7.18 (m, 4H), 7.25 (m, 3H), 7.37 (m, 2H), 7.93 (d, 1H, J=7.8 Hz)

2-(2-Benzyloxy-phenoxy)-benzoic acid benzyl ester (440 mg, 1 mmol) was dissolved in ethanol (30 mL), and 10% palladium on carbon (44 mg) was added. The mixture was stirred overnight under nitrogen protection. The suspension was filtered, evaporated by a rotatory evaporator to produce 2-(2-hydroxy-phenoxy)-benzoic acid.

$^1$HNMR (300 MHz, $CDCl_3$): δ 6.85 (m, 2H), 6.95 (m, 2H), 7.05 (td, 1H, J=7.2 1.5 Hz), 7.13 (td, 1H, J=7.5 1.2 Hz), 7.42 (td, 1H, J=7.8 1.8 Hz), 7.93 (dd, 1H, J=7.8 1.8 Hz).

2-(2-Hydroxy-phenoxy)-benzoic acid (200 mg) was dissolved in acetic anhydride (10 ml) and refluxed at 145-148° C. for 8 h. The excess acetic anhydride was evaporated by a rotatory evaporator and the residue was poured into ice water. The mixture was extracted with diethyl ether. The organic layer was successively washed with saturated $NaHCO_3$ and saturated ammonium chloride, dried over anhydrous $MgSO_4$, filtered and evaporated by a rotatory evaporator. After dryness and purification by column chromatography, the final product was provided.

$^1$HNMR (300 MHz, $CDCl_3$): δ 7.18 (m, 2H), 7.28 (m, 4H), 7.54 (t, 1H, J=7.2 Hz), 7.93 (d, d, 1H, J=7.8 1.2 Hz), EI-MS, m/z 212.

Example 75

9-Methyl-dibenzo[b,e][1,4]dioxepin-11-one (Compound No:AA2)

This compound was prepared by means of a procedure similar to that used for Example 74 except replacing benzene-1,2-diol of Example 72 with 3-methyl benzene-1,2-diol.

$^1$HNMR (300 MHz, $CDCl_3$): δ 2.48 (s, 3H), 7.04 (m, 2H), 7.11 (q, 1H, J=5.1 Hz), 7.28 (m, 2H), 7.56 (q, d, 1H, J=5.1 1.8 Hz), 7.97 (d, d, 1H, J=5.1 1.8 Hz). EI-MS, m/z 226.

Example 76

6-Methyl-dibenzo[b,e][1,4]dioxepin-11-one (Compound No:AA1)

This compound was prepared by means of a procedure similar to that used for Example 74 except replacing benzene-1,2-diol of Example 72 with 3-methyl benzene-1,2-diol.

$^1$HNMR (300 MHz, CDCl$_3$): δ 2.41 (s, 3H), 7.04 (m, 2H), 7.11 (q, 1H, J=5.1 Hz), 7.28 (m, 2H), 7.56 (q, d, 1H, J=5.1 1.8 Hz), 7.97 (d, d, 1H, J=5.1 1.8 Hz). EI-MS, m/z 226.

Example 77

3-Hydroxy-dibenzo[b,e][1,4]dioxepin-11-one (Compound No:BH2)

This compound was prepared by means of a procedure similar to that used for Example 74, with other reaction conditions following those known in the art.

Example 78

11-Oxo-11H-dibenzo[b,e][1,4]dioxepine-4-carbaldehyde (Compound No:BH9)

2-bromo-1,3-dimethyl-benzene (1.85 g, 10 mmol) and potassium hydroxide (0.28 g, 5 mmol) were added into water (20 ml). KMnO$_4$ (6.32 g 40 mmol) was added portion-wise under refluxing. The reaction mixture was refluxed for several hours. Upon completion, the mixture was cooled, and solid was filtered off. The filtrate was acidified to a pH of 1 with 2N HCl, and then extracted with ethyl acetate. The organic layer was washed with saturated ammonium chloride, dried over anhydrous MgSO$_4$, filtered and evaporated by a rotatory evaporator, to provide a white solid.

$^1$HNMR (300 MHz, d$_6$-DMSO): 7.58 (m, 1H), 7.75 (m, 2H).

To a solution of 2-Bromo-isophthalic acid (0.687 g, 2.8 mmol) and potassium carbonate (0.800 g, 5.8 mol) in acetone (50 mL) was added benzyl bromine (0.958 g, 0.67 ml, 5.6 mmol). The mixture was stirred overnight at room temperature. Upon completion, the mixture was filtered and evaporated by a rotatory evaporator to obtain a colorless oil.

11-Oxo-11H-dibenzo[b,e][1,4]dioxepine-4-carboxylic acid was prepared by means of a procedure similar to that used for Example 74.

To a solution of 11-oxo-11H-dibenzo[b,e][1,4]dioxepine-4-carboxylic acid (256 mg, 1 mmol) in methylene chloride (15 ml) was added BH$_3$-dimethyl sulfide complex (1.6 ml, 1 mol/L in methylene chloride) under ice bath. The mixture was stirred for 30 min at room temperature, refluxed for 5 h and then cooled. The reaction was quenched by addition of methanol, and the whole mixture was evaporated by a rotatory evaporator. The residue was diluted with saturated NaHCO$_3$ (aq) and extracted with AcOEt. The organic layer was washed with saturated brine, dried over anhydrous MgSO$_4$, purified by column chromatography and evaporated by a rotatory evaporator. To a solution of the crude product in CH$_2$Cl$_2$ (20 ml) was added a suspension of pyridinium chlorochromate (PCC, 280 mg, 1.3 mmol) and neutral Al$_2$O$_3$ (350 mg) in CH$_2$Cl$_2$ (20 ml) in ice bath under N$_2$. The mixture was stirred for 18 h at room temperature, filtered, evaporated by a rotatory evaporator, purified by column chromatography to obtain 11-oxo-11H-dibenzo[b,e][1,4]dioxepine-4-carbaldehyde.

Example 79

1-Methyl-dibenzo[b,e][1,4]dioxepin-11-one (Compound No:BI0)

Cuprous bromide was added in one portion to a hot solution (90° C.) of 2-amino-6-methylbenzoic acid (10 g, 66 mmol) and HBr (26 mL, 40%) in H$_2$O (160 ml). This was followed by the dropwise addition of a solution of NaNO$_2$ (13.7 g, 198 mmol) in H$_2$O (40 ml) over a period of 25 min. The reaction mixture was maintained at same temperature for 1 h and then was heated under reflux for another 0.5 h before it was cooled to room temperature and stirred for 2 h. Upon completion, the reaction mixture was carefully poured into ice water (1000 ml), and 5% NaOH solution was added until a pH of 14 was reached. The resulting suspension was filtered. The filtrate was acidified with diluted HCl to a pH of 1 and extracted with Et$_2$O, Charcoal was added, and the resulting mixture was heated to reflux, filtered and evaporated by a rotatory evaporator to give a crude compound, which was recrystallized from Et$_2$O/PE to afford the product (9.28 g, 65%).

$^1$HNMR (300 MHz, CDCl$_3$): δ 7.42 (t, 1H, J=5.1 Hz), 7.1-7.2 (m, 2H), 2.43 (s, 3H).

In the following steps, the compound was prepared by means of a procedure similar to that used for Example 74, with other reaction conditions following those known in the art.

Example 80

8-Methoxy-dibenzo[b,e][1,4]dioxepin-11-one (Compound No:BI1)

m-CPBA (1.72 g 10 mmol) was added in one portion to a solution of 2,4-dimethoxy-benzaldehyde (0.83 g, 5 mmol) in methylene dichloride under ice bath. The reaction mixture was stirred for 3 h under ice bath, and then washed with saturated sodium bicarbonate. The solvent was evaporated off by rotatory evaporation. The residue was dissolved in methanol (30 ml) and potassium hydroxide (0.56 g, 10 mmol) was added under ice bath. The reaction mixture was stirred for 1 hour and methanol was removed by rotary evaporation. The residue was acidified with aqueous 3N HCl and extracted with diethyl ether (100 ml). The organic layer was washed with water, saturated brine, dried over anhydrous MgSO$_4$, filtered and evaporated by a rotary evaporator to obtain the product, which was purified by column chromatography.

$^1$HNMR (300 MHz, CDCl$_3$): δ 3.75 (s, 3H), 3.84 (s, 3H), 6.36 (d, d, 1H, J=8.7, 2.7 Hz), 6.48 (d, 1H, J=2.7 Hz), 6.81 (d, 1H, J=8.4 Hz).

2-(2,4-Dimethoxy-phenoxy)-benzoic acid methyl ester was prepared by means of a procedure similar to that used for Example 74, with other reaction conditions following those known in the art.

A solution of boron trichloride (1 ml of 1 mol/L solution in dichloromethane) in dichloromethane (2 ml) was added to a stirred solution of 2-(2,4-dimethoxy-phenoxy)-benzoic acid methyl ester (0.364 g) in dichloromethane (15 ml) under ice bath. The solution was stirred for 20 min and then stirred at room temperature for 2 h. The solution was carefully poured into ice water and the crude product was extracted with dichloromethane, washed with saturated brine, dried over anhydrous MgSO$_4$, filtered and evaporated by a rotary evaporator to obtain the product, which was purified by column chromatography.

In the following steps, the compound was prepared by means of a procedure similar to that used for Example 74, with other reaction conditions following those known in the art.

Example 81

11-Oxo-11H-dibenzo[b,e][1,4]dioxepine-6-carboxylic acid (Compound No: BI2)

2-Hydroxy-3-methoxy-benzoic acid (1.68 g) was dissolved in methanol and several drops of concentrated sulfuric acid were added to the solution as a catalyst. The mixture was heated under reflux and monitored by TLC. Upon completion, the solvent was evaporated by a rotary evaporator and the residue was dissolved in water, adjusted to a pH of 6 with 1 mol/L aqueous sodium hydroxide, and extracted by ethyl acetate. The organic layer was washed by saturated NaHCO$_3$, dried over anhydrous MgSO$_4$, filtered and evaporated under reduced pressure to obtain a white solid (1.70 g).

In the following steps, the compound was prepared by means of a procedure similar to that used for Example 74, with other reaction conditions following those known in the art.

Example 82

4-Formyl-3-hydroxy-8-methoxy-9-methyl-11-oxo-11H-dibenzo[b,e][1,4]dioxepine-6-carboxylic acid (Compound No: BI4)

This compound was prepared by means of a procedure similar to that used for Example 74, with other reaction conditions following those known in the art.

Example 83

4-Formyl-8-methoxy-1,9-dimethyl-11-oxo-11H-dibenzo[b,e][1,4]dioxepine-6-carboxylic acid (Compound No: BI5)

This compound was prepared by means of a procedure similar to that used for Example 74, with other reaction conditions following those known in the art.

Example 84

3-Hydroxy-8-methoxy-1,9-dimethyl-11-oxo-11H-dibenzo[b,e][1,4]dioxepine-6-carboxylic acid (Compound No: BI7)

This compound was prepared by means of a procedure similar to that used for Example 74, with other reaction conditions following those known in the art.

Example 85

4-Formyl-3-hydroxy-8-methoxy-1-methyl-11-oxo-11H-dibenzo[b,e][1,4]dioxepine-6-carboxylic acid (Compound No: BJ0)

This compound was prepared by means of a procedure similar to that used for Example 74, with other reaction conditions following those known in the art.

Example 86

4-Formyl-3-hydroxy-1,9-dimethyl-11-oxo-11H-dibenzo[b,e]dioxepine-6-carboxylic acid (Compound No: BJ1)

This compound was prepared by means of a procedure similar to that used for Example 74, with other reaction conditions following those known in the art.

Example 87

3-Hydroxy-8-methoxy-1,9-dimethyl-11-oxo-11H-dibenzo[b,e][1,4]dioxepine-4-carbaldehyde (Compound No: BJ2)

This compound was prepared by means of a procedure similar to that used for Example 74, with other reaction conditions following those known in the art.

Example 88

7-Methyl-2-nitro-dibenzo[b,f][1,4]oxazepin-11(10H)one (Compound No: BJ4)

A slurry of 2-chloro-5-nitrobenzoic acid (1.00 g, 5 mmol) and SOCl$_2$ (1.2 ml, 14 mmol), containing 1 drop of DMF, was heated under reflux to obtain a yellow-brown solution. Excess SOCl$_2$ was removed by evaporation under reduced pressure, and the residue was dissolved in THF (5 ml). The resultant acid chloride solution was added dropwise over 30 min to a solution of 6-amino-m-cresol (0.611 g, 5 mmol) and (i-Pr)$_2$NEt (1.73 ml, 10 mmol) in THF (5 ml) under ice bath. The reaction mixture was allowed to react at room temperature for 48 h, the reaction mixture was extracted with Et$_2$O (20 ml), washed successively with 1 N HCl, saturated aqueous NaHCO$_3$, and saturated brine, dried over MgSO$_4$, filtered and evaporated by a rotatory evaporator to obtain a yellow oil (1.30 g, 85%). mp 190-193° C.

$^1$HNMR (300 MHz, d$_6$-DMSO): δ 2.23 (s, 3H), 6.65 (d, 1H, J=8.1 Hz), 6.73 (s, 1H), 7.64 (d, 1H, J=8.1 Hz), 7.84 (d, 1H, J=9.0 Hz), 8.31 (d, d, 1H, J=3.0, 9.0 Hz), 8.43 (d, 1H, J=3.0 Hz), 9.65 (br s, 1H), 9.89 (br s, 1H).

A solution of N-(2-Hydroxy-4-methylphenyl)-2-chloro-5-nitrobenzene carboxamide (530 mg, 1.7 mmol) and 2 N NaOH (0.95 ml, 1.9 mol) in water (5 ml) was heated under reflux for 10 h. The resultant slurry was allowed to stand overnight at room temperature and a copious amount of water was added. The resulting mixture was filtered and solid was collected to obtain the compound (380 mg, 83%). Mp: 274-277° C.

$^1$HNMR (300 MHz, d$_6$-DMSO): δ 2.27 (s, 3H), 7.04-7.11 (m, 2H), 7.23 (s, 1H), 7.60 (d, 1H, J=8.7 Hz), 8.45 (d, d, 1H, J=3.0, 8.7 Hz), 8.52 (d, 1H, J=3.0 Hz), 10.70 (s, 1H).

Example 89

8-Chloro-10H-dibenzo[b,f][1,4]oxazepin-11-one (Compound No: BJ6)

Cs$_2$CO$_3$ (7.43 g, 23 mmol) was added to a solution of 4-chloro-1-fluoro-2-nitrotoluene (2.00 g, 11 mmol) and methyl salicylate (2.92 ml, 23 mmol) in DMF (25 ml). The resulting mixture was stirred for 2 hours at 60° C., after which the reaction mixture was cooled to room temperature and poured into dichloromethane (60 ml). The organic phase was washed with water and saturated brine, dried over anhydrous Na$_2$SO$_4$, filtered and dried to give the crude product 2.80 g (80%), which was sufficiently pure to be used in the next step without further purification.

The crude product (2.8 g, 9.55 mmol) was then dissolved in THF (15 ml) and 2 M LiOH (40 mmol) was added. The reaction mixture was stirred at 60° C. for 2 h and then cooled to room temperature. THF was removed by rotary evaporation and the residue was acidified with HCl (2M) to a pH of 2 and filtered. The filter cake washed with 0.1M NaOH solution and finally dried to give the crude product 2.4 g (86%). Na$_2$S$_2$O$_4$ (37 mmol) was added to a solution of the crude product in 2M K$_2$CO$_3$ (41 mmol) and EtOH (20 ml) and the reaction was stirred for 15 min. EtOH was then removed by rotary evaporation and the resulting aqueous layer was acidified with HCl (2M) to a pH of 2 and extracted with ethyl acetate. The organic layer was washed with saturated brine, dried over anhydrous Na$_2$SO$_4$, filtered and evaporated by a rotary evaporator to give the crude product 1.1 g (52%). Finally, the crude product (1.1 g, 4.2 mmol), EDCI (1.20 g, 6.3 mmol), HOBt (851 mg, 6.3 mmol), DMAP (5 mg, 0.04 mmol) and TEA (18.9 mmol) were dissolved in MeCN (8 ml), and the resulting solution was heated to 140° C. in microwave for 10 min. The reaction mixture was cooled, poured into water, acidified with HCl (2M) to a pH of 2 and filtered. The filtrate was washed with 0.1 M NaOH solution and dried over anhydrous Na$_2$SO$_4$, filtered and evaporated by a rotary evaporator to give the product (676 mg, 66%).

$^1$HNMR (300 MHz, d$_6$-DMSO): 7.12-7.20 (m, 2H), 7.28-7.38 (m, 3H), 7.58-7.64 (m, 1H), 7.76 (d, d, 1H, J=7.8, 1.5 Hz), 10.61 (br s, 1H).

Example 90

8-Chloro-5,10-dihydro-11H-dibenzo[b,e][1,4]diazepin-11-one (Compound No: BK0)

A mixture of ortho-nitrobenzoic acid (1.38 g, 10.1 mmol), 2-bromo-5-chloronitrobenzene (2.50 g, 10.6 mmol), anhydrous potassium carbonate (1.39 g, 10.1 mmol), 3-methylbutan-1-ol (20 ml) and copper powder (50 mg) was heated under reflux for 4 h. The mixture was cooled and 3-methylbutan-1-ol was removed by rotary evaporation. The resultant mixture was poured into water and acidified with aqueous hydrochloric acid (2M) until the mixture was acidic and precipitate was formed. The mixture was filtered and the resultant crude product was recrystallization from ethanol to give the product (2.18 g, 74%), m.p. 246-248° C.

$^1$HNMR (300 MHz, d$_6$-acetone): 7.14 (d, d, d, 1H, J=8.1, 6.0, 2.1 Hz), 7.52-7.63 (m, 3H), 7.74 (d, 1H, J=9.0 Hz), 8.11 (d, d, 1H, J=8.1, 0.9 Hz), 8.15 (d, 1H, J=3.0 Hz), 11.11 (s, 1H).

A mixture of 2-(4-Chloro-2-nitro-phenylamino)-benzoic acid (1.00 g, 3.42 mmol) in aqueous ammonia (2M, 25 ml) was heated to 80° C. to form a red/crimson solution, sodium dithionite (3.57 g, 20.5 mmol) was added in one portion to the solution, making the solution change to yellow colour. Activated carbon was added and the mixture was filtered whilst hot. The filtrate was adjusted to a pH of 4.5 with glacial acetic acid and filtered. The filter cake was collected. The crude product was recrystallization from methanol/water to afford the product as yellow needles (0.56 g, 64%), m.p. 198-200° C.

$^1$HNMR (300 MHz, d$_6$-DMSO): 5.22 (br s, 2H), 6.54-6.63 (m, 2H), 6.69 (d, d, d, 1H, J=8.1, 6.9, 0.9 Hz), 6.84 (d, 1H, J=2.1 Hz), 7.03 (d, 1H, J=8.1 Hz), 7.30 (d, d, d, 1H, J=9.0, 6.9, 2.1 Hz), 7.87 (d, d, 1H, J=8.1, 2.1 Hz), 8.98 (s, 1H), 12.91 (br s, 1H).

A mixture of 2-(2-Amino-4-chloro-phenylamino)-benzoic acid (10.0 g, 38.1 mmol) and xylenes (250 ml) was heated for 96 h. The reaction mixture was then cooled, evaporated by a rotary evaporator and the resulting residue was washed with hot aqueous ammonia (2M, 100 ml). The crude product was recrystallized from acetone/water to give the product (7.40, 79%), m.p. 232-233° C.

$^1$HNMR (300 MHz, d$_6$-acetone): 6.95 (d, d, d, 1H, J=8.1, 6.9, 0.9 Hz), 6.98 (d, d, 1H, J=8.1, 2.1 Hz), 7.03 (d, d, 1H, J=8.1, 0.9 Hz), 7.06 (d, 1H, J=8.1 Hz), 7.15 (d, 1H, J=2.1 Hz), 7.29 (s, 1H), 7.36 (d, d, d, 1H, J=8.1, 6.9, 0.9 Hz), 7.84 (d, d, 1H, J=8.1, 2.1 Hz), 9.01 (s, 1H).

Example 91

8-chloro-10H-Dibenzo[b,f][1,4]thiazepin-11-one (Compound No: BK2)

This compound was prepared by means of a procedure similar to that used for Example 87 except replacing methyl salicylate of Example 87 with methyl thiosalicylate.

M.p. 295-300° C. $^1$HNMR (300 MHz, d$_6$-DMSO): 7.20 (d, d, 1H, J=8.1, 2.4 Hz), 7.28 (d, 1H, J=2.4 Hz), 7.51 (m, 4H), 7.68 (m, 1H), 10.72 (br s, 1H)

Example 92

11H-dibenzo[b,e][1.4]-oxathiepin-11-one (Compound No: BK3)

A mixture of n-amyl alcohol (17 ml), thiosalicylic acid (4.9 g, 30 mmol), 2-iodoanisole (7.5 g, 30 mmol), anhydrous K$_2$CO$_3$ (4.6 g) and copper acetate (0.1 g) was refluxed for 16 hours. Upon completion, the reaction mixture was cooled, and aqueous sodium hydroxide (25%, 25 ml) was added. Amyl alcohol was evaporated. The aqueous layer was acidified with HCl to obtain the solid product (8 g, yield: 96.3%). m.p. 203° C.

A mixture of the 2-(2-methoxy-phenylsulfanyl)-benzoic acid (5 g, 10 mmol), hydrobromic acid (60%) (25 ml) and acetic acid (10 ml) was refluxed for 2 h at 135-140° C. Upon completion, the reaction mixture was cooled and carefully poured into ice water. The mixture was extracted with diethyl ether. The organic layer was washed with saturated sodium bicarbonate. The aqueous layer was acidified with HCl, filtered to obtain the solid product (2 g, 42%). m.p. 175° C.

2-(2-Hydroxy-phenylsulfanyl)-benzoic acid (2 g, 8 mmol) was dissolved in acetic anhydride and the resultant solution was refluxed at 145-148° C. for 8 h. Upon completion, the excess acetic anhydride was removed by rotary evaporation and the residue was poured into ice water. The mixture was extracted with diethyl ether. The organic layer was washed with saturated brine, dried over anhydrous MgSO$_4$, filtered, evaporated by a rotatory evaporator and purified by column chromatography to obtain the product (1 g, 54%). m.p. 124° C.

Example 93

Dibenzo[b,e][1,4]oxazepin-11(5H)-one (Compound No: BK4)

A solution of potassium 2-bromobenzoate (0.1 mol) and 2-aminophenol (0.20 mol) in n-BuOH (50 ml) was heated to 100° C., Cu powder (0.1 g) was added, and the reaction mixture was refluxed for 30 min. Upon completion, the mixture was cooled, NaHCO$_3$ (2.5 g) was added followed by rotary evaporation to remove the solvent. To the residue was added a saturated solution of NaHCO$_3$ (25 ml), and the mixture was filtered. The filtrate was acidified with 6N HCl and a solid precipitated out. This mixture was heated to 60° C. and filtered whist hot, the filter cake was washed with a small amount of water, dissolved in EtOH, and passed through a charcoal column to remove color. After filtration and rotary evaporation of the solvent, the resultant crude product was sufficiently pure to be used in the next step without further purification.

A solution of 2-(2-Hydroxy-phenylamino)-benzoic acid (2.0 g, 9 mmol) and p-toluenesulfonic acid (0.5 g) in toluene (200 ml) was heated under $N_2$ with the $H_2O$ formed being collected in a Dean-Stark receiver. Upon completion, the organic layer was washed with saturated $NaHCO_3$, dried over anhydrous $MgSO_4$, filtered, and evaporated by a rotatory evaporator to obtain the product (1.0 g, 53%).

Example 94

4-Formyl-3-hydroxy-8-methoxy-1,9-dimethyl-11-oxo-10,11-dihydro-dibenzo[b,f][1,4]oxazepine-6-carboxylic acid (Compound No: BK5)

This compound was prepared by means of a procedure similar to that used for Example 88, with other reaction conditions following those known in the art.

Example 95

4-Formyl-3-hydroxy-8-methoxy-1,9-dimethyl-11-oxo-10,11-dihydro-dibenzo[b,e][1,4]diazepine-6-carboxylic acid (Compound No: BK8)

This compound was prepared by means of a procedure similar to that used for Example 90, with other reaction conditions following those known in the art.

Example 96

4-Formyl-3-hydroxy-8-methoxy-1,9-dimethyl-11-oxo-10,11-dihydro-dibenzo[b][1,4]thiazepine-6-carboxylic acid (Compound No: BL0)

This compound was prepared by means of a procedure similar to that used for Example 91, with other reaction conditions following those known in the art.

Example 97

4-Formyl-3-hydroxy-8-methoxy-1,9-dimethyl-11-oxo-10,11-dihydro-dibenzo[b,f][1,4]oxathiepine-6-carboxylic acid (Compound No: BL2)

This compound was prepared by means of a procedure similar to that used for Example 92, with other reaction conditions following those known in the art.

Example 98

4-Formyl-3-hydroxy-8-methoxy-1,9-dimethyl-11-oxo-5,10-dihydro-dibenzo[b,e][1,4]oxazepine-6-carboxylic acid (Compound No: BL7)

This compound was prepared by means of a procedure similar to that used for Example 93, with other reaction conditions following those known in the art.

Example 99

9-Ethoxymethyl-4-formyl-3,8-dimethoxy-1,6-dimethyl-11-oxo-11H-dibenzo[b,e][1,4]dioxepine-7-carboxylic acid methyl ester (Compound No: BM0)

The compound was prepared by means of a procedure similar to that used for Example 2 except replacing psoromic acid with 9-Ethoxymethyl-4-formyl-3,8-dimethoxy-1,6-dimethyl-11-oxo-11H-dibenzo[b,e][1,4]dioxepine-7-carboxylic acid.

$^1$HNMR (300 MHz, $CDCl_3$): δ 1.19 (t, 3H, J=7.5 Hz), 2.21 (s, 3H), 2.51 (s, 3H), 3.57 (q, 2H, J=7.5 Hz), 3.81 (s, 3H), 3.88 (s, 3H), 3.93 (s, 3H), 4.57 (s, 2H), 6.69 (s, 1H), 10.61 (s, 1H).

Example 100

3,8-Diethoxy-9-ethoxymethyl-4-formyl-1,6-dimethyl-11-oxo-11H-dibenzo[b,e][1,4]dioxepine-7-carboxylic acid ethyl ester (Compound No: BM2)

The compound was prepared by means of a procedure similar to that used for Example 2 except replacing iodomethane with iodoethane.

$^1$HNMR (300 MHz, $CDCl_3$): δ 1.19 (t, 3H, J=6.9 Hz), 1.32 (m, 6H), 1.47 (t, 3H, J=6.9 Hz), 2.22 (s, 3H), 2.49 (s, 3H), 3.57 (q, 2H, J=7.2 Hz), 3.97 (q, 2H, J=6.9 Hz), 4.17 (q, 2H, J=6.9 Hz), 4.33 (q, 2H, J=7.2 Hz), 4.56 (s, 2H), 6.66 (s, 1H), 10.58 (s, 1H).

Example 101

9-Ethoxymethyl-4-formyl-1,6-dimethyl-11-oxo-3,8-dipropoxy-11H-dibenzo[b,e][1,4]dioxepine-7-carboxylic acid propyl ester (Compound No: BM7)

The compound was prepared by means of a procedure similar to that used for Example 2 except replacing iodomethane with iodopropane.

$^1$HNMR (300 MHz, $CDCl_3$): δ 0.98 (m, 6H), 1.18 (m, 6H), 1.72 (m, 6H), 2.22 (s, 3H), 2.49 (s, 3H), 3.57 (q, 2H, J=6.9 Hz), 387 (t, 2H, J=6.3 Hz), 4.03 (t, 2H, J=6.0 Hz), 4.33 (t, 2H, J=6.6 Hz), 4.56 (s, 2H), 6.66 (s, 1H), 10.58 (s, 1H).

Example 102

3,8-Dibutoxy-9-ethoxymethyl-4-formyl-1,6-dimethyl-11-oxo-11H-dibenzo[b,e][1,4]dioxepine-7-carboxylic acid butyl ester (Compound No: BN0)

The compound was prepared by means of a procedure similar to that used for Example 2 except replacing iodomethane with iodobutane.

$^1$HNMR (300 MHz, $CDCl_3$): δ 0.96 (m, 6H), 1.21 (t, 6H, J=6.9 Hz), 1.38 (m, 6H), 1.75 (m, 6H), 2.22 (s, 3H), 2.50 (s, 3H), 3.57 (q, 2H, J=6.9 Hz), 3.91 (t, 2H, J=6.3 Hz), 4.09 (t, 2H, J=6.3 Hz), 4.33 (t, 2H, J=6.6 Hz), 4.56 (s, 2H), 6.66 (s, 1H), 10.59 (s, 1H).

Example 103

9-Ethoxymethyl-4-formyl-1,6-dimethyl-11-oxo-3,8-bis-pentyloxy-11H-dibenzo[b,e][1,4]dioxepine-7-carboxylic acid pentyl ester (Compound No: BN1)

The compound was prepared by means of a procedure similar to that used for Example 2 except replacing iodomethane with iodopentane.

Example 104

9-Ethoxymethyl-4-formyl-3,8-dihydroxy-1,6-dimethyl-11-oxo-11H-dibenzo[b,e][1,4]dioxepine-7-carboxylic acid methyl ester (Compound No: BN2)

The compound was prepared by means of a procedure similar to that used for Example 3, with other reaction conditions following those known in the art.
$^1$HNMR (300 MHz, CDCl$_3$): δ 1.20 (t, 3H, J=7.5 Hz), 2.49 (s, 3H), 2.55 (s, 3H), 3.60 (q, 2H, J=7.5 Hz), 3.93 (s, 3H), 4.71 (s, 2H), 6.68 (s, 1H), 10.68 (s, 1H), 11.22 (s, 1H), 12.18 (s, 1H).

Example 105

9-Ethoxymethyl-4-formyl-3,8-dihydroxy-1,6-dimethyl-11-oxo-11H-dibenzo[b,e][1,4]dioxepine-7-carboxylic acid ethyl ester (Compound No: BN3)

The compound was prepared by means of a procedure similar to that used for Example 3 except replacing iodomethane with iodoethane.
$^1$HNMR (300 MHz, CDCl$_3$): δ 1.20 (t, 3H, J=7.5 Hz), 1.47 (t, 3H, J=6.9 Hz), 2.49 (s, 3H), 2.55 (s, 3H), 3.60 (q, 2H, J=7.5 Hz), 3.97 (q, 2H, J=6.9 Hz), 4.71 (s, 2H), 6.68 (s, 1H), 10.68 (s, 1H), 11.32 (s, 1H), 12.18 (s, 1H).

Example 106

9-Ethoxymethyl-4-formyl-3,8-dihydroxy-1,6-dimethyl-11-oxo-11H-dibenzo[b,e][1,4]dioxepine-7-carboxylic acid propyl ester (Compound No: BN4)

The compound was prepared by means of a procedure similar to that used for Example 3 except replacing iodomethane with iodopropane. $^1$HNMR (300 MHz, CDCl$_3$): δ 0.99 (t, 3H, J=6.6 Hz), 1.20 (t, 3H, J=6.9 Hz), 1.78 (m, 2H), 2.49 (s, 3H), 2.57 (s, 3H), 3.59 (q, 2H, J=6.9 Hz), 4.33 (t, 2H, J=6.6 Hz), 4.70 (s, 2H), 6.68 (s, 1H), 10.69 (s, 1H), 11.38 (s, 1H), 12.18 (s, 1H).

Example 107

9-Ethoxymethyl-4-formyl-3,8-dihydroxy-1,6-dimethyl-11-oxo-11H-dibenzo[b,e][1,4]dioxepine-7-carboxylic acid butyl ester (Compound No: BN5)

The compound was prepared by means of a procedure similar to that used for Example 3 except replacing iodomethane with iodobutane.

Example 108

9-Ethoxymethyl-4-formyl-3,8-dihydroxy-1,6-dimethyl-11-oxo-11H-dibenzo[b,e][1,4]dioxepine-7-carboxylic acid pentyl ester (Compound No: BN6)

The compound was prepared by means of a procedure similar to that used for Example 3 except substituting iodomethane with iodopentane.

Example 109

9-Ethoxymethyl-3,8-dihydroxy-4-hydroxymethyl-1,6-dimethyl-11-oxo-11H-dibenzo[b,e][1,4]dioxepine-7-carboxylic acid (Compound No: BN9)

The compound was prepared by means of a procedure similar to that used for Example 51, with other reaction conditions following those known in the art.
$^1$HNMR (300 MHz, d$_6$-DMSO): δ 1.16 (t, 3H, J=7.5 Hz), 2.37 (s, 3H), 2.79 (s, 3H), 3.55 (q, 2H, J=7.5 Hz), 4.66 (d, 4H), 6.49 (s, 1H).

Example 110

9-Ethoxymethyl-3,8-dihydroxy-1,6-dimethyl-11-oxo-4-phenylaminomethyl-11H-dibenzo[b,e][1,4]dioxepine-7-carboxylic acid (Compound No: BO1)

The compound was prepared by means of a procedure similar to that used for Example 18 except replacing ethanolamine with aniline.

Example 111

4-(Benzylamino-methyl)-9-ethoxymethyl-3,8-dihydroxy-1,6-dimethyl-11-oxo-11H-dibenzo[b,e][1,4]dioxepine-7-carboxylic acid (Compound No: BO2)

The compound was prepared by means of a procedure similar to that used for Example 18 except replacing ethanolamine with benzyl amine.

Example 112

9-Ethoxymethyl-3,8-dihydroxy-1,6-dimethyl-11-oxo-4-[(2-pyrrolidin-1-yl-ethylamino)-methyl]-11H-dibenzo[b,e][1,4]dioxepine-7-carboxylic acid (Compound No: BO3)

The compound was prepared by means of a procedure similar to that used for Example 18 except replacing ethanolamine with 2-pyrrol-1-yl-ethylamine.

Example 113

9-Ethoxymethyl-3,8-dihydroxy-1,6-dimethyl-11-oxo-4-[(4-sulfamoyl-phenylamino)-methyl]-11H-dibenzo[b,e][1,4]dioxepine-7-carboxylic acid (Compound No: BO4)

The compound was prepared by means of a procedure similar to that used for Example 18 except replacing ethanolamine with sulfanilamide.
$^1$HNMR (300 MHz, d$_6$-DMSO): δ 1.06 (t, 3H, J=6.9 Hz), 2.31 (s, 3H), 2.57 (s, 3H), 3.40 (q, 2H, J=6.9 Hz), 4.38 (s, 2H), 4.49 (s, 2H), 6.75 (m, 3H), 7.52 (d, 2H, J=8.7 Hz).

Example 114

9-Ethoxymethyl-3,8-dihydroxy-1,6-dimethyl-4-[(2-morpholin-4-yl-ethylamino)-methyl]-11-oxo-11H-dibenzo[b,e][1,4]dioxepine-7-carboxylic acid (Compound No: BO7)

The compound was prepared by means of a procedure similar to that used for Example 18 except replacing ethanolamine with 2-morpholin-4-yl-ethylamine.

Example 115

9-Ethoxymethyl-3,8-dihydroxy-1,6-dimethyl-4-(morpholin-4-ylmethyl)-11-oxo-11H-dibenzo[b,e][1,4]dioxepine-7-carboxylic acid (Compound No: BP0)

The compound was prepared by means of a procedure similar to that used for Example 18 except replacing ethanolamine with morpholine.
$^1$HNMR (300 MHz, $d_6$-DMSO): δ 1.06 (t, 3H, J=6.9 Hz), 2.35 (s, 3H), 2.59 (s, 3H), 3.06 (t, 4H), 3.40 (q, 2H, J=6.9 Hz), 3.80 (t, 4H), 4.47 (s, 2H), 4.52 (s, 2H), 6.95 (s, 1H).

Example 116

9-Ethoxymethyl-3,8-dihydroxy-1,6-dimethyl-11-oxo-4-(piperazin-1-ylmethyl)-11H-dibenzo[b,e][1,4]dioxepine-7-carboxylic acid (Compound No: BP2)

The compound was prepared by means of a procedure similar to that used for Example 18 except replacing ethanolamine with piperazine.
$^1$HNMR (300 MHz, $d_6$-DMSO): δ 1.16 (t, 3H, J=6.9 Hz), 2.38 (s, 3H), 2.72 (s, 3H), 2.90 (t, 4H), 3.49 (q, 2H, J=6.9 Hz), 4.18 (t, 4H), 4.55 (s, 2H), 4.68 (s, 2H), 6.63 (s, 1H).

Example 117

4-(tert-Butylamino-methyl)-9-ethoxymethyl-3,8-dihydroxy-1,6-dimethyl-11-oxo-11H-dibenzo[b,e][1,4]dioxepine-7-carboxylic acid (Compound No: BP3)

The compound was prepared by means of a procedure similar to that used for Example 18 except replacing ethanolamine with tert-butylamine.

Example 118

4-(4-Benzyl-piperazin-1-ylmethyl)-9-ethoxymethyl-3,8-dihydroxy-1,6-dimethyl-11-oxo-11H-dibenzo[b,e][1,4]dioxepine-7-carboxylic acid (Compound No: BP6)

The compound was prepared by means of a procedure similar to that used for Example 18 except replacing ethanolamine with benzyl piperazine.
$^1$HNMR (300 MHz, $d_6$-DMSO): δ 1.06 (t, 3H, J=6.9 Hz), 2.30 (s, 3H), 2.58 (s, 3H), 3.40 (m, 10H), 3.80 (t, 4H), 4.32 (s, 2H) 4.52 (s, 2H), 4.68 (s, 2H), 6.77 (s, 1H), 7.45 (m, 2H), 7.62 (m, 3H).

Example 119

4-[(Cyclohexylmethyl-amino)-methyl]-9-ethoxymethyl-3,8-dihydroxy-1,6-dimethyl-11-oxo-11H-dibenzo[b,e][1,4]dioxepine-7-carboxylic acid (Compound No: BP7)

The compound was prepared by means of a procedure similar to that used for Example 18 except replacing ethanolamine with cyclohexane methyl amine.

Example 120

4-[(4-Acetylamino-phenylamino)-methyl]-9-ethoxymethyl-3,8-dihydroxy-1,6-dimethyl-11-oxo-11H-dibenzo[b,e][1,4]dioxepine-7-carboxylic acid (Compound No: BP9)

The compound was prepared by means of a procedure similar to that used for Example 18 except replacing ethanolamine with p-acetylamino phenylamine.

Example 121

4-[(3-Cyano-phenylamino)-methyl]-9-ethoxymethyl-3,8-dihydroxy-1,6-dimethyl-11-oxo-11H-dibenzo[b,e][1,4]dioxepine-7-carboxylic acid (Compound No: BQ1)

The compound was prepared by means of a procedure similar to that used for Example 18 except replacing ethanolamine with 3-cyano-phenylamine.

Example 122

9-Ethoxymethyl-3,8-dihydroxy-1,6-dimethyl-11-oxo-4-[(2-piperidin-1-yl-ethylamino)-methyl]-11H-dibenzo[b,e][1,4]dioxepine-7-carboxylic acid (Compound No: BQ2)

The compound was prepared by means of a procedure similar to that used for Example 18 except replacing ethanolamine with 2-piperidin-1-yl-ethylamine.
$^1$HNMR (300 MHz, $d_6$-DMSO): δ 1.16 (t, 3H, J=6.9 Hz), 1.93 (m, 6H), 2.42 (s, 3H), 2.75 (s, 3H), 3.49 (q, 2H, J=6.9 Hz), 4.62 (s, 2H), 4.68 (s, 2H), 6.77 (s, 1H).

Example 123

9-Ethoxymethyl-3,8-dihydroxy-1,6-dimethyl-11-oxo-4-(pyridin-2-ylaminomethyl)-11H-dibenzo[b,e][1,4]dioxepine-7-carboxylic acid (Compound No: BQ4)

The compound was prepared by means of a procedure similar to that used for Example 18 except replacing ethanolamine with 2-amino-pyridine.

Example 124

9-Ethoxymethyl-4-[(4-fluoro-phenylamino)-methyl]-3,8-dihydroxy-1,6-dimethyl-11-oxo-11H-dibenzo[b,e][1,4]dioxepine-7-carboxylic acid (Compound No: BQ6)

The compound was prepared by means of a procedure similar to that used for Example 18 except replacing ethanolamine with p-fluoro-phenylamine.

Example 125

4-[(4-Amino-phenylamino)-methyl]-9-ethoxymethyl-3,8-dihydroxy-1,6-dimethyl-11-oxo-11H-dibenzo[b,e][1,4]dioxepine-7-carboxylic acid (Compound No: BQ7)

The compound was prepared by means of a procedure similar to that used for Example 18 except replacing ethanolamine with p-phenylene diamine.

Example 126

9-Ethoxymethyl-3,8-dihydroxy-1,6-dimethyl-11-oxo-4-(pyrimidin-2-ylaminomethyl)-11H-dibenzo[b,e][1,4]dioxepine-7-carboxylic acid (Compound No: BQ9)

The compound was prepared by means of a procedure similar to that used for Example 18 except replacing ethanolamine with 2-amino pyrimidine.
$^1$HNMR (300 MHz, $d_6$-DMSO): δ 1.16 (t, 3H, J=7.5 Hz), 2.37 (s, 3H), 2.84 (s, 3H), 3.55 (q, 2H, J=7.5 Hz), 4.55 (s, 2H), 4.66 (s, 2H), 6.65 (m, 2H), 8.26 (m, 2H).

Example 127

9-Ethoxymethyl-3,8-dihydroxy-1,6-dimethyl-11-oxo-4-(piperidin-1-ylmethyl)-11H-dibenzo[b,e][1,4]dioxepine-7-carboxylic acid (Compound No: BR1)

The compound was prepared by means of a procedure similar to that used for Example 18 except replacing ethanolamine with piperidine.
$^1$HNMR (300 MHz, $d_6$-DMSO): δ 1.16 (t, 3H, J=7.5 Hz), 1.80 (m, 6H), 2.46 (s, 3H), 2.76 (s, 3H), 3.11 (t, 4H, J=5.1 Hz), 3.55 (q, 2H, J=7.5 Hz), 4.62 (s, 2H), 4.67 (s, 2H), 6.77 (s, 1H).

Example 128

9-Ethoxymethyl-4-formyl-3,8-dihydroxy-1,6-dimethyl-11-oxo-11H-dibenzo[b,e][1,4]dioxepine-7-carboxylic acid dimethylamide (Compound No: BR3)

The compound was prepared by means of a procedure similar to that used for Example 61, with other reaction conditions following those known in the art.

Example 129

9-Ethoxymethyl-4-formyl-3,8-dihydroxy-1,6-dimethyl-11-oxo-11H-dibenzo[b,e][1,4]dioxepine-7-carboxylic acid diethylamide (Compound No: BR6)

The compound was prepared by means of a procedure similar to that used for Example 61 except replacing dimethylamine hydrochloride with diethylamine hydrochloride.

Example 130

9-Ethoxymethyl-4-formyl-3,8-dihydroxy-1,6-dimethyl-11-oxo-11H-dibenzo[b,e][1,4]dioxepine-7-carboxylic acid ethylamide (Compound No: BR8)

The compound was prepared by means of a procedure similar to that used for Example 61 except replacing dimethylamine hydrochloride with ethylamine hydrochloride.

Example 131

9-Ethoxymethyl-4-formyl-3,8-dihydroxy-1,6-dimethyl-11-oxo-11H-dibenzo[b,e][1,4]dioxepine-7-carboxylic acid methylamide (Compound No: BS0)

The compound was prepared by means of a procedure similar to that used for Example 61 except replacing dimethylamine hydrochloride with methylamine hydrochloride.

Example 132

9-Ethoxymethyl-4-formyl-3,8-dihydroxy-1,6-dimethyl-11-oxo-11H-dibenzo[b,e][1,4]dioxepine-7-carboxylic acid (2-morpholin-4-yl-ethyl)-amide (Compound No: BS2)

The compound was prepared by means of a procedure similar to that used for Example 61 except replacing dimethylamine hydrochloride with 2-morpholin-4-yl-ethylamine.

Example 133

9-Ethoxymethyl-3,8-dihydroxy-1,6-dimethyl-7-(4-methyl-piperazine-1-carbonyl)-11-oxo-11H-dibenzo[b,e][1,4]dioxepine-4-carbaldehyde (Compound No: BS5)

The compound was prepared by means of a procedure similar to that used for Example 61 except replacing dimethylamine hydrochloride with 4-methyl piperazine.

Example 134

8-methoxy-1,9-dimethyl-11-oxo-10,11-dihydro-5-oxa-4,10-aza-dibenzoazepin[a,d]cycloheptene-6-benzoic acid (Compound No: BT1)

Ethyl 2-hydroxy-4-methylnicotinate (1.2 mmol) and 6-bromo-3-methoxy-2-methylbenzenamine (1 mmol) was dissolved in DMSO. $K_2CO_3$ (2 mmol), CuI (0.1 mmol), 4,7-dimethoxy-1,10-phenanthroline (0.15 mmol) were added into the solution. The reaction mixture was heated at 150° C. for 96 hours under $N_2$ atmosphere. Upon completion, the reaction mixture was poured into water and extracted with ethyl acetate. The organic layer was subsequently washed with saturated $NaHCO_3$ solution and saturated brine, and dried over anhydrous $MgSO_4$, filtered, evaporated by a rotatory evaporator and purified by column chromatography to give the desired product.

The solid (1 mmol) from above step was dissolved in 3 mol/L LiOH solution (3 ml), and stirred overnight. Upon completion, the resulting solution was neutralized with 1 N diluted HCl. The precipitated solid was filtered and dried to give the desired product.

The solid (1 mmol) from above step, EDCI (1.5 mmol) and HOBt (1.5 mmol) were dissolved in $CH_2Cl_2$ (5 ml) and the reaction was stirred overnight. Upon completion, the solution was evaporated by a rotatory evaporator and purified by column chromatography to give the desired products.

Example 135

2-Chloro-3-hydroxy-8-methoxy-5,10-dihydro-dibenzo[b,e][1,4]diazepin-11-one (Compound No: BT5)

The compound was prepared by means of a procedure similar to that used for Example 88, with other reaction conditions following those known in the art.

Example 136

8-Methyl-5-oxo-6,11-dihydro-5H-benzo[b]pyrido[2,3-e][1,4]diazepine-10-carboxylic acid (Compound No: BT7)

The compound was prepared by means of a procedure similar to that used for Example 134, with other reaction conditions following those known in the art.

Example 137

9-Hydroxy-3-methoxy-6-oxo-6,11-dihydro-5H-benzo[e]pyrido[3,2-b][1,4]diazepine-10-carbaldehyde (Compound No: BU0)

The compound was prepared by means of a procedure similar to that used for Example 134, with other reaction conditions following those known in the art.

Example 138

Compound G0 isolated from *Cladonia gracilis* (L.) Willd. *Cladonia gracilis* (L.) Willd was percolated by 75% ethanol three times. The extract was concentrated into extractum (230 g), then mixed with silica (200 g) and purified on silica gel column, gradiently eluted with $CH_2Cl_2$: MeOH (100:2) to provide a solid as a white powder. The solid was recrystallized from acetone to obtain compound G0 (about 10 g). The structure of G0 was 9-Ethoxymethyl-4-formyl-3,8-dihydroxy-1,6-dimethyl-11-oxo-11H-dibenzo[b,e][1,4]dioxepine-7-carboxylic acid characterized by $^1$H-NMR, $^{13}$C-NMR, HMBC and EI, the molecular formula of which was $C_{20}H_{18}O_9$. The structure was as follows:

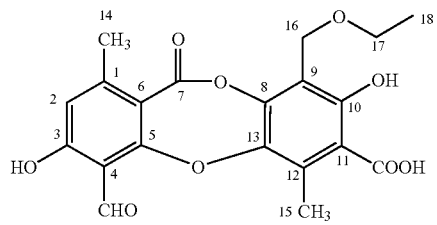

$^1$H-NMR: 1.11 (3H), 3.45 (2H), 4.53 (2H), 6.82 (1H), 10.59 (1H); $^{13}$C-NMR: 14.5 ($CH_3$), 15.2 ($CH_3$), 21.3 ($CH_3$), 60.4 ($CH_2$), 65.1 ($CH_2$), 111.9, 112.1, 116.1, 116.3, 117.1 (CH), 130.7, 142.3, 145.5, 151.8, 154.7, 161.0, 163.7, 164.1, 170.2, 191.6; EI 402(12), 358(12), 356(100), 338(28), 326 (20), 310(40), 300(8), 285(40), 268(12), 258(24), 230(20), 217(12), 179(20), 151(8), 150(20), 77(12), 67(12), 59 (16).

Example 139

Compound F7 Isolated from *Lethariella cladonioides*

*Lethariella cladonioides* (25 kg) was crushed into pieces, and then extracted under refluxing with 75% ethanol three times, with the period of 3 h, 2 h and 2 h, respectively. Total amount of 75% ethanol used was 500 kg. The extract was filtered and concentrated under reduced pressure into extractum (9.2 kg). The extractum was resuspended into water, extracted with ethyl acetate three times to obtain an organic portion (1.5 kg) and an aqueous portion. The ethyl acetate phase (250 g) was dissolved in an organic solvent and mixed thoroughly with silica gel (250 g, 200-300 mesh), and then concentrated under reduced pressure to dryness. The silica gel (1.2 g, 200-300 mesh) and $CH_2Cl_2$ were packed into a column (12×150 cm) by a wet method. After balance procedure, a sample was charged into the column by a wet method. The column was eluted by $CH_2Cl_2$ (3 L), $CH_2Cl_2$:MeOH (100:1, 3 L; 100:3, 6 L; 100:5, 9 L; 100:10, 6 L) respectively to get five components F-1, F-2, F-3, F-4 and F-5. The F-5 containing the desired compound was condensed under reduced pressure to dryness, dissolved in methanol and filtered repeatedly. The filtered stuff was recrystallized from $CH_2Cl_2$/EtOH to get a pure compound (3.6 g), which was characterized by spectrum to be psoromic acid.

$^1$H-NMR (CDCl$_3$): δ 11.83 (1H, s, OH-3), 10.09 (1H, s, 4-CHO), 6.60 (1H, s, H-7), 6.20 (1H, s, H-2), 3.36 (3H, s, 8-OCH$_3$), 2.08 (3H, s. 1-CH$_3$), 1.77 (3H, s. 9-CH$_3$).

$^{13}$C-NMR (CDCl$_3$): δ 152.8 (C-1), 117.1 (C-2), 164.9 (C-3), 110.5 (C-4), 122.3 (C-6), 107.6 (C-7), 154.5 (C-8), 123.3 (C-9), 165.1 (C-11), 111.5 (C-1a), 161.0 (C-4a), 143.1 (C-5a), 143.3 (C-9a), 21.9 (1-OCH$_3$), 195.1 (4-CHO), 165.9 (6-COOH), 9.5 (9-CH$_3$).

Example 140

Technology of Obtaining Arginine Salt of F7

The process of preparing the arginine salt of compound F7 was shown in the following equation:

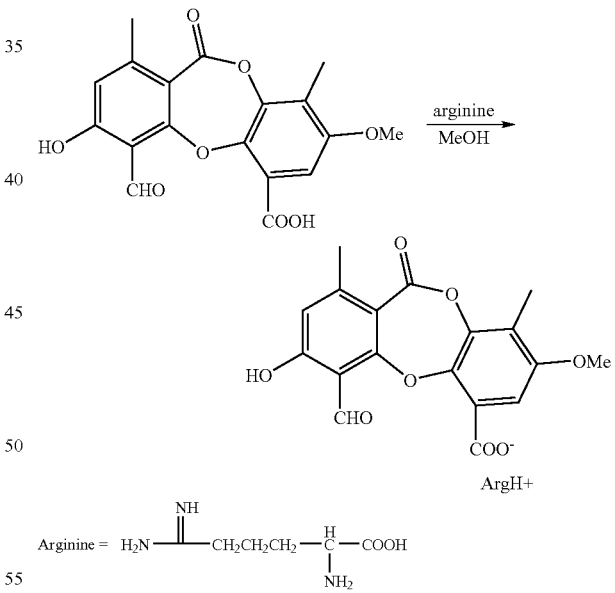

The process was as follows: 358 mg of F7 (1 mmol) was charged into a 100 ml round bottom flask, and an appropriate amount of ethanol was added. The mixture was heated as needed until the compound F7 was dissolved completely. A solution of L-Arginine (containing 348 mg L-Arginine, 2 mmol) in water was added, and the reaction mixture was stirred for another 1 h. After which, the flask was put into an ice bath, added dropwise with 3 fold amount of diethyl ether while stirring until a product was precipitated. The precipate was filtered to afford the salt.

Example 141

Preparation of Tablets and Capsules Comprising Compound F7

1. Tablets Comprising Compound F7

Amount: compound F7 25 g, starch 250 g, starch paste 50 g, talc powder 15 g, Liquid Paraffin (light) 0.25 g, 1000 tablets in total.

The procedure for the preparation is shown as follows: the compound F7 was ground into fine powders, and mixed with ⅓ of the starch homogeneously. Starch paste was added to make soft material. Granules were obtained by passing the soft material through a 14 mesh screen. The granules were dried at 70° C. and the dry masses were passed through a 12 mesh screen to sizing the granules. Mixing the granules with the remaining starch (pre-dried at 100~105° C.) and talc powder adsorbed with Liquid Paraffin thoroughly. The mixture was passed through a 12 mesh screen, tableted to obtain the products.

The tablet was used for treating diabetes. The content of active ingredient is 25 milligrams per tablet.

2. Capsules Comprising Compound F7

Amount: compound F7 25 g, starch 250 g, talc powder 15 g, 1000 capsules in total;

The procedure for the preparation is shown as follows: the compound F7 was ground into fine powders, and mixed with ⅓ of the starch homogeneously. The mixture was passed through a 80 mesh screen, and then mixed with the remaining starch and talc powder homogeneously. The resulting mixture was passed through a 14 mesh nylon screen, dried at 70° C. until the water content is below 3%. The solid was filled into bicolor transparent capsules to obtain the product.

The capsule was used for treating diabetes. The content of active ingredient is 25 milligrams per capsule.

Example 142

Hypoglycemic Effects of Psoromic Acid Extracts

*Lethariella cladonioides* (25 kg) was crushed into pieces, extracted with ethanol solution of different concentrations for 48 h, or heated under reflux for 3 h. The extracts were combined and concentrated under the reduced pressure to dryness, obtaining the crude extracts. The crude extracts were resuspended into water and extracted with ethyl acetate (EtOAc) to give the ethyl acetate phase and water phase.

Genetic spontaneous diabetes ob/ob mice were purchased from Jackson (USA), and maintained in a SPF facility (temperature: 22-24° C., humidity: 45-80%, illumination: 150-300 Lx, 12/12-hour light/dark cycle). Fasting blood glucose was determined for 3 days continuously when the mice were 7 weeks old. The mice were grouped into treatment group and control group (8 animals per group) according to the results determined. The two groups were administered orally with ethyl acetate phase (500 mg/kg) and a solution of 0.1% Tween 80 (as blank control) respectively, once daily for 3 weeks. Fasting Blood Glucose levels of mice were measured regularly, with results shown in Table 1. After 18 days, the fasting blood glucose level of the mice in the treatment group was reduced significantly by 20.4%, compared with that of the mice in the control group.

TABLE 1

|  |  | 0 day | 4 day | 8 day | 15 day | 18 day |
|---|---|---|---|---|---|---|
| Fasting Blood Glucose (mM) | Control Group | 11.6 ± 1.6 | 12.4 ± 2.3 | 12.8 ± 3.2 | 11.4 ± 1.5 | 12.1 ± 1.4 |
|  | Treatment Group | 11.6 ± 2.4 | 10.2 ± 1.7* | 10.2 ± 1.9 | 9.5 ± 1.1* | 9.6 ± 2.3* |

*P < 0.05, compared with the control group.

Example 143

Effects of the Heptacyclic Compounds on Glucose Uptake in 3T3-L1 Adipocytes

The effect of the compounds on baseline or insulin-stimulated glucose uptake was evaluated, using the model of glucose uptake in 3T3-L1 adipocytes.

Adipose tissue is the target of glucose metabolism in vivo. The sensitivity for insulin and availability of glucose in adipose tissues are tightly associated with the insulin resistance. The transportation of glucose into adipocytes is a rate-limiting step for the glucose metabolism, and also an important indicator for evaluating the sensitivity for insulin in adipose tissue. 3T3-L1 is a kind of pre-adipocyte, and can become adipocyte after differentiated completely. Therefore, 3T3-L1 is a desirable model for the glucose transport.

Pre-adipocyte, 3T3-L1 was induced to differentiate under certain conditions. After 3T3-L1 differentiated into adipocytes, the compounds of interest with different concentrations and DMSO (used as control) can be added and incubated with the adipocytes for different periods, then the glucose uptake could be determined. For evaluating the ability for a compound to stimulate glucose uptake, the baseline and insulin-induced glucose uptake were determined, and the increase in baseline and insulin-induced glucose uptake upon treatment of the compounds as compared with control group (with 0.1% DMSO) is calculated, based on the $^3$H-labelled 2-deoxyglucose inside the cells.

3T3-L1 cells purchased from Karolinska Institute (Sweden) were cultured in DMEM medium containing 10% fetal calf serum at 37° C., under 5% $CO_2$. The cells were passaged every 3-4 days. The cells were inoculated into 12-well plate. Upon confluence, culture medium containing 0.5 mM 3-isobutyl-1-methylxanthine, 0.25 μM dexamethasone and 5 μg/ml insulin was added and cultured for 3 days. Then, the culture medium was replaced by a medium containing 5 μg/ml insulin and further cultured for 3 days. The insulin was removed, and the cells had differentiated completely into mature adipocytes after 2 days which could be used to determine the glucose uptake.

23 compounds chosen by the inventors were added into the culture medium of adipocytes in a dose of 10 μM. After incubation for 2 h, the effect of the compounds on glucose uptake in 3T3-L1 cells was observed. Culture medium without compounds was used as negative control. The control group only supplemented with insulin and the experiment group supplemented with compounds plus insulin were also employed to observe the effect of the compounds on glucose uptake.

Experiment results are shown in table 2. The data demonstrate that the heptacyclic compounds tested can stimulate glucose uptake in 3T3-L1 cells. Meanwhile, the glucose uptake in 3T3-L1 cells supplemented insulin plus the heptacyclic compounds according to the invention was improved significantly, as compared with the cells only supplemented with insulin.

TABLE 2

|  | Mean | | SD | |
| --- | --- | --- | --- | --- |
| Compound Number | Control Group/ Compound Group | Control + Insulin Group/ Compound + Insulin Group | Control Group/ Compound Group | Control + Insulin Group/ Compound + Insulin Group |
| Control | 1.000 | 3.152 | 0.000 | 0.591 |
| F7 | 1.188 | 3.788 | 0.282 | 0.407 |
| Control | 1.000 | 2.986 | 0.000 | 0.194 |
| A0 | 1.334 | 2.710 | 0.227 | 0.406 |
| A2 | 1.366 | 3.138 | 0.133 | 0.283 |
| A4 | 1.182 | 3.449 | 0.344 | 0.371 |
| Control | 1.000 | 2.479 | 0.000 | 0.747 |
| B9 | 1.157 | 2.824 | 0.192 | 1.132 |
| Control | 1.000 | 4.160 | 0.000 | 0.884 |
| C1 | 1.213 | 4.059 | 0.436 | 1.184 |
| C3 | 1.316 | 4.834 | 0.106 | 1.223 |
| Control | 1.000 | 2.872 | 0.000 | 0.677 |
| C7 | 1.222 | 3.610 | 0.292 | 1.211 |
| Control | 1.000 | 3.257 | 0.000 | 0.376 |
| D1 | 1.284 | 3.673 | 0.223 | 1.111 |
| D3 | 1.116 | 3.001 | 0.075 | 0.664 |
| D4 | 1.189 | 3.717 | 0.314 | 1.222 |
| Control | 1.000 | 3.645 | 0.000 | 1.114 |
| D8 | 1.206 | 3.877 | 0.276 | 1.430 |
| Control | 1.000 | 2.665 | 0.000 | 0.280 |
| E9 | 1.100 | 2.965 | 0.093 | 0.206 |
| Control | 1.000 | 1.947 | 0.000 | 0.275 |
| AA0 | 1.118 | 2.130 | 0.227 | 0.454 |
| Control | 1.000 | 1.604 | 0 | 0.32 |
| AA7 | 1.129 | 1.786 | 0.058 | 0.13 |
| Control | 1.000 | 1.548 | 0.000 | 0.290 |
| AB2 | 1.179 | 1.639 | 0.175 | 0.281 |
| Control | 1.000 | 1.776 | 0.000 | 0.540 |
| AB4 | 1.109 | 1.837 | 0.164 | 0.389 |
| AB5 | 1.286 | 1.755 | 0.184 | 0.350 |
| Control | 1.000 | 1.531 | 0.000 | 0.691 |
| AB6 | 1.143 | 1.432 | 0.504 | 0.630 |
| Control | 1.000 | 1.431 | 0.000 | 0.016 |
| AB9 | 1.150 | 1.555 | 0.089 | 0.189 |
| G0 | 1.221 | 1.297 | 0.088 | 0.091 |
| Control | 1.000 | 1.784 | 0.000 | 0.597 |
| BT5 | 1.230 | 1.728 | 0.199 | 0.412 |
| Control | 1.000 | 2.033 | 0.000 | 0.365 |
| BU0 | 1.428 | 2.147 | 0.257 | 0.440 |

Example 144

The Effect of the Heptacyclic Compounds on the Phosphorylation of Acetyl CoA Carboxylase (ACC), AMP-Activated Protein Kinase (AMPK) in HepG2 Cell Human hepatoma carcinoma cell strain (HepG2, purchased from the cell bank of Shanghai Institute of Cell Biology of Chinese Academy) was used. The Human hepatoma carcinoma cells were passaged by 0.1% pancreatin/0.02% EDTA digestion, and cultured in a incubator at 37° C. using MEM culture medium containing 10% FBS, under 5% $CO_2$/95%.

HepG2 cells were cultured in 6-well plates for 48 hours until 70%-80% confluence. Serum starvation was started by changing medium with MEM containing 0.5% BSA. After starvation for 6 hours, cells were treated with the compounds (final concentration of 50 uM, containing 0.25% DMSO) for 5 minutes. The culture medium was discarded, and cells were harvested and washed for twice with pre-cooled PBS. The washing liquid was discarded, and any residual PBS was blotted dry. DMSO without heptacyclic compounds was used as control.

Extraction of total cellular protein: 150 µl/well homogenizing buffer (137 mM NaCl, 2.7 mM KCl, 1 mM $MgCl_2$, 0.5 mM $Na_3VO_4$, 1% Triton X-100, 10% Glycerol, 20 mM Tris-HCl pH 7.8, 1 ug/ml Leupeptin, 0.2 mM PMSF, 10 mM NaF, 1 ug/ml Aprotinin, 1 mM EDTA, 1 mM DTT, 5 mM Sodium pyrophosphate, 1 mM Benzamidine) was added. Cells were collected into a 1.5 ml centrifuge tube using cell scraper. Cells were homogenized using sonicator (5 W of power) for 2 times (3 seconds per time), and shaken on a shaker for 1 hour. Supernatant (i.e., total cellular protein) was collected by centrifuging at 14000 rpm for 15 min at 4° C., and stored at −70° C. until use. After the protein concentration was determined by Bradford method, the supernatant was formulated as the loading sample with final concentration of 0.6 mg/ml. The whole preparation process was performed at 4° C.

Protein Electrophoresis: After being treated at 95° C. for 5 min, the loading sample was loaded (15 µg protein/lane). The protein was separated on 7.5% SDS-acrylamide gel for 1-2 hours under the voltage of 80-120 V.

Electrotransferring the protein and blocking the membrane: After electrophoresis was finished, the protein was transferred to PVDF membrane using semi-dry transferring slot based on 0.8 $mA/cm^2$ membrane area under the electric current of 80 mA for 2 hours. After that, the membrane was shaken for 2 hours with 7.5% skim milk/TTBS to block the membrane.

Antigen-antibody reaction: After the blocking process was finished, the membrane was incubated with primary antibody (antibody against phosphorylated ACC (P-ACC) and antibody against phosphorylated AMPK (P-AMPK), all purchased from Cell signaling (USA), with the working concentration of 1:1000) overnight at 4° C. The membrane was removed, and the primary antibody was recovered. The membrane was washed 5 times, each for 10 min in TTBS. The membrane was shaken for 2 hours with the secondary antibody (horseradish peroxidase-conjugated goat-anti-rabbit IgG antibody, purchased from Bio-rad (USA), with the working concentration of 1:5000) at room temperature. The secondary antibody was discarded. The membrane was washed 5 times, each for 10 min in TTBS in order to remove the unbound secondary antibody.

ECL exposure and development: Luminescent agents, ECL 1, 2, were mixed homogeneously, and incubated with the membrane for 3-5 min. The membrane was removed, wrapped in preservative film, and transferred into dark room for exposure. After exposure with X-film, the film was developed, washed, recorded and conserved.

Semi-quantitative analysis was performed through optical density scan using computer image analysis system. Grey level of the protein expression was calculated. The target grey level was divided by the grey level of internal standard, and a histogram was plotted, taking the normal group as 1 unit.

Figure 2:
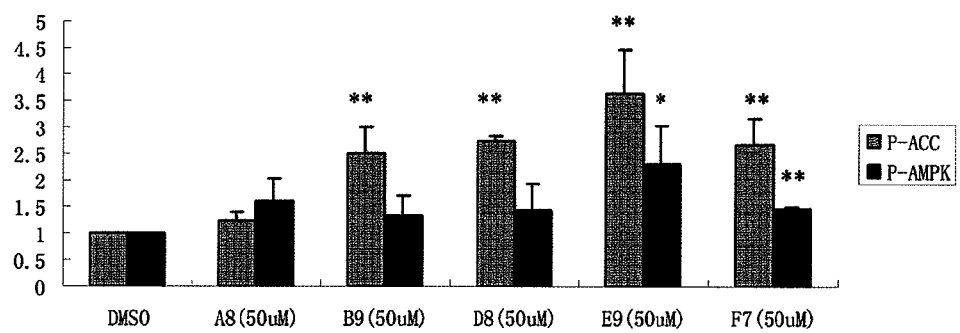
FIG. 2 shows the effect of some heptacyclic compounds on ACC, AMPK protein phosphorylation in HepG2 cell, **P<0.01; *P<0.05, versus DMSO.

The experiment data demonstrate that the level of phosphorylation for ACC protein in groups containing compound A0, A2, A4, A6, B9, D8, E9 and F7 was improved significantly ($P<0.01$, $P<0.05$), as compared with DMSO control group; and there was a significant up-regulation in the level of phosphorylation for AMPK protein in groups containing compound A2, A4, A6, E9 and F7 ($P<0.01$, $P<0.05$). The results are shown in FIGS. 1 and 2.

Figure 3:
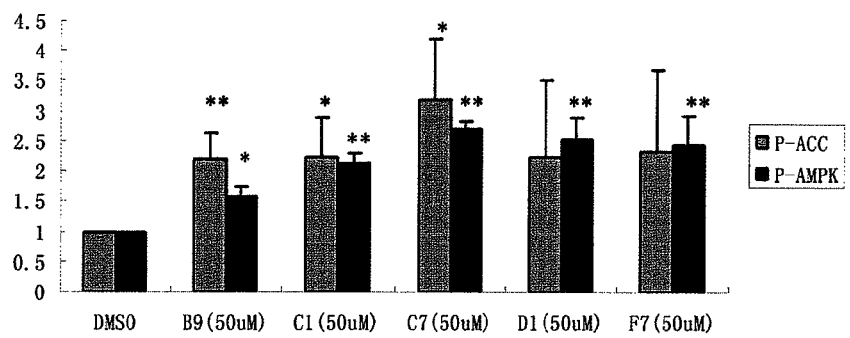
FIG. 3 shows the effect of some heptacyclic compounds on ACC, AMPK protein phosphorylation in HepG2 cell, **P<0.01; *P<0.05, versus DMSO.
Figure 4:
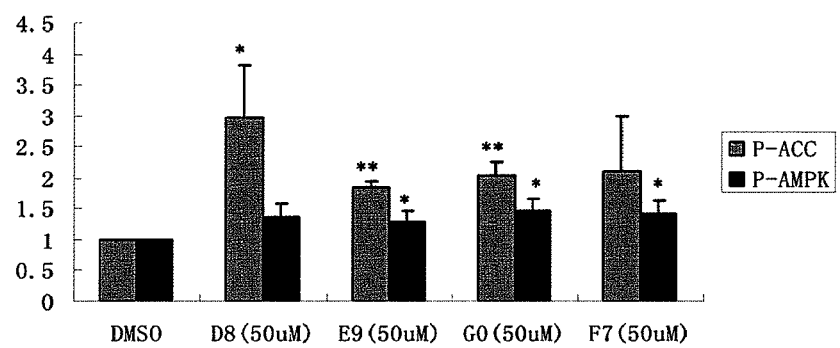
FIG. 4 shows the effect of some heptacyclic compounds on ACC, AMPK protein phosphorylation in HepG2 cell, **P<0.01; *P<0.05, versus DMSO.

The level of phosphorylation for ACC protein in groups containing compound B9, C1, C7, D8, E9 and G0 was improved significantly ($P<0.01$, $P<0.05$), as compared with DMSO control group; and the level of phosphorylation for AMPK protein in groups containing compound B9, C1, C7, D1, E9, G0 and F7 was increased significantly ($P<0.01$, $P<0.05$). The results are shown in FIGS. 3 and 4.

Figure 5:
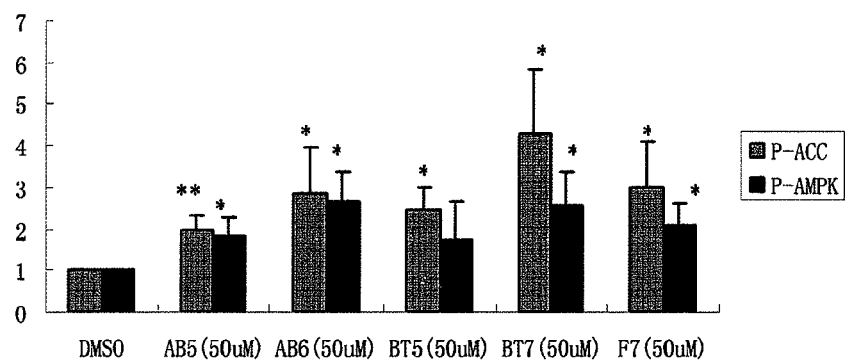
FIG. 5 shows the effect of some heptacyclic compounds on ACC, AMPK protein phosphorylation in HepG2 cell, **P<0.01; *P<0.05, versus DMSO.
Figure 6:
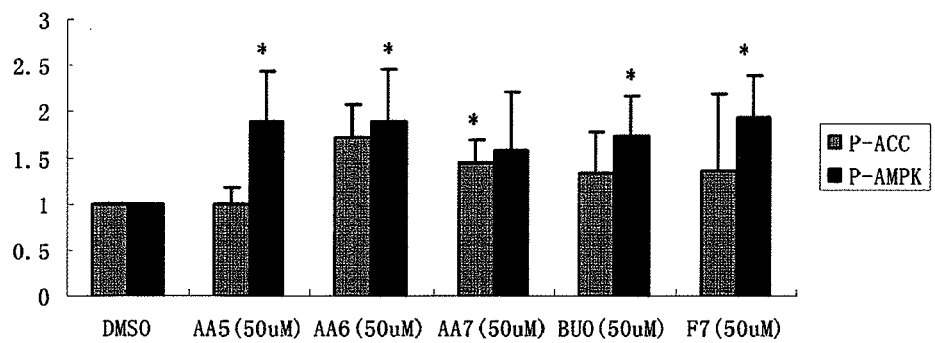
FIG. 6 shows the effect of some heptacyclic compounds on ACC, AMPK protein phosphorylation in HepG2 cell, *P<0.05, versus DMSO.

The level of phosphorylation for ACC protein in groups containing compound AB5, AB6, BT5, BT7, AA6, AA7 and F7 was improved significantly ($P<0.01$, $P<0.05$), as compared with DMSO control group; and the level of phosphorylation for AMPK protein in groups containing compound AB5, AB6, BT7, AA5, AA6, BU0 and F7 was increased significantly ($P<0.01$, $P<0.05$). The results are shown in FIGS. 5 and 6.

Example 145

Effect of Several Heptacyclic Compounds on Fasting Blood Glucose in ob/ob Mice Genetic spontaneous diabetes ob/ob mice were purchased from Jackson (USA), and maintained in a SPF facility (temperature: 22-24° C., humidity: 45-80%, illumination: 150-300 Lx, 12/12-hour light/dark cycle). Fasting blood glucose was determined for 3 days continuously when the mice were 7 weeks old. The mice were grouped into the treatment group and the control group (6 animals per group) according to the results determined. The treatment groups were administered orally with compound E9, G0 and F7 (psoromic acid) (100 mg/kg), and the control group was administered orally with a solution of 0.1% Tween 80 (blank control), once daily for 8 days. Fasting blood glucose in mice was determined at the end of experiment.

The results are shown in table 3. Fasting blood glucose of the mice, after being dosed continuously for 8 days, in treatment groups containing compounds F7, E9 and G0 was reduced statistically significant ($P<0.05$).

TABLE 3

|  |  | Before administration | After 8 days treatment |
|---|---|---|---|
| Fasting Blood Glucose (mM) | Control Group | 12.27 ± 1.53 | 11.50 ± 1.73 |
|  | E9 | 11.99 ± 1.48 | 8.68 ± 1.32* |
|  | G0 | 11.95 ± 1.49 | 8.07 ± 1.07** |
|  | F7 | 11.94 ± 1.50 | 8.12 ± 1.04** |
|  | Metformin | 12.27 ± 2.69 | 8.13 ± 2.76* |

*$P < 0.05$,
**$P < 0.01$, versus control group.

Example 146

Hypoglycemic Effect of Compound F7

Genetic spontaneous diabetes ob/ob mice were purchased from Jackson (USA), and maintained in a SPF facility (temperature: 22-24° C., humidity: 45-80%, illumination: 150-300 Lx, 12/12-hour light/dark cycle). Fasting blood glucose was determined for 3 days continuously when the mice were 7 weeks old. The mice were grouped into the treatment group and the control group (8 animals per group) according to the results determined. The two groups were administered orally with compound F7 (50 mg/kg) and a solution of 0.1% Tween 80 respectively, once daily for 3 weeks. Fasting Blood Glucose levels of mice were measured regularly.

The results are shown in Table 4. Fasting blood glucose of the mice, after being dosed continuously for 4 days, in treatment groups was reduced statistically significant ($P<0.05$). At day 15 after administration, the fasting blood glucose of mice in the Treatment Group was reduced by 42%. At day 21 after administration, the fasting blood glucose of mice in the Treatment Group was reduced to normal level (7.4 mM).

TABLE 4

|  |  | 0 day | 4 day | 8 day | 11 day | 15 day | 21 day |
|---|---|---|---|---|---|---|---|
| Fasting Blood Glucose (mM) | Control Group | 14.2 ± 1.7 | 17.6 ± 3.1 | 14.9 ± 2.4 | 13.5 ± 2.3 | 14.5 ± 4.4 | 13.7 ± 3.7 |
|  | Treatment Group | 14.0 ± 1.8 | 11.3 ± 2.5** | 11.1 ± 2.0** | 8.8 ± 1.5** | 8.5 ± 2.5** | 7.4 ± 1.3** |

*$P < 0.05$.
**$P < 0.01$, versus control group.

Example 147

Effect of Compound F7 on Glucose and Lipid Metabolic Disorder

Genetic spontaneous diabetes ob/ob mice were purchased from Jackson (USA), and maintained in a SPF facility (temperature: 22-24° C., humidity: 45-80%, illumination: 150-300 Lx, 12/12-hour light/dark cycle). Fasting blood glucose was determined daily for 3 days continuously when the mice were 7 weeks old. The mice were grouped into the treatment group and the control group (8 animals per group) according to the results determined. The two groups were administered orally with compound F7 (50 mg/kg) and a solution of 0.1% Tween 80 respectively, once daily for 3 weeks. Another group of C57 mice was used as normal control. At the end of administration, blood samples were collected in each group, the serum was separated and serum biochemical indicators were detected.

The results shown in Table 5 demonstrate that F7 can significantly reduce fructosamine (FRU), as well as triglycerides (TG), total cholesterol (TC), unsaturated free fatty acid (NFFA) and uric acid (UA) in ob/ob mice, suggesting that F7 can significantly ameliorate glucose and lipid metabolic disorder in diabetes mice.

Therefore, Compound F7 can treat or prevent diabetes, hypertension, impaired glucose tolerance (IGT), hyperuricacidemia, arthrolithiasis, hyperlipemia, hypercholesteremia or artherosclerosis due to glucose and lipid metabolic disorder.

TABLE 5

| Group | FRU (μmol/L) | CHOL (mmol/L) | TG (mg/dl) | NFFA (mmol/L) | UA (mmol/L) |
|---|---|---|---|---|---|
| Control | 364.2 ± 68.8 | 8.1 ± 1.0 | 97.9 ± 20.2 | 1.36 ± 0.26☐ | 576.4 ± 171.9 |
| Treatment | 225.0 ± 40.4*** | 6.0 ± 0.8*** | 72.1 ± 11.1** | 1.15 ± 0.17* | 316.5 ± 109.4** |
| Normal | 174.1 ± 24.8*** | 2.6 ± 0.5*** | 45.4 ± 8.9*** | 0.97 ± 0.24** | 259.1 ± 25.8** |

*P < 0.05.
**P < 0.01.
***P < 0.001, versus control group.

Example 148

Effect of Compound F7 on Triglyceride Level in Liver

Genetic spontaneous diabetes ob/ob mice were purchased from Jackson (USA), and maintained in a SPF facility (temperature: 22-24° C., humidity: 45-80%, illumination: 150-300 Lx, 12/12-hour light/dark cycle). When the mice were 7 weeks old, the ob/ob mice were grouped into the treatment group and the control group (9 animals per group) according to the fasting blood glucose. The two groups were administered orally with compound F7 (50 mg/kg) and a solution of 0.1% Tween 80 respectively, once daily for 3 weeks. After 3 weeks, the animals were sacrificed and the liver was excised and weighed.

The results shown in Table 6 demonstrated that the weight of liver in the group given F7 was significantly decreased (P<0.05), as compared with the control group; but F7 had no effect on the weight of other organs or its ratio to body weight. The triglyceride level in the liver was measured.

The results indicate that the triglyceride level in livers of the group given F7 was significantly reduced, as compared with the control group. Meanwhile, the results of serum biochemical assay demonstrate that the level of alanine aminotransferase (ALT) and aspartate aminotransferase (AST) in the group given F7 was slightly reduced, as compared with the control group, wherein the ALT level was statistically significant decreased (P<0.05).

Therefore, Compound F7 can treat or prevent obesity and adiposis hepatica due to elevation of triglyceride level in liver.

TABLE 6

| Group | Liver Weight (g) | Liver TG (μmol/g) | ALT(U/L) | AST(U/L) |
|---|---|---|---|---|
| Control Group | 3.40 ± 0.45 | 157.8 ± 11.7 | 288.5 ± 51.6 | 222.4 ± 22.8 |
| Treatment Group | 2.67 ± 0.57* | 106.9 ± 35.6*** | 161.5 ± 28.4* | 197.3 ± 24.6 |

*P < 0.05.
***P < 0.001, versus control group.

Example 149

Effect of Compound F7 on Body Weight

Male C57BL/6J mice were maintained a SPF facility (temperature: 22-24° C., humidity: 45-80%, illumination: 150-300 Lx, 12/12-hour light/dark cycle). When the mice were 4 weeks old, they were fed with a high-fat diet (purchased from Research Diets Inc. (USA), D12492i, fat content is 60%). After 12 weeks, diet-induced obese (DIO) mice model was established. Another group of mice fed with normal diet (D12450Bi, fat content is 10%) was used as a normal control group. The DIO mice were divided into two group according to body weights, and administrated orally F7 (50 mg/kg) or 0.1% Tween80 (the model control group) respectively, every afternoon just before black out for 5 weeks. The body weights of mice were measured daily, and the effect of Compound F7 on body weight was observed.

The results shown in Table 7 demonstrated that the body weight of DIO mice was increased by 11 g, as compared with normal control group. After orally administered with 50 mg/kg compound F7, the body weight of DIO mice was significantly reduced. 1 week after administration, the body weight of mice given the compound F7 was reduced by 2 g, as compared with the model control group. 5 weeks after administration, the body weight of mice given the compound F7 was reduced by 4.5 g, as compared with the model control group.

Therefore, Compound F7 can reduce body weight significantly.

TABLE 7

| Group | Administration schedule | | | | | |
|---|---|---|---|---|---|---|
| | 0 day | 7 day | 14 day | 21 day | 28 day | 35 day |
| Normal Control Group | 28.1 ± 0.9 | 27.9 ± 1.0 | 28.4 ± 1.3 | 28.4 ± 1.0 | 27.8 ± 1.0 | 27.6 ± 1.3 |
| Model Control Group | 39.1 ± 3.2 | 38.4 ± 3.7 | 38.1 ± 3.8 | 39.4 ± 4.3 | 40.1 ± 4.3 | 40.3 ± 4.9 |
| Treatment Group | 39.2 ± 3.8 | 36.4 ± 3.8 | 36.5 ± 4.2 | 36.2 ± 3.9 | 36.1 ± 2.6* | 35.8 ± 2.0** |

*P < 0.01.
**P < 0.01, versus model control group.

Example 150

Hypoglycemic Effect of the Combination of F7 with Insulin or Glibenclamide

Genetic spontaneous diabetes ob/ob mice were purchased from Jackson (USA), and maintained in a SPF facility (temperature: 22-24° C., humidity: 45-80%, illumination: 150-300 Lx, 12/12-hour light/dark cycle). Fasting blood glucose was determined daily for 3 days continuously when the mice were 7 weeks old. The mice were grouped into the pretreatment group of Compound F7 and non-pretreatment group (16 animals per group) according to the results determined. The groups were administered orally with compound F7 (50 mg/kg) or a solution of 0.1% Tween 80 respectively, once daily for 10 days. The pretreatment group and the non-pretreatment group were divided into two subsets (8 animals per subset) respectively, and subcutaneously injected with insulin (0.6 U/kg) or orally administered with Glibenclamide (25 mg/kg) respectively. Then, blood glucose levels were measured at different time points and the percentage of change in blood glucose level was calculated. The results shown in table 8 and 9 demonstrated that, after subcutaneously injected with insulin, the blood glucose level of the mice in the non-pretreatment group had not decreased significantly, while that of the mice in the pretreatment group was decreased significantly. Among these results, the percentages of change in blood glucose level at 15, 40 and 90 min are statistically significant. After orally administered with Glibenclamide, the blood glucose level of the mice in the non-pretreatment group was decreased slightly, while that of the mice in the pretreatment group was decreased significantly. Among these results, blood glucose levels at 1, 2 and 3 hour were decreased significant.

Therefore, ob/ob mice treated by F7 show better reactivity toward insulin or Glibenclamide, which indicates that Compound F7 may be combined with these medicaments to produce potent hypoglycemic effect.

TABLE 8

| Group | The percentage of change in blood glucose level measured at different time points after administration (%) | | | |
|---|---|---|---|---|
| | 15 minutes | 40 minutes | 90 minutes | 120 minutes |
| Insulin | 113.9 ± 8.3 | 96.3 ± 18.0 | 90.6 ± 14.7 | 101.6 ± 11.2 |
| Combination of F7 with insulin | 86.9 ± 21.0* | 71.8 ± 15.6* | 73.8 ± 11.5* | 91.8 ± 17.2 |

*P < 0.05, versus insulin group.

TABLE 9

| Group | The percentage of change in blood glucose level measured at different time points after administration (%) | | |
|---|---|---|---|
| | 1 h | 2 h | 3 h |
| Glibenclamide | 90.2 ± 7.3 | 76.7 ± 10.2 | 68.0 ± 7.3 |
| Combination of F7 with Glibenclamide | 79.9 ± 9.4* | 60.1 ± 17.3* | 58.0 ± 10.9* |

*P < 0.05, versus insulin group.

As demonstrated above, ob/ob mice treated by F7 show better reactivity toward insulin or Glibenclamide, which indicates that Compound F7 may be combined with these medicaments (or formulated into a compound preparation or a pharmaceutical composition containing the active ingredients) to produce potent hypoglycemic effect.

All literatures mentioned in the present application are incorporated by reference herein, as though individually incorporated by reference. Additionally, it should be understood that after reading the description above, many variations and modifications may be made by the skilled in the art, and these equivalents also fall within the scope as defined by the appended claims.

The invention claimed is:

1. A method for the treatment of diabetes and metabolic syndromes in mammals, which comprises administering to mammals in need thereof a therapeutically effective amount of the compound of Formula (I), geometric isomers, enantiomers, diastereoisomers, racemates, pharmaceutically acceptable salts thereof or their mixtures;

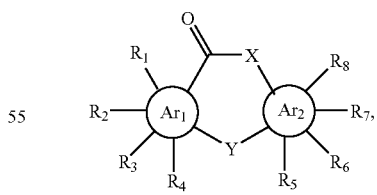

(I)

wherein, $Ar_1$ and $Ar_2$ are selected from benzene or heterocycle;

X is O;

Y is selected from O, N, S or $SO_2$;

$R_1$, $R_2$, $R_4$, $R_5$, $R_6$ and $R_8$ are independently selected from hydrogen, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, halo, —COOR', —NR'R", —OR', —COR', —CONR'R", =O, —SR', —SO$_3$R', —SO$_2$NR'R", —SO$_2$R', —NO$_2$ or —CN;

R$_3$ is independently selected from unsubstituted or substituted C$_1$-C$_{10}$ alkyl, unsubstituted or substituted C$_2$-C$_{10}$ alkenyl, unsubstituted or substituted C$_2$-C$_{10}$ alkynyl, halo, —COOR', —NR'R", —OR', —COR', —CONR'R", =O, —SR', —SO$_3$R', —SO$_2$NR'R", —SOR', —SO$_2$R', —NO$_2$ or —CN;

when R$_4$ is substituted C$_1$-C$_{10}$ alkyl, its substituent is selected from C$_{1-10}$ alkyl, C$_{2-10}$ alkenyl, C$_{2-10}$ alkynyl, halo, —COOR$_a$, —NR$_a$R$_b$, —OR$_a$, —COR$_a$, —CONR$_a$R$_b$, =O, —SR$_a$, —SO$_3$R$_a$, —SO$_2$NR$_a$R$_b$, —SOR$_a$, SO$_2$R$_a$, —NO$_2$, —CN; wherein R$_a$ and R$_b$ are selected from hydrogen, C$_{1-10}$ alkyl, C$_{2-10}$ alkenyl, or C$_{2-10}$ alkynyl;

R$_7$ is independently selected from unsubstituted or substituted C$_1$-C$_{10}$ alkyl, unsubstituted or substituted C$_2$-C$_{10}$ alkenyl, unsubstituted or substituted C$_2$-C$_{10}$ alkynyl, halo, —COOR', —NR'R", —OR', —COR', =O, —SR', —SO$_3$R', —SO$_2$NR'R", —SOR', —SO$_2$R', —NO$_2$ or —CN wherein R' and R" are independently selected from hydrogen, unsubstituted or substituted phenyl, unsubstituted or substituted benzyl, unsubstituted or substituted C$_1$-C$_{10}$ alkyl, unsubstituted or substituted C$_2$-C$_{10}$ alkenyl, unsubstituted or substituted C$_2$-C$_{10}$ alkynyl, or R' and R" are taken together to form a 4- to 7-membered ring.

2. The method of claim 1, wherein Ar$_1$ and/or Ar$_2$ is benzene.

3. The method of claim 1, wherein the metabolic syndromes are selected from insulin resistance, hyperinsulinemia, abnormal glucose tolerance, obesity, adiposis hepatica, hyperuricacidemia, arthrolithiasis, hyperlipemia, hypercholesteremia, artherosclerosis or hypertension.

4. A compound of the structure of Formula (I):

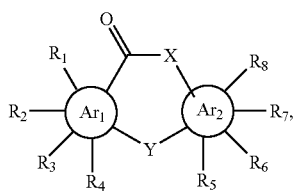

(I)

or geometric isomers, enantiomers, diastereoisomers, racemates, pharmaceutically acceptable salts thereof, wherein, Ar$_1$ and Ar$_2$ are selected from benzene or heterocycle;

X is O;

Y is selected from O, N, S or SO$_2$;

R$_3$ is —OR';

R$_1$ and R$_5$ are independently selected from H, unsubstituted or substituted C$_1$-C$_{10}$ alkyl, unsubstituted or substituted C$_2$-C$_{10}$ alkynyl, halo, —COOR', —NR'R", —OR', —COR', —CONR'R", =O, —SR', —SO$_3$R', —SO$_2$NR'R", —SOR', —SO$_2$R', —NO$_2$ or —CN;

R$_2$, R$_6$ and R$_8$ are independently selected from hydrogen, unsubstituted or substituted C$_1$-C$_{10}$ alkyl, unsubstituted or substituted C$_2$-C$_{10}$ alkenyl, unsubstituted or substituted C$_2$-C$_{10}$ alkynyl, halo, —COOR', —NR'R", —OR', —COR', —CONR'R", =O, —SR', —SO$_3$R', —SO$_2$NR'R", —SOR', —SO$_2$R', —NO$_2$ or —CN;

R$_4$ is independently selected from hydrogen, unsubstituted or substituted C$_1$-C$_{10}$ alkyl, unsubstituted or substituted C$_2$-C$_{10}$ alkenyl, unsubstituted or substituted C$_2$-C$_{10}$ alkynyl, halo, —COOR', —NR'R", —OR', —COR', —CONR'R", =O, —SR', —SO$_3$R', —SO$_2$NR'R", —SOR', —SO$_2$R', —NO$_2$ or —CN; wherein the substituents for the unsubstituted or substituted C$_1$-C$_{10}$ alkyl are 1-3 groups selected from the group consisting of: C$_1$-C$_{10}$ alkyl, C$_2$-C$_{10}$ alkenyl, C$_2$-C$_{10}$ alkynyl, halo, —COOR$_a$, —NR$_a$R$_b$, —OR$_a$, —COR$_a$, —CONR$_a$R$_b$, =O, —SR$_a$, —SO$_3$R$_a$, —SO$_2$NR$_a$R$_b$, —SOR$_a$, —SO$_2$R$_a$, —NO$_2$ or —CN, wherein R$_a$ and R$_b$ are independently selected from hydrogen, C$_1$-C$_{10}$ alkyl, C$_2$-C$_{10}$ alkenyl, or C$_2$-C$_{10}$ alkynyl;

R$^7$ is independently selected from unsubstituted or substituted C$_1$-C$_{10}$ alkyl, unsubstituted or substituted C$_2$-C$_{10}$ alkenyl, unsubstituted or substituted C$_2$-C$_{10}$ alkynyl, halo, —COOR', —NR'R", —OR', —COR', =O, —SR', —SO$_3$R', —SO$_2$NR'R", —SOR', —SO$_2$R', —NO$_2$ or —CN;

wherein R' and R" are independently selected from hydrogen, unsubstituted or substituted phenyl, unsubstituted or substituted benzyl, unsubstituted or substituted C$_1$-C$_{10}$ alkyl, unsubstituted or substituted C$_2$-C$_{10}$ alkenyl, unsubstituted or substituted C$_2$-C$_{10}$ alkynyl, or R' and R" are taken together to form a 4- to 7-membered ring;

and when R$_3$ is OH, R$_4$ is

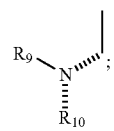

R$_9$ and R$_{10}$ are independently selected from H, unsubstituted or substituted phenyl, unsubstituted or substituted benzyl, unsubstituted or substituted C$_1$-C$_{10}$ alkyl, unsubstituted or substituted C$_2$-C$_{10}$ alkenyl, unsubstituted or substituted C$_2$-C$_{10}$ alkynyl, unsubstituted or substituted amino, —COR$_c$, —CONR$_c$R$_d$;

wherein R$_c$ and R$_d$ are independently selected from hydrogen, unsubstituted or substituted C$_1$-C$_{10}$ alkyl, unsubstituted or substituted C$_2$-C$_{10}$ alkenyl, unsubstituted or substituted C$_2$-C$_{10}$ alkynyl, or R$_c$ and R$_d$ are taken together to form a 4- to 7-membered ring.

5. The compound of claim 4, wherein Ar$_1$ and/or Ar$_2$ is benzene.

6. A compound of the structure of formula (II):

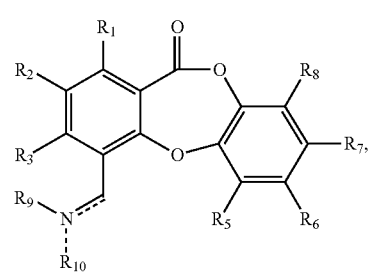

(II)

or geometric isomers, enantiomers, diastereoisomers, racemates, pharmaceutically acceptable salts thereof, $R_3$ is —OR';

$R_1$ and $R_5$ are independently selected from H, unsubstituted or substituted $C_1$-$C_{10}$ alkyl, unsubstituted or substituted $C_1$-$C_{10}$ alkynyl, halo, —COOR', —NR'R", —OR', —COR', —CONR'R", =O, —SR', —SO$_3$R', —SO$_2$NR'R", —SOR', —SO$_2$R', —NO$_2$ or —CN;

$R_2$, $R_6$ and $R_8$ are independently selected from hydrogen unsubstituted or substituted $C_1$-$C_{10}$ alkyl, unsubstituted or substituted $C_2$-$C_{10}$ alkenyl, unsubstituted or substituted $C_1$-$C_{10}$ alkynyl, halo, —COOR', —NR'R", —OR', —COR', —CONR'R", =O—SR', —SO$_3$R', —SO$_2$NR'R", —SOR', —SO$_2$R', —NO$_2$ or —CN;

$R_4$ is independently selected from hydrogen unsubstituted or substituted $C_1$-$C_{10}$ alkyl, unsubstituted or substituted $C_2$-$C_{10}$ alkenyl, unsubstituted or substituted $C_2$-$C_{10}$ alkynyl halo, —COOR', —NR'R", —OR', —COR', —CONR'R", =O, —SR', —SO$_3$R', —SO$_2$NR'R", —SOR', —SO$_2$R', —NO$_2$ or —CN; wherein the substituents for the unsubstituted or substituted $C_1$-$C_{10}$ alkyl are 1-3 groups selected from the group consisting of: $C_1$-$C_{10}$ alkyl, $C_2$-$C_{10}$ alkenyl, $C_2$-$C_{10}$ alkynyl, halo, —COOR$_a$, —NR$_a$R$_b$, —OR$_a$, —COR$_a$, —CONR$_a$R$_b$, =O, —SR$_a$, —SO$_3$R$_a$, —SO$_2$NR$_a$R$_b$, —SOR$_a$, —SO$_2$R$_a$, —NO$_2$ or —CN, wherein R$_a$ and R$_b$ are independently selected from hydrogen, $C_1$-$C_{10}$ alkyl, $C_2$-$C_{10}$ alkenyl, or $C_2$-$C_{10}$ alkynyl;

$R^7$ is independently selected from unsubstituted or substituted $C_1$-$C_{10}$ alkyl, unsubstituted or substituted $C_2$-$C_{10}$ alkenyl, unsubstituted or substituted $C_2$-$C_{10}$ alkynyl, halo, —COOR', —NR'R", —OR', —COR', =O—SR', —SO$_3$R', —SO$_2$NR'R", —SOR', —SO$_2$R', —NO$_2$ or —CN;

wherein R' and R" are independently selected from hydrogen, unsubstituted or substituted phenyl, unsubstituted or substituted benzyl, unsubstituted or substituted $C_1$-$C_{10}$ alkyl, unsubstituted or substituted $C_2$-$C_{10}$ alkenyl unsubstituted or substituted $C_2$-$C_{10}$ alkynyl, or R' and R" are taken together to form a 4- to 7-membered ring;

and when $R_3$ is OH, $R_4$ is

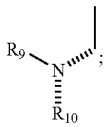

$R_9$ and $R_{10}$ are independently selected from H, unsubstituted or substituted phenyl, unsubstituted or substituted benzyl, unsubstituted or substituted $C_1$-$C_{10}$ alkyl, unsubstituted or substituted $C_2$-$C_{10}$ alkenyl, unsubstituted or substituted $C_2$-$C_{10}$ alkyl, unsubstituted or substituted amino, —COR$_c$, —CONR$_c$R$_d$;

wherein R$_c$ and R$_d$ are independently selected from hydrogen, unsubstituted or substituted $C_1$-$C_{10}$ alkyl, unsubstituted or substituted $C_1$-$C_{10}$ alkenyl, unsubstituted or substituted $C_2$-$C_{10}$ alkyl, or R$_c$ and R$_d$ are taken together to form a 4- to 7-membered ring.

7. The compound of claim 4, wherein the compound is selected from the group consisting of:

4-Formyl-3-hydroxy-8-methoxy-1,9-dimethyl-11-oxo-11H-dibenzo[b,e][1,4]dioxepine-6-carboxylic acid ethyl ester;

4-Formyl-3-hydroxy-8-methoxy-1,9-dimethyl-11-oxo-11H-dibenzo[b,e][1,4]dioxepine-6-carboxylic acid propyl ester;

3-Hydroxy-8-methoxy-1,9-dimethyl-11-oxo-4-phenylaminomethyl-11H-dibenzo[b,e][1,4]dioxepine-6-carboxylic acid;

3-Hydroxy-8-methoxy-1,9-dimethyl-11-oxo-4-[(2-pyrrol-1-yl-ethylamino)-methyl]-11H-dibenzo[b,e][1,4]dioxepine-6-carboxylic acid;

3-Hydroxy-8-methoxy-1,9-dimethyl-11-oxo-4-[(4-sulfamoylphenyl)-aminomethyl]-11H-dibenzo[b,e][1,4]dioxepine-6-carboxylic acid;

3-Hydroxy-8-methoxy-1,9-dimethyl-11-oxo-4-[(2-morpholin-4-yl-ethylamino)-methyl]-11H-dibenzo[b,e][1,4]dioxepine-6-carboxylic acid;

3-Hydroxy-8-methoxy-1,9-dimethyl-11-oxo-4-(piperazin-1-ylmethyl)-11H-dibenzo[b,e][1,4]dioxepine-6-carboxylic acid;

4-(tert-Butylamino-methyl)-3-hydroxy-8-methoxy-1,9-dimethyl-11-oxo-11H-dibenzo[b,e][1,4]dioxepine-6-carboxylic acid;

4-(4-Benzyl-piperazin-1-ylmethyl)-3-hydroxy-8-methoxy-1,9-dimethyl-11-oxo-11H-dibenzo[b,e][1,4]dioxepine-6-carboxylic acid;

4-[(4-Acetylamino-phenyl)aminomethyl]-3-hydroxy-8-methoxy-1,9-dimethyl-11-oxo-11H-dibenzo[b,e][1,4]dioxepine-6-carboxylic acid;

3-Hydroxy-4-hydroxymethyl-8-methoxy-1,9-dimethyl-11-oxo-1,1H-dibenzo[b,e][1,4]dioxepine-6-carboxylic acid;

4-[(4-Fluoro-phenylamino)-methyl]-3-hydroxy-8-methoxy-1,9-dimethyl-11-oxo-11H-dibenzo[b,e][1,4]dioxepine-6-carboxylic acid;

4-Formyl-3-hydroxy-8-methoxy-1,9-dimethyl-11-oxo-11H-dibenzo[b,e][1,4]dioxepine-6-carboxylic acid methylamide;

4-Formyl-3-hydroxy-8-methoxy-1,9-dimethyl-11-oxo-11H-dibenzo[b,e][1,4]dioxepine-6-carboxylic acid ethylamide;

4-Formyl-3-hydroxy-8-methoxy-1,9-dimethyl-11-oxo-11H-dibenzo[b,e][1,4]dioxepine-6-carboxylic acid diethylamide;

4-(Benzylimino-methyl)-3-hydroxy-8-methoxy-1,9-dimethyl-11-oxo-11H-dibenzo[b,e][1,4]dioxepine-6-carboxylic acid benzylamide;

3-Hydroxy-8-methoxy-1,9-dimethyl-11-oxo-4-[(4-sulfamoyl-phenyl)-imino-methyl]-11H-dibenzo[b,e][1,4]dioxepine-6-[carboxy-(4-sulfamoyl)-phenylamide];

4-Formyl-3-hydroxy-8-methoxy-1,9-dimethyl-11-oxo-11H-dibenzo[b,e][1,4]dioxepine-6-carboxylic acid butyl ester;

4-Formyl-3-hydroxy-8-methoxy-1,9-dimethyl-11-oxo-11H-dibenzo[b,e][1,4]dioxepine-6-carboxylic acid pentyl ester;

3-Hydroxy-8-methoxy-1,9-dimethyl-11-oxo-4-[(4-sulfamoylphenyl)-amino-methyl]-11H-dibenzo[b,e][1,4]dioxepine-6-carboxylic acid propyl ester;

3-Hydroxy-8-methoxy-1,9-dimethyl-11-oxo-4-[(2-morpholin-4-yl-ethylamino)-methyl]-11H-dibenzo[b,e][1,4]dioxepine-6-carboxylic acid propyl ester; and 4-[(4-Fluoro-phenylamino)-methyl]-3-hydroxy-8-methoxy-1,9-dimethyl-11-oxo-11H-dibenzo[b,e][1,4]dioxepine-6-carboxylic acid.

8. A composition comprising:
(a) an effective amount of a compound of Formula (I), geometric isomers, enantiomers, diastereoisomers, racemates, pharmaceutically acceptable salts thereof or their mixtures;

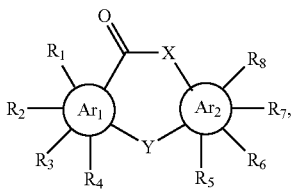

(I)

wherein $Ar_1$ and $Ar_2$ are selected from benzene or heterocycle;

X is O;

Y is selected from O, N, S or $SO_2$;

$R_3$ is —OR';

$R_1$ and $R_5$ are independently selected from H, unsubstituted or substituted $C_1$-$C_{10}$ alkyl, unsubstituted or substituted $C_2$-$C_{10}$ alkynyl, halo, —COOR', —NR'R", —OR', —COR', —CONR'R", =O, —SR', —SO$_3$R', —SO$_2$NR'R", —SO$_2$R', —NO$_2$ or —CN;

$R_2$, $R_6$ and $R_8$ are independently selected from hydrogen, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, halo, —COOR', —NR'R", —OR', —COR', —CONR'R", =O, —SR', —SO$_3$R', —SO$_2$NR'R", —SOR', —SO$_2$R', —NO$_2$ or —CN;

$R_4$ is independently selected from hydrogen, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, halo, —COOR', —NR'R", —OR', —COR', —CONR'R", =O, —SR', —SO$_3$R', —SO$_2$NR'R", —SOR', —SO$_2$R', —NO$_2$ or —CN; wherein the substituents for the unsubstituted or substituted $C_1$-$C_{10}$ alkyl are 1-3 groups selected from the group consisting of: $C_1$-$C_{10}$ alkyl, $C_2$-$C_{10}$ alkenyl, $C_2$-$C_{10}$ alkynyl, halo, —COOR$_a$, —NR$_a$R$_b$, —OR$_a$, —COR$_a$, —CONR$_a$R$_b$, =O, —SR$_a$, —SO$_3$R$_a$, —SO$_2$NR$_a$R$_b$, —SOR$_a$, —SO$_2$R$_a$, —NO$_2$ or —CN, wherein R$_a$ and R$_b$ are independently selected from hydrogen, $C_1$-$C_{10}$ alkyl, $C_2$-$C_{10}$ alkenyl, or $C_2$-$C_{10}$ alkynyl;

$R_7$ is independently selected from unsubstituted or substituted $C_1$-$C_{10}$ alkyl, unsubstituted or substituted $C_2$-$C_{10}$ alkenyl, unsubstituted or substituted $C_2$-$C_{10}$ alkynyl, halo, —COOR', —NR'R", —OR', —COR', =O, —SR', —SO$_3$R', —SO$_2$NR'R", —SOR', —SO$_2$R', —NO$_2$ or —CN;

wherein R' and R" are independently selected from hydrogen, unsubstituted or substituted phenyl, unsubstituted or substituted benzyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, or R' and R" are taken together to form a 4- to 7-membered ring;

and when $R_3$ is OH, $R_4$ is

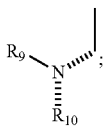

$R_9$ and $R_{10}$ are independently selected from H, unsubstituted or substituted phenyl, unsubstituted or substituted benzyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted $C_2$-$C_{10}$ alkynyl, unsubstituted or substituted amino, —COR$_c$, —CONR$_c$R$_d$:

wherein R$_c$ and R$_d$ are independently selected from hydrogen, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, or R$_c$ and R$_d$ are taken together to form a 4- to 7-membered ring;

(b) a bromatologically or pharmaceutically acceptable carrier or excipient.

9. The composition of claim 8, further comprising:

(c) one or more drugs selected from the group consisting of antidiabetic drugs, hypolipidemic drugs, weight-reducing aids, antihypertensive drugs and antithrombotic drugs.

10. The method of claim 1, wherein the compound having the structure of Formula (I), or geometric isomers, enantiomers, diastereoisomers, racemates, pharmaceutically acceptable salts thereof or their mixtures take effect by promoting the phosphorylation of acetyl CoA carboxylase and/or AMP-activated protein kinase in cells.

11. The method of claim 1, wherein the compound is selected from the group consisting of:

4-Formyl-3-hydroxy-8-methoxy-1,9-dimethyl-11-oxo-11H-dibenzo[b,e][1,4]dioxepine-6-carboxylic acid ethyl ester;

4-Formyl-3-hydroxy-8-methoxy-1,9-dimethyl-11-oxo-11H-dibenzo[b,e][1,4]dioxepine-6-carboxylic acid propyl ester;

3-Hydroxy-8-methoxy-1,9-dimethyl-11-oxo-4-phenylaminomethyl-11H-dibenzo[b,e][1,4]dioxepine-6-carboxylic acid;

3-Hydroxy-8-methoxy-1,9-dimethyl-11-oxo-4-[(2-pyrrol-1-yl-ethylamino)-methyl]-11H-dibenzo[b,e][1,4]dioxepine-6-carboxylic acid;

3-Hydroxy-8-methoxy-1,9-dimethyl-11-oxo-4-[(4-sulfamoylphenyl)-aminomethyl]-11H-dibenzo[b,e][1,4]dioxepine-6-carboxylic acid;

3-Hydroxy-8-methoxy-1,9-dimethyl-11-oxo-4-[(2-morpholin-4-yl-ethylamino)-methyl]-11H-dibenzo[b,e][1,4]dioxepine-6-carboxylic acid;

3-Hydroxy-8-methoxy-1,9-dimethyl-11-oxo-4-(piperazin-1-ylmethyl)-11H-dibenzo[b,e][1,4]dioxepine-6-carboxylic acid;

4-(tert-Butylamino-methyl)-3-hydroxy-8-methoxy-1,9-dimethyl-11-oxo-11H-dibenzo[b,e][1,4]dioxepine-6-carboxylic acid;

4-(4-Benzyl-piperazin-1-ylmethyl)-3-hydroxy-8-methoxy-1,9-dimethyl-11-oxo-11H-dibenzo[b,e][1,4]dioxepine-6-carboxylic acid;

4-[(4-Acetylamino-phenyl)aminomethyl]-3-hydroxy-8-methoxy-1,9-dimethyl-11-oxo-11H-dibenzo[b,e][1,4]dioxepine-6-carboxylic acid;

3-Hydroxy-4-hydroxymethyl-8-methoxy-1,9-dimethyl-11-oxo-11H-dibenzo[b,e][1,4]dioxepine-6-carboxylic acid;

4-[(4-Fluoro-phenylamino)-methyl]-3-hydroxy-8-methoxy-1,9-dimethyl-11-oxo-11H-dibenzo[b,e][1,4]dioxepine-6-carboxylic acid;

4-Formyl-3-hydroxy-8-methoxy-1,9-dimethyl-11-oxo-11H-dibenzo[b,e][1,4]dioxepine-6-carboxylic acid methylamide;

4-Formyl-3-hydroxy-8-methoxy-1,9-dimethyl-11-oxo-11H-dibenzo[b,e][1,4]dioxepine-6-carboxylic acid ethylamide;

4-Formyl-3-hydroxy-8-methoxy-1,9-dimethyl-11-oxo-11H-dibenzo[b,e][1,4]dioxepine-6-carboxylic acid diethylamide;

4-(Benzylimino-methyl)-3-hydroxy-8-methoxy-1,9-dimethyl-11-oxo-11H-dibenzo[b,e][1,4]dioxepine-6-carboxylic acid benzylamide;

3-Hydroxy-8-methoxy-1,9-dimethyl-11-oxo-4-[(4-sulfamoyl-phenyl)-imino-methyl]-11H-dibenzo[b,e][1,4]dioxepine-6-[carboxy-(4-sulfamoyl)-phenylamide];

4-Formyl-3-hydroxy-8-methoxy-1,9-dimethyl-11-oxo-11H-dibenzo[b,e][1,4]dioxepine-6-carboxylic acid butyl ester;

4-Formyl-3-hydroxy-8-methoxy-1,9-dimethyl-11-oxo-11H-dibenzo[b,e][1,4]dioxepine-6-carboxylic acid pentyl ester;

3-Hydroxy-8-methoxy-1,9-dimethyl-11-oxo-4-[(4-sulfamoylphenyl)-amino-methyl]-11H-dibenzo[b,e][1,4]dioxepine-6-carboxylic acid propyl ester;

3-Hydroxy-8-methoxy-1,9-dimethyl-11-oxo-4-[(2-morpholin-4-yl-ethylamino)-methyl]-11H-dibenzo[b,e][1,4]dioxepine-6-carboxylic acid propyl ester; and 4-[(4-Fluoro-phenylamino)-methyl]-3-hydroxy-8-methoxy-1,9-dimethyl-11-oxo-11H-dibenzo[b,e][1,4]dioxepine-6-carboxylic acid.

* * * * *